(12) United States Patent
Kaye et al.

(10) Patent No.: US 10,517,833 B2
(45) Date of Patent: ***Dec. 31, 2019

(54) USES OF MILRINONE CONTROLLED-RELEASE FORMULATION

(71) Applicant: Cardiora Pty Ltd., Melbourne (AU)

(72) Inventors: David Martin Kaye, Beaumaris (AU); Guy Krippner, Geelong (AU); Geetha Thanga Mariappan, Bangalore (IN)

(73) Assignee: Cardiora Pty Ltd., Melbourne (AU)

( * ) Notice: Subject to any disclaimer, the term of this patent is extended or adjusted under 35 U.S.C. 154(b) by 0 days.

This patent is subject to a terminal disclaimer.

(21) Appl. No.: 16/029,239

(22) Filed: Jul. 6, 2018

(65) Prior Publication Data

US 2018/0325826 A1 Nov. 15, 2018

Related U.S. Application Data

(62) Division of application No. 14/238,961, filed as application No. PCT/AU2012/000967 on Aug. 16, 2012, now Pat. No. 10,137,093.

(Continued)

(51) Int. Cl.
*A61K 9/20* (2006.01)
*A61K 9/28* (2006.01)
(Continued)

(52) U.S. Cl.
CPC .......... *A61K 9/2866* (2013.01); *A61K 9/2886* (2013.01); *A61K 9/4808* (2013.01); *A61K 9/4891* (2013.01); *A61K 31/444* (2013.01); *A61K 45/06* (2013.01); *A61K 9/2072* (2013.01); *A61K 2300/00* (2013.01)

(58) Field of Classification Search
None
See application file for complete search history.

(56) References Cited

U.S. PATENT DOCUMENTS

| 4,312,875 A | 1/1982 | Lesher et al. |
| 4,313,951 A | 2/1982 | Lesher et al. |

(Continued)

FOREIGN PATENT DOCUMENTS

| EP | 0 164 959 A2 | 12/1985 |
| GB | 2 065 642 B | 7/1981 |

(Continued)

OTHER PUBLICATIONS

Abraham et al. (2005) In-hospital mortality in patients with acute decompensated heart failure requiring intravenous vasoactive medications. An analysis from the acute decompensated heart failure national registry (ADHERE). Journal of the American College of Cardiology 2005;46(1):57-64.

(Continued)

*Primary Examiner* — Isis A Ghali
(74) *Attorney, Agent, or Firm* — Knobbe, Martens, Olson & Bear, LLP

(57) ABSTRACT

The present invention relates to oral controlled-release formulations of 5-(pyridinyl)-2(1H)-pyridinone compounds and their use in the treatment of a subject with heart failure, a stage, class or manifestation of heart failure, or at risk of developing or exhibiting symptoms of heart failure. The formulations of the invention release the compounds in the range of between 0.1 µg/kg body weight/minute and 20 µg/kg body weight/minute.

21 Claims, 4 Drawing Sheets

Related U.S. Application Data

(60) Provisional application No. 61/524,028, filed on Aug. 16, 2011.

(51) Int. Cl.
  *A61K 9/48* (2006.01)
  *A61K 45/06* (2006.01)
  *A61K 31/444* (2006.01)

(56) References Cited

U.S. PATENT DOCUMENTS

| | | |
|---|---|---|
| 4,806,361 A | 2/1989 | Harrison et al. |
| 4,871,548 A | 10/1989 | Edgren et al. |
| 5,009,895 A | 4/1991 | Lui |
| 5,213,811 A | 5/1993 | Frisbee et al. |
| 5,681,582 A | 10/1997 | Gilis et al. |
| 2004/0081693 A1 | 4/2004 | Woo et al. |
| 2005/0095292 A1 | 5/2005 | Benjamin et al. |
| 2009/0220611 A1 | 9/2009 | Dargelas et al. |
| 2011/0268799 A1 | 11/2011 | Dixit et al. |
| 2015/0018353 A1 | 1/2015 | Kim et al. |

FOREIGN PATENT DOCUMENTS

| | | |
|---|---|---|
| JP | 61-001614 A | 1/1986 |
| JP | 7-053364 A | 2/1995 |
| JP | 9-509412 A | 9/1997 |
| JP | 10-507210 A | 7/1998 |
| JP | 2004-143175 A | 5/2004 |
| JP | 2005-537298 A | 12/2005 |
| WO | WO 1995/020946 A1 | 8/1995 |
| WO | WO 1997/016172 A1 | 5/1997 |
| WO | WO 2004/012715 A1 | 2/2004 |
| WO | WO 2010/133815 A1 | 11/2010 |
| WO | WO 2013/023250 A1 | 2/2013 |
| WO | WO 2013/116194 A2 | 8/2013 |

OTHER PUBLICATIONS

Acharya et al. (2016) Infections, arrhythmias, and hospitalizations on home intravenous inotropic therapy. Am J Cardiol 2016; 117:952-956.
Al Kindi et al., "Sustained release of milrinone delivered via microparticles in a rodent model of myocardial infarction", 2014, *Journal of Thorac Cardiovasc Surg*, vol. 148, pp. 2316-2324.
Alousi et al., "Pharmacology of the bipyridines: Amrinone and Milrinone," *Circulation*, vol. 73(3 Pt 2), III10-III24 (1986).
Amsallem et al, Phosphodiesterase III inhibitors for heart failure (review), 2005, *Cochrane Database of Systematic Reviews*, 1, pp. 2 and 6.
Arakawa et al., "Milrinone for the Treatment of Cerebral Vasospasm After Subarachnoid Hemorrhage: Report of Seven Cases," *Neurosurgery*, vol. 48(4), pp. 723-728 (2001).
Bailey et al., "The Pharmacokinetics of Milrinone in Pediatric Patients After Cardiac Surgery," Anesthesiology, vol. 90(4), pp. 1012-1018 (Apr. 1999).
Baim et al., "Evaluation of a New Bipyridine Inotropic Agent—Milrinone—in Patients with Severe Congestive Heart Failure," *The New England Journal of Medicine*, vol. 309(13), pp. 748-756 (1983).
Butterworth et al., "A Pharmacokinetic and Parmacodynamic Evaluation of Milrinone in Adults Undergoing Cardiac Surgery," Anesthesia * Analgesia, vol. 81, No. 4, pp. 783-792 (1995).
Canver et al., "Milrinone for Long-term Pharmacologic Support of the Status 1 Heart Transplant Candidates," The annals of Thoracic Surgery,vol. 69, No. 6, pp. 1823-1826 (2002).
Cesario et al., "Beneficial Effects of Intermittent Home Administration of the Inotrope/Vasodilator Milrinone in Patients with End-state Congestive Heart Failure: a Preliminary Study," *American Heart Journal*, vol. 135(1), pp. 121-129 (1998).
Chang et al., "Milrinone: Systemic and Pulmonary Hemodynamic Effects in Neonates After Cardiac Surgery," *Critical Care Medicine*, vol. 23(11), pp. 1907-1914 (1995).
Clark et al., "Uncovering a Hidden Epidemic: a Study of the Current Burden of Heart Failure in Australia," *Heart Lung Circ*, vol. 13, pp. 266-273 (2004).
Colucci, W.S., "Cardiovascular Effects of Milrinone," *American Heart Journal*, vol. 121 (6 Pt 2), pp. 1945-1947 (1991).
Colucci et al., "Efficacy of phosphodiesterase inhibition with milrinone in combination with converting enzyme inhibitors in patients with heart failure", 1993, *JACC*, vol. 22(4), pp. 113A-8A.
Copp et al., "Overview of the Effects of Intravenous Milrinone in Acute Heart Failure Following Surgery," *European Journal of Anaesthesiology*, Supplement, vol. 5, pp. 35-41 (1992).
Cusick et al., "Effects of Intravenous Milrinone Followed by Titration of High-does Oral Vasodilator Therapy on Clinical Outcome and Rehospitalization Rates in Patients with Severe Heart Failure," *American Journal of Cardiology*, vol. 82(9), pp. 1060-1065 (1998).
Das et al., "Disposition of Milrinone in Patients After Cardiac Surgery," *British Journal of Anaesthesia*, vol. 72(4), pp. 426-429 (1994).
De Hert et al., "Comparison of Two Different Loading Doses of Milrinone for Weaning from Cardiopulmonary Bypass," *Journal of Cardiothoracic and Vascular Anesthesia*, vol. 9(3), pp. 264-271 (1995).
Doolan et al., "A Placebo-controlled Trial Verifying the Efficacy of Milrinone in Weaning High-risk Patients from Cardiopulmonary Bypass," *Journal of Cardiothoracic and Vascular Anesthesia*, vol. 11(1), pp. 37-41 (1997).
Foody et al., "β-blocker therapy in heart failure", 2002; *JAMA*, vol. 287(7), pp. 883-889.
Givertz et al., "Effect of Bolus Milrinone on Hemodynamic Variables and Pulmonary Vascular Resistance in Patients with Severe Left Ventricular Dysfunction: a Rapid Test for Reversibility of Pulmonary Hypertension," *J Am CollCardiol*, vol. 28(7), pp. 1775-1780 (1996).
Goldstein et al., "Electrophysiologic Effects of Milrinone in Patients with Congestive Heart Failure," *AmjCardiol*, vol. 57(8), pp. 624-628 (1986).
Gorodeski, et al., "Prognosis on chronic dobutamine or milrinone infusions for stage D heart failure," Circ Heart Fail., vol. 2. p. 320, Originally published online May 14, 2009, 9 pages.
Hasking et al., "Effect of autonomic blockade on the hemodynamic responses of normal human subjects to acute intravenous milrinone," *Journal of Cardiovascular Pharmacology* (1987), 9(5), 515-18.
Hayashida, et al. "Inhibitory effect of milrinone on cytokine production after cardiopulmonary bypass," The Annas of Thoracic Surgery, vol. 68, No. 5, 1661-1667 (1999).
He and Yang, "Inhibition of vasoconstriction by phosphodiestearase III inhibitor milrinone in human conduit arteries used as coronary bypass grafts," Journal of Cardiovascular Pharmacology, vol. 28, No. 2, pp. 208-214 (Aug. 1996), accessed from httg_://jou rnals.iww.corn/cardiovascu lar12 larm/Fuiitexti1996/08000i Inhibition of Vas con . . . , Apr. 24, 2014, 8 pages.
Hobbs, et al., "Impact of heart failure and left ventricular systolic dysfunction on quality of life: a cross-sectional study comparing common chronic cardiac and medical disorders and a representative adult population," European Heart Journal, vol. 23, No. 23, pp. 1867-1876 (Dec. 2002).
Hoffman, et al, "Efficacy and safety of milrinone in preventing low cardiac output syndrome in infants and children after corrective surgery for congenital heart disease," Circulation, vol. 107, No. 7, pp. 996-1002 (Feb. 25, 2003), published online Feb. 10, 2013, 8 paqes.
Juenger, et al., "Health related quality of life in patients with congestive heart failure: comparison with other chronic diseases and relation to functional variables," Heart, vol. 87, No. 3, pp. 235-241, (2002), 8 pages.
Kikura, et al., "The effect of milrinone on hemodynamics and left ventricular function after emergence from cardiopulmonary bypass," Anesthesia & Analgesia (Baltimore), vol. 85, No. 1, pp. 16-22 (1997).

(56) References Cited

OTHER PUBLICATIONS

Kumar, Dissolution, Remington, The Science of Practice and Pharmacy, 21$^{st}$ Edition, Lippincott Williams & Wilkins, pp. 672-680, 2006.
Leier, Carl V., "Positive inotropic therapy: an update an new agents" 1996, *Current problems in cardiology*, vol. 21(8), pp. 545-547.
Lloyd-Jones, et al., "Executive Summary: Heart Disease and Stroke Statistics—2010 Update: A Report from the American Heart Association", Circulation, vol. 121, pp. 948-954, and e259, (2010), 9 pages.
Metoprolol Succinate Extended-Release Tablets, NDA 19-962 /S-032, pp. 3-17, Rev. 03/06, appeared to be posted on FDA website https://www.accessdata.fda.gov/drugsatfda_docs/label/2006/019962s032lbl.pdf in May 2008 see https://www.accessdata.fda.gov/drugsatfda_docs/nda/2006/021956s000TOC.cfm.
Monrad, et al., "Improvement in indexes of diastolic performance in patients with congestive heart failure treated with milrinone," Circulation, vol. 70, No. 6, pp. 1030-1037 (Dec. 1984).
Monrad, et al., "Effects of milrinone on coronary hemodynamics and myocardial energetics in patients with conaestive heart failure," Circulation, vol. 71, No. 5, pp. 972-979 (May 1985).
Package Insert for Sanofi-Aventis U.S. LLC's PRIMACOR® (Milrinone Lactate Injection) product, dated 2007.
Packer et al., "Effect of oral milrinone on mortality in sever chronic heart failure" *The New England Journal of Medicine*, 1991, vol. 325(21), pp. 1468-1475.
Pinney et al., "Chronic inotropic therapy in the current era, old wines with new pairings", 2015, *Circ Heart Fail*, vol. 8, pp. 843-846.
Seino et al., "Hemodynamic effects and pharmacokinetics of oral milrinone for short-term support in acute heart failure" *Cardiology*, 1995, vol. 86, pp. 34-40.
Siegel and Rathbone, "Overview of controlled release mechanisms," which is Chapter 2, pp. 19-43 of J. Siepmann, et al. (eds.) *Fundamentals and Applications of Controlled Release Drug Delivery. Advances in Delivery Science and Technology*, DOI 10.1007/978-1-4614-0881-9_2, © Controlled Release Society 2012.
Timmis, et al., "Milrinone in heart failure—Acute Effects on left ventricular systolic function and myocardial metabolism," British Heart Journal, vol. 54, No. 1, pp. 36-41 (1985).
Wong, Haishan, The application of Milrinone in respiratory diseases, *Chinese Medical Journal of Metallurgical Industry*, 2010, vol. 27(3), pp. 251 (Chinese and inhouse translation into English).
Zewail, et al., "Intravenous milrinone in treatment of advanced congestive heart failure," Texas Heart Institute Journal, from the Texas Heart Institute of St. Luke's Episcopal Hospital, Texas Children's Hospital, vol. 30, No. 2, pp. 109-113 (2003).
Second Office Action for CN Application No. 201280050932.6 dated Jun. 3, 2016 in 4 pages, w/translation in 5 pages.
Edelmann et al., "Effect of spironolactone of diastolic function and exercise capacity in patients with hear failure with preserved ejection fraction", 2013, *JAMA*, vol. 309(8), pp. 781-791.
Edelson et al., "High-performance liquid chromatographic analysis of milrinone in plasma and urine: Intravenous pharmacokinetics in the dog", 1983, *Journal of Chromatography*, 276, pp. 456-462.
Hatzizacharias, et al., "Intermittent milrinone effect on long-term hemodynamic profile in patients with severe congestive heart failure," American Heart Journal (1999), 138(2 Pt. 1), 241-246.
Kibria et al., "Effect of plasticizer on release kinetics of diclofenac sodium pellets coated with eudragit RS 30 D", 2008, *AAPS PharmSciTech*, vol. 9(4), pp. 1240-1246.
Komajda et al., "Heart failure with preserved ejection fraction: a clinical dilemma", 2014, *European Heart Journal*, vol. 35(16), pp. 1022-1032.
Lobato et al., "Effects of milrinone versus epinephrine on grafted internal mannary artery flow after cardiopulmonary bypass," *Journal of Cardiothoracic and Vascular Anesthesia*, Feb. 2000, 14(1), 9-11.
Loffredo et al., "Heart failure with preserved ejection fraction: molecular pathways of the ageing myocardium", 2014, *Circ Res.*, vol. 115, pp. 97-107.
Marius-Nunez et al., "Intermittent inotropic therapy in an outpatient setting: a cost-effective therapeutic modality in patients with refractory heart failure," *American Heart Journal*, Oct. 1996, 132(4), 805-8.
McMurray et al., "Heart failure," *Lancet*, 365:1877-1889, May-Jun. 2005.
Marvin, M.H., "Diseases of the Heart and Blood Vessels. Nomenclature and Criteria for Diagnosis," *Arch Intern Med*, vol. 113(6), pp. 906-907 (1964).
Mehra et al., "Safety and clinicalutility of long-term intravenous milrinone in advanced heart failure," *American Journal of Cardiology*, vol. 80(1), pp. 61-64, Jul. 1997.
Messer et al., "Patterns of human mycardial oxygen extraction during rest and exercise," *J. Clin. Invest.*, 1962, 41:725-742.
Milfred-Laforest et al., "Tolerability of extended duration intravenous milrinone in patients hospitalized for advanced heart failure and the usefulness of uptitration of oral angiotensin-converting enzyme inhibitors," *American Journal of Cardiology*, 1999, vol. 84(8), pp. 894-899.
Nichols, Principles and Practice of Therapeutic Drub Monitoring, slides of James H. Nichols, Professor of Pathology, Microbiology and Immunology, Medical Director, Clinical Chemistry, Associate Medical Director of Clinical Operations, Vanderbilt University School of Medicine, Nashville, TN not dated, 39 slides.
Pamboukian et al., The use of milrinone in pre-transplant assessment of patients with congestive heart failure and pulmonary hypertension, *Journal of Heart and Lung Transplantation*, Apr. 1999, 18(4), 367-71.
Peltier et al., "Treatment practices in heart failure with preserved left ventricular ejection fraction: A prospective observational study", 2007, *International Journal of Cardiology*, vol. 118(3), pp. 363-369.
Redfield et al., "Effect of phosphodiesterase-5 inhibition on exercise capacity and clinical status in heart failure with preserved ejection fraction: A randomized clinical trial", 2013, *JAMA*, vol. 309(12), pp. 1268-1277.
Seino et al., "Multicenter, double-blind study of intravenous milrinone for patients with acute heart failure in Japan," *Critical Care Medicine*, Sep. 1996, vol. 24(9), pp. 1490-1497.
Sharma et al., "Heart failure with preserved ejection fraction: mechanisms, clinical features and therapies", 2014, *Circulation Research*, vol. 115, pp. 79-96.
Wright et al., "Milrinone in the treatment of low output states following cardiac surgery," *European Journal of Anaesthesiology*, 1992, vol. 5:21-6.
Yancy et al., "2013 ACCF/AHA Guideline for the management of heart failure: A report of the American College of Cardiology Foundation/American Heart Association task force on practice guidelines", 2013, *Circulation*, vol. 128, pp. e240-e327.
Extended European Search Report for Application No. 12824391.2-1464 dated Mar. 11, 2015 in 7 pages.
Extended European Search Report for Application No. 15871347.9-1109 dated Jul. 11, 2018 in 11 pages.
International Preliminary Report on Patentability for Application No. PCT/AU2012/000967 dated Feb. 18, 2014 in 5 pages.
International Search Report for PCT/AU2015/050820 dated Feb. 5, 2016 in 4 pages.
International Preliminary Report on Patentability for Application No. PCT/AU2015/050820 dated Aug. 2, 2016 in 4 pages.
Japanese Office Action dated Mar. 24, 2016 for Japanese Patent Application No. JP 2014-525260 in 7 pages.

USES OF MILRINONE CONTROLLED-RELEASE FORMULATION

FIELD OF THE INVENTION

The present invention relates to controlled-release formulations of cardiotonic 5-(pyridinyl)-2(1H)-pyridinone compounds and their use in the treatment of a subject with heart failure, a stage, class or manifestation of heart failure, or at risk of developing or exhibiting the symptoms of heart failure.

BACKGROUND OF THE INVENTION

Bibliographic details of the publications referred to by author in this specification are collected alphabetically at the end of the description.

Reference to any prior art in this specification is not, and should not be taken as, an acknowledgment or any form of suggestion that this prior art forms part of the common general knowledge in any country.

Of the diseases affecting the systemic vasculature, coronary heart disease remains one of the major causes of premature mortality and morbidity (Lloyd-Jones et al, 2010). Whereas some patients with coronary artery disease experience chronic angina without evident myocardial infarction, other patients may experience myocardial infarction as an initial symptom prior to developing heart failure (HF). As such, coronary artery disease and its sequelae are the cause of approximately 50% of the cases of HF.

HF is an emerging epidemic that claims approximately 10,000 Australian lives each year, with a recent study estimating that there are 500,000 heart failure patients (Clark R A, et al., 2004). The disease burden includes over 1.4 million days of hospitalization at a cost of more than 1 billion dollars [Clarke, 2004]. Globally, approximately 23 million people have HF, which can arise from many causes, including valvular disease, coronary artery disease, coronary occlusive events, hypertension and cardiomyopathy. Most HF patients experience a gradual onset of the disease, with a smaller proportion experiencing a rapid onset of heart failure which is secondary to abnormal cardiac function (acute HF).

Heart failure is the inability of the heart to circulate enough blood to meet the metabolic demands of the body's tissues due to a reduced cardiac output. Heart failure is not a single disease but represents the consequences of a number of disease processes. It can result from any functional or structural disorder and is a principal complication in virtually all forms of heart disease. The ESC (European Society of Cardiology) guidelines (European Heart Journal (2008) 29, 2388-2442) recommend that HF should never be the only diagnosis. Although the two are often used interchangeably, the terms congestive heart failure and HF are not entirely synonymous. Although no definition of HF is entirely satisfactory, essentially it applies to any deficiency of the pumping mechanism of the heart. Congestive heart failure develops when plasma volume increases and fluid accumulates in the lungs, abdominal organs (especially the liver) and/or peripheral tissues in the compensatory response. The ACC/AHA 2007 guidelines state that as not all patients have volume overload, the term heart failure is preferred over the older term congestive heart failure.

Acute heart failure (AHF) is a term used to describe the rapid onset of symptoms secondary to abnormal cardiac function. This can be related to systolic or diastolic dysfunction, pre-load and after-load mismatch and abnormalities in cardiac rhythm. AHF can present as acute de novo AHF (in patients with no previously known cardiac dysfunction) or acute decompensation of chronic heart failure; it requires urgent treatment and is often life-threatening. AHF is characterized by reduced cardiac output, tissue congestion, an increase in pulmonary capillary wedge pressure and tissue hypoperfusion. The underlying mechanisms may induce permanent damage, leading to chronic heart failure, or be transient with the acute syndrome being reversed. Patients with AHF experience a high rate of rehospitalization, which highlights a need for more effective treatments in this area. The ESC guidelines (2005) state that appropriate long-term therapy and, where possible, the anatomical correction of the underlying cause may prevent further AHF attacks and improve the poor long-term prognosis associated with this syndrome.

A patient with AHF may present one of a number of distinct clinical conditions which may differ in severity:
hypertensive AHF: Al-IF accompanied by high blood pressure and relatively preserved left ventricular function;
left heart failure: with features ranging from breathlessness to frank pulmonary edema accompanied by severe respiratory distress and requiring ventilator support;
cardiogenic shock: the condition is defined as tissue hypoperfusion induced by HF after the correction of preload. Cardiogenic shock is characterized by low blood pressure and/or low urine production, a heart rate of >60 bpm with or without evidence of organ congestion;
high output failure: characterized by high cardiac output, usually with high heart rate, warm peripheries, pulmonary congestion and sometimes with low blood pressure;
right heart failure: characterized by low output syndrome with increase jugular venous pressure, increase liver size and hypotension.

Chronic heart failure (CHF) is the most common form of heart failure and is difficult to define due to its complex nature. The clinical syndrome may result from disorders of the pericardium, myocardium, endocardium, or great vessels. The resulting reduced cardiac output leads to a decrease in tissue perfusion and perceived volume depletion. The body compensates for this in various ways:
increasing fluid retention (edema);
activating the renin angiotensin system (RAS), which increases blood volume and causes constriction of blood vessels;
increasing hormone production, which causes the heart to pump faster and stronger;
hypertrophy of the heart walls, to strengthen pumping ability;
remodeling: enlargement and thinning of the left ventricle, this results in an increased use of oxygen and decreased ejection fraction. A contributing factor is the release of hormones in response to inflammation. This remodeling causes progressive heart cell damage leading to reduced cardiac output and more severe heart disease.

This compensatory response begins a cycle that contributes to the already failing heart. This would imply that early diagnosis and aggressive treatment are of utmost importance to the successful management of this syndrome.

The diagnosis of HF relies on clinical judgment based on the patient's history, a physical examination, and appropriate investigations. The fundamental manifestations are dyspnea (breathlessness), fatigue and fluid retention which may lead to pulmonary congestion and peripheral edema. The origins of the symptoms of HF are not fully understood, although the understanding has moved from a hemodynamic concept into accepting the importance of neuroendocrine and pathophysiological changes in the progression, as well as the management of HF. Activation of various inflammatory pathways may also contribute to cardiac dysfunction, particularly in more advanced stages.

HF presents with a spectrum of diagnostic criteria and is distinct from cardiac-related conditions such as myocardial infarction, cardiac arrest, and cardiomyopathies although such events can lead to HF (McMurray and Pfeffer, 2005).

HF is associated with significantly reduced physical, mental and behavioural health and results in a significant reduction in the quality of life (Juenger et al, 2002; Hobbs et al., 2002).

HF is generally classified functionally from Class I, requiring no physical limitations on patients to Class IV, where any form of physical activity induces discomfort (Diseases of the heart and blood vessels. Nomenclature and Criteria for diagnosis, 6.sup.th ed. Boston: Little, Brown and Co., 1964; 114). More recently, HF has been graded from Stage A, where patients are at risk of developing HF but appear to exhibit no structural disorder through to Stage D, in advanced cases where patients require hospital-based support, (AHA/ACC HF Guidelines, 2009). Treatment algorithms for HF are generally well developed (AHA/ACC HF Guidelines, 2009) which include the use of a range of pharmacologic drug classes based upon HF stage and severity. In severe stages the use of intravenous positive inotropic therapy is described. Inotropic therapies such as dobutamine and milrinone improve cardiac output. Milrinone has other advantageous properties including vasodilation.

Milrinone is a phosphodiesterase 3 inhibitor and has been approved for use in the treatment of congestive HF by the FDA. Milrinone lactate is formulated for use following a protocol whereby an intravenous loading dose of 50 µg/kg over 10 minutes, followed by a maintenance infusion of 0.375 to 0.75 µg/kg/minute is recommended for the treatment of congestive HF. The infusion rate should be adjusted according to hemodynamic and clinical response (Prod Info Primacor®). Duration of therapy should depend on patient responsiveness. In a Japanese multi-center dosing study in patients with AHF (n=:54), milrinone continuous infusion doses of 0.25, 0.5, or 0.75 µg/kg (after a loading dose of 50 gg/kg) provided plasma milrinone concentrations of 97, 197, and 284 ng/mL, respectively, after 6 hours, ie, at equilibrium. Plasma milrinone concentrations ranging from 150 to 200 ng/mL have been found to produce significant and sustained inotropic and vasodilating effects. Only the lowest infusion dose (0.25 µg/kg) failed to provide concentrations within the range thought to be effective (Seino et al., 1996).

Milrinone is a bipyridine inotropic agent with a similar chemical structure to aminone. The chemical name of milrinone is 1,6-dihydro-2-methyl-6-oxo-(3,4-bipyridine)-5-carbonitrile (Baim et al., 1983). The inotropic potency of milrinone is approximately 20 times that of aminone on a weight basis (Alousi et al., 1986). Milrinone has been well tolerated, intravenously, in phase I and phase II studies, and appears to lack the side effects seen with aminone (fever, thrombocytopenia) (Baim et al., 1983). Milrinone possesses inotropic, lusitropic, and vasodilator properties. These properties are clinically advantageous in congestive HF; they allow maximal improvement in hemodynamic performance without excessively increasing myocardial oxygen demand (Baim et al., 1983).

Milrinone exerts its vasodilatory action by selectively inhibiting cyclic adenosine monophosphate (AMP)-specific phosphodiesterase III isoenzyme in cardiac and smooth vascular muscle. The increase in vascular muscle AMP facilitates calcium uptake by the sarcoplasmic reticulum, thereby reducing calcium stores available for myofibril contraction, with subsequent reduction of vascular tone (Arakawa et al., 2001).

The primary mechanism of action of milrinone appears to be related, at least in part, to phosphodiesterase inhibition and resultant increases in intracellular cyclic AMP, which improves calcium handling (Colucci, 1991). Additional direct effects on transmembrane calcium fluxes may also occur (Monrad et al., 1985). The drug has produced stimulatory effects on calcium ATP-ase (Monrad et al, 1985).

Administration of milrinone in patients with congestive HF produced significant improvement in the indexes of left ventricular diastolic relaxation and filling, which is consistent with an effect on relaxation at the level of the myocardial cell (Monrad et al., 1984). It is speculated that improvement in diastolic function contributes to the hemodynamic improvements observed in congestive heart failure (CHF).

Intravenous milrinone enhanced cardiac performance in CHF patients without producing a systemic increase in myocardial oxygen consumption (Monrad et al., 1985). Cardiac index increased by 45% following doses of 125 µg/kg, with a 39% decrease in pulmonary capillary wedge pressure and a 42% increase in left ventricular external work. The heart rate-blood pressure product and regional left ventricular myocardial oxygen consumption remained unchanged, resulting in a 45% increase in calculated left ventricular external efficiency. Regional great cardiac venous blood flow increased significantly as a result of reductions in regional coronary vascular resistance, and the transcoronary arterial-venous oxygen difference decreased by 11%, which is consistent with the primary coronary vasodilator effects of the drug. It is speculated that milrinone may improve coronary flow reserve by direct coronary vasodilation and/or a reduction in left ventricular diastolic pressure.

Intravenous milrinone produced decreases in left ventricular end-diastolic pressure, pulmonary wedge pressure, right atrial pressure and systemic vascular resistance (Baim et al., 1983). These decreases were associated with a 50% increase in cardiac index, a slight decrease in mean arterial pressure (6%) and a slight increase in resting heart rate (8%). An increase of 28% was observed in the peak positive first derivative of left ventricular pressure (dP/dT), providing evidence of a direct positive inotropic effect. Hemodynamic improvement was sustained during a 24-hour continuous intravenous infusion with milrinone. Another study measured the hemodynamic effects of intravenous milrinone both alone and following autonomic blockade with prazosin, propranolol, atropine, and clonidine (Hasking et al., 1987). Milrinone alone produced increases in heart rate (21 beats/min, maximum) and cardiac output (44%+/−9%) with a reduction in systemic vascular resistance (32%). With autonomic blockade, a smaller rise in heart rate (7 beats/min), no change in cardiac output, and the same reduction in systemic vascular resistance was measured with milrinone. The authors speculate that milrinone increases cardiac output by an indirect mechanism.

Intravenous milrinone enhances atrioventricular conduction and may decrease the incidence of inducable ventricular tachycardia in patients with CHF (Goldstein et al., 1986). Ten patients with class III or IV CHF were given milrinone infusions of 0.5 µg/kg/min. Holter monitoring was performed for 48 hours at baseline and during the infusion of milrinone. The frequency of ventricular premature complexes (PVCs) and ventricular couplets did not significantly change. None of the patients had a proarrhythmic effect, however, the frequency of ventricular tachycardia (VT) increased significantly. On electrocardiogram, the PR, QRS, QTc, AH, and HV intervals were not affected with milrinone. Milrinone also did not affect the heart rate or atrial, atrioventricular and ventricular effective and functional refractory periods. During programmed right ventricular stimulation, 5 patients had inducable VT at baseline, whereas after milrinone therapy none of the patients experienced inducible VT.

A small randomized, controlled study in patients undergoing cardiopulmonary bypass (CPB; n=24) suggests that perioperative milrinone may increase cyclic adenosine monophosphate levels and suppress production of certain cytokines, including interleukin-1-beta (IL1-beta) and interleukin-6 (IL6). Inhibition of systemic inflammatory effects during cardiac surgery is thought to have a modulating effect on the immune system that may prevent degradation of organ systems, which in high-risk patients can lead to organ system failure. Study subjects randomized to milrinone received a continuous intravenous infusion at the rate of 0.5 µg/kg/minute for 24 hours from the time of induction of anesthesia. Plasma concentrations of IL1-beta and IL6 were significantly lower in the milrinone group compared with levels in the control group after CPB (p less than 0.05), while concentrations of cyclic adenosine monophosphate were significantly increased in the milrinone group compared to controls (p less than 0.05). No differences were observed for tumor necrosis factor-alpha or interleukin-8 (Hayashida et al., 1999).

One study suggests that milrinone may have efficacy in reducing vasoconstriction of arterial grafts to be used for coronary bypass (He and Yang, 1996). Human internal mammary arterial rings bathed in vitro in potassium chloride ($K^+$), endothelin-1 (ET-1), U46619, and phenylephrine (PE) exhibited significantly less vasoconstricition when pretreated with milrinone.

Short Term Use

Oral milrinone was evaluated in 100 patients with severe. CHF (Baim et al., 1986). Baseline hemodynamic measurements were obtained during right heart catheterization following a single intravenous bolus injection of milrinone (dose not provided). Subsequently, oral milrinone was administered 3 to 6 times daily in a total daily dose of 20 to 50 mg with concomitant digitalis, diuretics, vasodilators, and antiarrhythmics. Patients were evaluated monthly on an outpatient basis. The average dose of oral milrinone was 27 mg/day. Adverse effects occurred in 11% of patients and led to drug withdrawal in 4%. Within 1 month of therapy, 51% of the remaining 94 patients indicated improvement by at least one New York Heart Association functional class. Despite the hemodynamic and clinical improvements, a 39% mortality rate at 6 months and a 63% mortality rate at 1 year of therapy was observed. (NOTE: The oral form of milrinone was withdrawn in 1990).

Ten patients with endstage CHF were maintained as outpatients for 3 months on intermittent lowdose milrinone (Cesario et ed., 1998). This preliminary study enrolled patients who had shown hemodynamic improvement with milrinone during hospitalization. Outpatient doses of milrinone were 0.375 to 0.75 µg/kg/minute infused over 6, 8, or 12 hours via portable infusion pumps on 3 or 4 days per week. Number of hospitalizations dropped fourfold compared with the preceding 3 months. Some hemodynamic, symptomatic, and functional improvement occurred over the study period. Arrhythmia was minimal, with one patient exhibiting an increase; angina was mostly unchanged, although 2 patients reported reduced angina.

Oral milrinone 20 mg daily was associated with improvement in left ventricular function during exercise in patients with CHF (Timmis et al., 1985). The improvement in left ventricular function was reflected by increases in cardiac index and stroke volume index without changes in pulmonary capillary wedge pressure. The drug also increased systemic oxygen consumption and maximal exercise capacity. Beneficial hemodynamic effects were sustained throughout four weeks of treatment with milrinone (Timmis et al., 1985).

Long Term Use

An intermittent dosing protocol of intravenous milrinone in responding patients with endstage CHF (NYHA mean ejection fraction 17%) significantly improved hemodynamic parameters, and at 4 months after withdrawal of milrinone, significant hemodynamic improvements were sustained. The open-label protocol consisted of four 72-hour cycles with 20-day intervals between cycles. The 72-hour cycle was comprised of a loading does of 50 µg/kg over 10 minutes followed by continuous milrinone infusion, 0.5 µg/kg/minute for 72 hours. Hemodynamic measurements at the beginning of the fourth cycle were significantly improved over baseline values: increased cardiac index (CI), decreased mean pulmonary arterial pressure (PAP), decreased mean capillary wedge pressure (PCWP), decreased systemic vascular resistance (SVR), and decreased pulmonary vascular resistance (PVR) (p less than 0.01, all parameters). At 4 months after the fourth 72-hour milrinone cycle, significantly improved hemodynamics compared with baseline was maintained: CI, PAP, PCWP, SVR, and PVR (p less than 0.05, all parameters). No deaths occurred during the study (Hatzizacharias et al., 1999).

Intermittent, intravenous outpatient milrinone therapy in refractory HF patients resulted in fewer hospital and emergency room admissions over a 12-month study period compared with the previous 12 months (Marius-Nunez et al., 1996). Thirtysix NYHA functional class III and IV HF patients were given a milrinone loading dose of 50 µg/kg over a 10- to 20-minute period, followed by a constant infusion of 0.5 mg/kg/minute for 4 hours. Some patients received once weekly infusions while most received twice weekly infusions. Comparing the previous year with the 12-month study, emergency room admissions fell from 21 to 10, hospital admissions from 75 to 34, and hospital days from 528 to 150. No serious side effects occurred, although a mild increase in ventricular arrhythmias was associated with milrinone therapy. Survival vs mortality was not an endpoint in this study.

Following median short-term infusion (75 µg/kg at a rate of 100 µg/second), intravenous milrinone produced acute hemodynamic improvement in all of 20 patients with severe CHF, decreasing left ventricular end-diastolic pressure (from 27 to 18 mmHg), pulmonary wedge pressure, right atrial pressure and systemic vascular resistance (Baim et al., 1983). Increases in cardiac index (from 1.9 to 2.9 L/min/m (2)) and the peak positive first derivative of left ventricular pressure were observed. Slight increases were also observed in heart rate, and a slight reduction in mean arterial pressure was noted. Beneficial hemodynamic effects were sustained throughout a subsequent 24-hour continuous infusion (0.25 to 1 µg/kg/min; median dose 0.33 µg/kg/min), suggesting no development of tolerance during this time period. Nineteen patients were given oral milrinone therapy (average dose, 29 mg daily) for up to 11 months (mean 6 months) resulting in sustained improvement of CHF symptoms. No evidence of fever, thrombocytopenia, or gastrointestinal toxicity was seen in the patients. This included one patient who had developed fever and thrombocytopenia on previous oral aminone therapy. In 10 patients who received the drug for 6 months or longer, continued responsiveness was observed, as evidenced by a 27% increase in left ventricular ejection fraction (by radionuclide ventriculography) following a 7.5 mg oral dose (Baim et al., 1983).

Combination Therapy

The results of a retrospective review suggest that use of intravenous milrinone in combination with an oral beta-blocker may improve the prognosis of patients with severe CHF. In patients with severe CHF (NYHA functional class IV; ejection fraction less than 25%) refractory to oral therapy (ie, digitalis, diuretics, ACE inhibitors), use of loW-dose milrinone (0.375 to 0.45 µg/kWminute) can allow for initiation and up-titration of oral beta-blocker therapy, improvement in NYHA functional class (from IV to II or III), improved survival, reduction in hospitalization, and eventual weaning from milrinone therapy. Milrinone and beta-blockers appear to work synergistically to improve cardiac function in patients with severe CHF and betablockade appears to prevent milrinone-associated QTc interval prolongation (Zewail et al., 2003).

Low Cardiac Output after Cardiac Surgery (Adult)

Milrinone, during short-term therapy, is effective for increasing cardiac index in patients with low cardiac output after cardiac surgery. A significant increase in cardiac index and a fall in pulmonary capillary wedge pressure occurs with infusions during the first 48 hours; however, long-term (mean of 6 months) therapy has induced a greater incidence of morbidity and mortality (Das et al., 1994; Copp et al., 1992; Wright et al., 1992).

Milrinone increased blood flow through newly anastomosed internal mammary artery (IMA) used for coronary artery bypass grafting (CABG). In 20 patients undergoing CABG surgery, the left IMA was dissected and grafted to the distal left anterior descending artery. After weaning from cardiopulmonary bypass, patients were given either milrinone 50 µg/kg, over 10 minutes, or an infusion of epinephrine 0.03 µg/kg/minute. Ten minutes after completion of drug administration, IMA flow was measured and compared to that before drug delivery. Flow increased by 24% in milrinone-treated patients (p less than 0.05 compared to baseline) and was unchanged in those receiving epinephrine. Arterial pressure was significantly lower after milrinone infusion than after epinephrine infusion (p less than 0.05). Milrinone was recommended as a firstline inotrope after CABG surgery (Lobato et al., 2000).

Low Cardiac Output after Cardiac Surgery (Paediatric)

Results of a randomized, double-blind, placebo controlled trial of 238 pediatric patients at high risk for developing low cardiac output syndrome (LCOS) (aged 2 days to 6.9 years) showed that prophylactic use of high-dose milrinone immediately after congenital heart surgery (biventricular repair) reduced the relative risk of developing LCOS by 55% in all patients (p=0.023) and by 64% in 227 patients without protocol violations (p=0.007). Patients were randomized within 90 minutes of arriving to the intensive care unit after surgery into one of three groups: high-dose intravenous (IV) milrinone (60-minute bolus of 75 µg/kg, then 0.75 µg/kg/minute (min) infusion for 35 hours); low-dose IV milrinone (60-minute bolus of 25 µg/kg, then 0.25 µg/kg/min for 35 hours); or placebo. Within 36 hours of receiving the study medication, 9.6% of the high-dose milrinone group developed LCOS (clinical symptoms of tachycardia, oliguria, poor perfusion, or cardiac arrest) requiring additional pharmacotherapy or mechanical support compared to 26.7% in the placebo group (RRR=64%, p=0.007). Although 17.7% of patients in the low-dose milrinone group developed LCOS compared to placebo (RRR=34%, p=0.183), this was not statistically significant. Duration of mechanical ventilation and hospital stay were similar in all groups (p=0.964 and p=0.159, respectively).

Prolonged hospital stays (longer than 15 days) occurred in 13.5% of patients in the high-dose milrinone group, 8.2% in the low-dose milrinone group, and 23.3% of the placebo group (p=0.038). The mean urine output and creatinine clearance were not significantly different between groups: 2.7 milliliters (mL)/kg/hour (hr) and 62.4 mL/min in the high-dose group, 2.9 mL/kg/hr and 66.4 mL/min in the low-dose group, and 2.6 mL/kg/hr and 63.7 mL/min in the placebo group, with neonates having the lowest mean creatinine clearance (37.2 mL/min) compared to children aged 4.8 months to 6 years (84.5 mL/min).

Adverse events commonly reported by adults taking milrinone (arrhythmias, hypotension, and thrombocytopenia) were rare in this pediatric population, with no difference in incidence between milrinone and placebo groups (Hoffman et al., 2003).

Intravenous milrinone produced a mean 12% decrease in blood pressure and an 18% increase in cardiac index in pediatric patients (ages 3 to 22 months; n=20) with low cardiac output after surgical repair of congenital heart defects (p less than 0.05, both values). These cardiovascular effects were associated with an average peak plasma concentration of 235 ng/mL. The investigators recommend a loading dose of 50 µg/kg administered progressively in 5 minutes (after separation from cardiopulmonary bypass), followed by an infusion of approximately 3 µg/kg/min for 30 minutes, and thereafter, a maintenance infusion of 0.5 µg/kg/minute (Bailey et al., 1999).

Milrinone, during short-term therapy, is effective for increasing cardiac index in neonates with low cardiac output following cardiac surgery. In a prospective cohort study involving 10 neonates (ages 3 to 27 days) with low cardiac output after cardiac surgery, patients were administered an intravenous loading dose of 50 µg/kg over 15 minutes followed by a continuous infusion at 0.5 µg/kg/min for 30 minutes. In addition to increasing cardiac index, administration of milrinone decreased filling pressures, systemic and pulmonary arterial pressures, and systemic and pulmonary vascular resistances. Mean heart rate increased after the loading dose, but slowed during the infusion. Milrinone increased heart rate without altering myocardial oxygen consumption (Chang et al., 1995).

Weaning from Cardiopulmonary Bypass

Numerous studies have shown that milrinone is effective for patients being weaned after cardiopulmonary bypass surgery (Lobato et al., 2000; Doolan et al., 1997; Kikurai et al., 1997; De Hert et al., 1995; Butterworth et al., 1995).

Milrinone proved efficacious in weaning high risk patients from cardiopulmonary bypass after cardiac surgery (mostly coronary artery bypass grafting). In a double-blind study (Doolan et al., 1997), 30 patients with left ventricular dysfunction and/or pulmonary hypertension were randomized to milrinone (n=15) or placebo (n=15). Milrinone (or placebo) was initiated approximately 15 minutes before the withdrawal of cardiopulmonary bypass with a loading dose of 50 µg/kg over 20 minutes followed by a continuous infusion of 0.5 µg/kg/minute continuing for a minimum of 4 hours. In the milrinone group, all patients were successfully weaned compared with 5 of 15 in the placebo group (p 0.0002). Of the 10 who failed weaning, 4 experienced an increase in mean pulmonary capillary wedge pressure greater than 22 mm Hg for at least 5 minutes; 4 had a greater than 10% decrease in blood pressure from baseline due to cardiac dilatation; and 2 had a reduction in blood pressure greater than 20% from baseline. Milrinone-treated patients had a significantly greater increase in cardiac index than controls (p less than 0.001).

Those who failed to be weaned were subsequently switched to open-label milrinone and were successfully weaned. Ventricular tachycardia of 1 minute duration occurred in a milrinone patient 3 days postoperatively (neither cardioversion or pharmacotherapy were required); no significant adverse effects were associated with milrinone use.

Milrinone improved hemodynamics and cardiac function in patients treated immediately after being weaned from cardiopulmonary bypass (CPB) with catecholamines (Kikura et al., 1997). In an open label study, 37 patients having cardiac surgery requiring CPB were randomized to one of the following treatments immediately after being weaned from CPB with the use of norepinephrine, epinephrine, and/or nitroglycerin: control group (no treatment) (n=10); milrinone 50 mg/kg bolus only (n=8); 50 µg/kg bolus plus 0.5 µg/kg/minute (n=10); or 75 µg/kg bolus plus 0.75 µg/kg/minute (n=9). Bolus doses of milrinone were given over 3 minutes. Catecholamine infusions were maintained at a constant rate during the 10-minute study period, and baseline preload was kept constant by volume transfusion from the CPB reservoir. Based on hemodynamic measurements taken at baseline (immediately after weaning from CPB), and at 3, 5, and 10 minutes, cardiac index (CI) and stroke volume index (SVI) increased significantly in all milrinone groups, but not in the control group, with a significant difference between all milrinone groups and controls in CI at 5 and 10 minutes, and in SVI at 10 minutes. No significant differences were observed among the milrinone groups. Echocardiography revealed circumferential fiber shortening increased significantly from baseline in the milrinone groups, but no changes occurred in the control group. Heart rate and mean arterial pressure were not significantly altered in any group. Milrinone improved hemodynamics and cardiac function when given either as a bolus, or as bolus plus infusion, immediately after CPB when preload was kept constant.

Chronic Low Cardiac Output Syndrome

There is evidence to show that treatment with milrinone is effective for increasing cardiac function and for replacing conventional cardiovascular support prior to heart transplantation. Milrinone is effective in lowering pulmonary hypertension and as a diagnostic measure of pulmonary vascular reactivity in patients being evaluated for heart transplantation. Furthermore, short-term and extended-duration milrinone has bridged in-patients with severe heart failure to high-dose oral vasodilator therapy, bringing clinical improvement and delayed need for heart transplantation, as well as survival to transplantation.

A retrospective case review of in-patients with advanced HF suggests that long-term intravenous milrinone is tolerable and enables initiation or up-titration of angiotensin-converting enzyme (ACE) inhibitors and vasodilators without development of detrimental hypotension. Included in the study were 63 NYHA class III/IV patients with mean ejection fraction of 17%. Overall, 58 patients received a milrinone loading dose of 50 µg/kg; mean maintenance dose was 0.43 µg/kg/minute for a mean of 12 days (56 patients received the drug for greater than 48 hr and 28 for 7 days or more). Comparing baseline with 24 hours, mean values for pulmonary systolic and diastolic pressure and pulmonary capillary wedge pressure decreased significantly (p less than 0.0001), resulting in a significant increase in mean cardiac index (p less than 0.001). Systemic vascular resistance declined significantly (p less than 0.05). At 24 hr, significantly more patients were receiving ACE inhibitors than at baseline (p less than 0.01); and mean ACE inhibitor and hydralazine doses were significantly higher at the end of milrinone therapy than at 24 hr (p less than 0.01; p less than 0.03, respectively). The incidence of arrhythmias and clinically significant hypotension was minimal (Milfred-LaForest et al., 1999).

In patients with severe HF being considered for transplantation, short-term intravenous (IV) milrinone improved hemodynamics and facilitated the initiation of high-dose vasodilator therapy, producing symptom improvement, decreased hospitalization, increased survival, and decreased need for cardiac transplantation (Cusick et al., 1998). Fourteen patients (New York Heart Association class III (3) and IV (11)) were given a loading dose of milrinone 50 µg/kg followed by a maintenance infusion of 0.5 µg/kg/minute. If hemodynamic goals were not reached in 4 hours, another bolus (25 to 50 µg/kg) was given and the maintenance infusion rate was increased to 0.85 µg/kg/minute. Mean maximum dose to reach hemodynamic goals was 0.71 µg/kg/minute for an average duration of 50 hours; hemodynamic goals included cardiac index greater than 2.5 L/min/m(2), pulmonary capillary wedge pressure less than 16 mmHg, and systemic vascular resistance less than 1200 dynes/sec/cm(−5). Afterwards, all 14 patients were titrated to high-dose angiotensin-converting enzyme inhibitors (318% dose increase over baseline) and diuretics (89% dose increase over baseline). In some cases, hydralazine was added.

High-dose vasodilator therapy enabled 10 of 14 patients to experience hemodynamic and symptomatic improvement, fewer re-hospitalizations, decreased need for cardiac transplantation, and 12-month survival.

Intravenous milrinone is safe when, used long-term to bridge patients with advanced HF to transplantation (Mehra et al., 1997). Patients in this study were dependent on inotropic therapy (failure to wean on 2 attempts) and all were administered dopamine in addition to milrinone and dobutamine. Eighteen patients were initially stabilized on milrinone with dobutamine added later and 31 were initially stabilized on dobutamine with milrinone added later. Some patients received milrinone for as long as 8 weeks. Hypotension occurred in 5 patients; of these, 4 had renal insufficiency and in one, the adverse effect was thought to be due to a dosing error. Three cases of thrombocytopenia included 2 patients in whom thrombocytopenia was attributed to heparin use and the third did not improve when milrinone was withdrawn. These investigators concluded that milrinone is safe and effective therapeutic support for advanced HF patients awaiting transplantation.

Another study (n=29), with milrinone alone or with milrinone followed by dobutamine or dopamine, if needed, also concluded that long-term milrinone treatment is effective for bridging CHF patients to transplantation. All patients were treated until heart transplantation—a period ranging from 3 to 160 days (average 40 days) (Canver et al., 2000).

Milrinone was found to be effective in lowering pulmonary hypertension and as a diagnostic measure of pulmonary vascular reactivity in patients being evaluated for heart transplantation. A single intravenous bolus of milrinone (50 mg/kg body weight) was infused over 1 minute in 27 patients with New York Heart Association functional class III or IV HF and pulmonary vascular resistance of 200, dynes/s/cm or more referred for heart transplantation. Milrinone decreased pulmonary vascular resistance by a mean 31% at 5 minutes; response occurred maximally 5 to 10 minutes after administration and lasted at least 20 minutes. Effects included an increase in cardiac output, decreases in mean pulmonary arterial pressure and pulmonary artery wedge pressure, and no change in transpulmonary pressure gradient, heart rate, or systemic arterial pressure. Milrinone is a rapid, well-tolerated pharmacologic agent to test for reversibility of pulmonary hypertension in heart transplant candidates (Givertz et al., 1996).

Milrinone was recommended as an effective pharmacologic agent for pulmonary hypertension reversibility assessment in patients with CHF considered to be candidates for cardiac transplantation (Pamboukian et al., 1999). At 15 minutes post-dosing, milrinone 50 mg/kg by bolus produced significant decreases in pulmonary vascular resistance (3.9 to 2.5 Wood units), in mean pulmonary artery pressure (35 to 28 mmHg), and in pulmonary capillary wedge pressure (20 to 15 mmHg) (p=0.002, 0.002, and 0.006, respectively). Cardiac output increased significantly (4.0 to 5.1 L/min; p=0.001). The patients with the most severe pulmonary hypertension had the most pronounced improvements. Of the 19 patients evaluated, 6 received cardiac transplantation, and no deaths were reported among that group.

The utility of treatment with milrinone formulated for IV administration has been demonstrated by years of clinical practise in patients with HF. Whilst an oral formulation of milrinone was recommended for approval for therapeutic intervention of CHF in symptomatic patients, this formulation was eventually withdrawn due to high mortality rates observed during a trial (Packer, et al., 1991, The PROMISE Study). Other formulations such as those described in U.S. Pat. No. 4,806,361, directed to a sustained release formulation using an inert particulate core and U.S. Pat. No. 5,213,811, have similarly not been developed; this may be because of the controversy caused by the PROMISE study or because these formulations failed to provide the required patient exposure to therapeutic agent.

Administration of IV milrinone generally requires the patient to be admitted to a hospital, with a significant increase in cost of patient care; there is also a significant risk of bacterial infection. Whilst it is possible to allow patients to return home and continue with IV milrinone, in practise this is a complex undertaking and the risk of infection remains significant. There is at present no available oral formulation that provides the patient exposure to milrinone that is equivalent to the patient exposure that is achieved by the recommended administration of the IV formulation of milrinone. Such a formulation would overcome the limitations of IV administration, allowing patients to be treated at home. This would significantly reduce the cost of health care and provide a considerable benefit in terms of quality of life to patients with HF.

An aging population combined with life style choices is resulting in an ever increasing incidence of HF amongst the population. Not only will this significantly reduce the quality of life for patients but the burden on hospitalization infrastructure and cost of health care will severely impact on the ability to provide adequate health services to the community. There is a need, therefore, to provide a safe and effective means to treat asymptomatic and symptomatic patients for HF by oral dosage that mimics a plasma infusion profile, which may be easily administered in a non-hospital setting.

SUMMARY OF THE INVENTION

In a first aspect, the present invention provides an oral controlled-release formulation comprising:

(i) a core comprising a 5-(pyridinyl)-2-(1H)-pyridinone compound of formula (I):

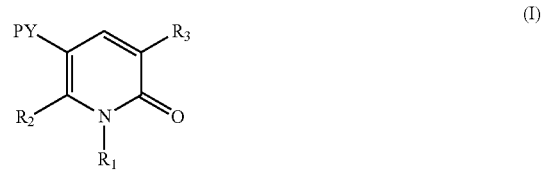

wherein $R_1$ is hydrogen, —$C_1$-$C_6$alkyl or —$C_1$-$C_6$alkyl-OH;

$R_2$ is —$C_1$-$C_6$alkyl;

$R_3$ is hydrogen, —$NH_2$, —CN, —C(O)$NH_2$, halo, —NH($C_1$-$C_6$alkyl), —N($C_1$-$C_6$alkyl)$_2$, —NH(COC$_1$-$C_6$alkyl), —$CO_2$H or —$CO_2C_1$-$C_6$alkyl; and PY is 4-, 3- or 2-pyridinyl optionally substituted with one or two $C_1$-$C_6$alkyl groups;

or a pharmaceutically acceptable salt thereof; one or more polymers and one or more pharmaceutically acceptable excipients; and (ii) a sustained-release coating;

wherein the formulation permits release of the compound of formula (I) in an amount to achieve steady state plasma levels effective to ameliorate symptoms of heart failure; wherein the release of the compound of formula (I) from the formulation is in the range of between 0.1 µg/kg body weight/minute to 20 µg/kg body weight/minute.

In one embodiment, the core comprises a compound of formula (I), hydroxypropylmethylcellulose or hydroxypropylcellulose having a viscosity of 80,000 to 120,000 cps, hydroxypropylmethylcellulose having a viscosity of about 50 cps and at least one pharmaceutically acceptable excipient; wherein the hydroxypropylmethylcellulose or hydroxypropylcellulose (80,000 to 120,000 cps) and the hydroxypropylmethylcellulose (50 cps) are in a ratio of 2:1 to 1:2, and the ratio of compound of formula (I) to total hydroxypropylmethylcellulose or hydroxypropylmethylcellulose and hydroxypropylcellulose is 1:2 to 1:6.

In another embodiment the core comprises a compound of formula (I), a hydrophilic matrix comprising at least two natural gums, and at least one pharmaceutically acceptable excipient; wherein the two natural gums are in a ratio of 2:1 to 1:2; and the ratio of the compound of formula (I) to the hydrophilic matrix is 1:1 to 1:2.5.

In yet another embodiment the core comprises (i) a coating composition comprising a compound of formula (I), one or more polymers, and one or more excipients, and (ii) inert spherical particles; wherein the coating composition is on coated on the surface of the spherical particles; wherein the ratio of compound of formula (I) to the spherical particles is about 1:5 to 1:25; and wherein the coated particles further comprise a seal coating.

In one embodiment, the sustained-release coating comprises a cellulose derivative, a co-polymer of acrylic acid, methacrylic acid or their esters.

In one embodiment of the invention the compound of formula (I) is 1,2-dihydro-3-cyano-6-methyl-5-(4-pyridinyl)-2(1H)-pyridinone (milrinone).

In yet a further embodiment, there is provided a method for treating a subject with heart failure or a stage, class or manifestation of heart failure or at risk of developing or exhibiting symptoms of heart failure, said method comprising administering to the subject, an oral controlled-release formulation according to the invention.

In a particular embodiment, the method provides a plasma concentration of the compound of formula (I) in the range of 100 to 400 ng/mL. The plasma concentration may be monitored and the dosage adjusted to provide a plasma concentration in this range.

In a further embodiment, there is provided a method of treating pulmonary hypertension in a subject, said method comprising administering to the subject, an oral controlled-release formulation according to the invention.

DETAILED DESCRIPTION OF THE INVENTION

Figure 1:
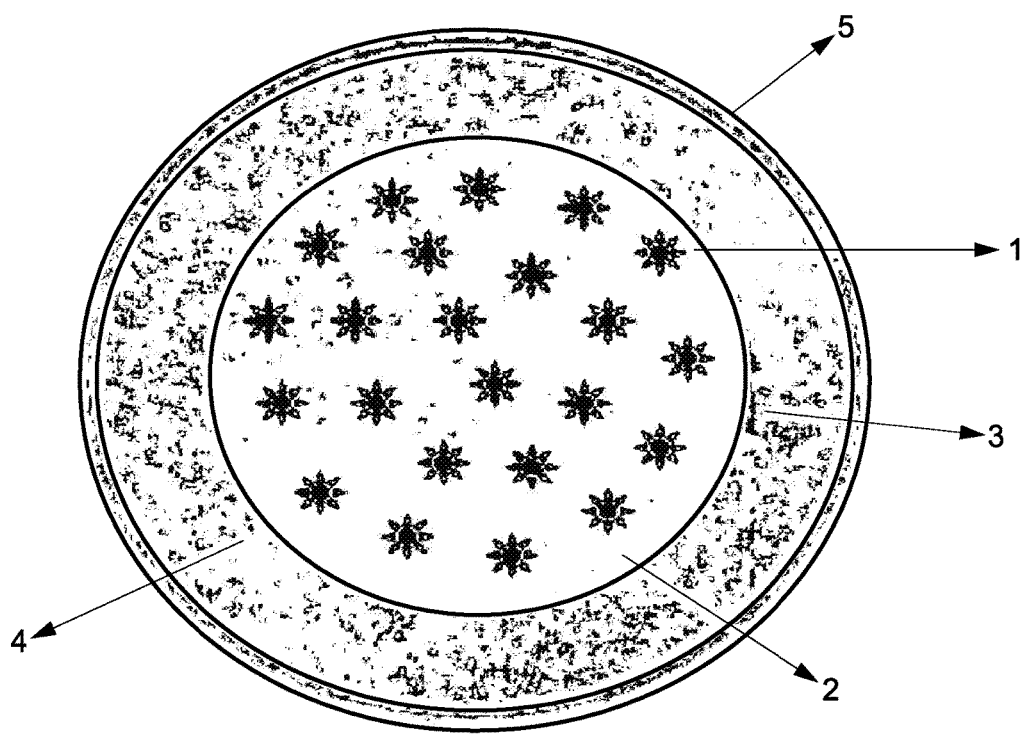
FIG. 1 is a schematic diagram showing an exemplary zero-order release formulation of the invention which is a combination of reservoir and matrix systems wherein 1 is drug. 2 is polymer matrix, 3 is a seal coating, 4 is a Sustained release coating and 5 is an enteric coating.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

As used in the subject specification, the singular forms "a", "an" and "the" include plural aspects unless the context clearly dictates otherwise.

As used herein, the term "about" refers to a quantity, level, concentration, value, dimension, size, or amount that varies by as much as 30%, 20%, or 10% or even as much as 9%, 8%, 7%, 6%, 5%, 4%, 3%, 2% or 1% to a reference quantity, level, concentration, value, dimension, size, or amount.

The present invention is predicated in part on the determination that a compound of formula (I) can be orally administered to a Subject with or at risk of developing or exhibiting HF or a symptom attributed to HF in a safe and effective manner to treat the manifestations of HF when administered to achieve a steady state plasma level of the compound of formula (I) that is comparable to intravenous infusion of a compound of formula (I) in the range of between 0.1 ug/kg body weight to 20 ug/kg body weight per minute.

The present invention in one aspect therefore provides an oral controlled-release formulation comprising:

(i) A core comprising a 5-(pyridinyl)-2-(1H)-pyridinone compound of formula (I):

wherein $R_1$ is hydrogen, —$C_1$-$C_6$alkyl or —$C_1$-$C_6$alkyl-OH;

$R_2$ is —$C_1$-$C_6$alkyl;

$R_3$ is hydrogen, —$NH_2$, —CN, —C(O)$NH_2$, halo, —NH($C_1$-$C_6$alkyl), —N($C_1$-$C_6$alkyl)$_2$, —NH(COC$_1$-$C_6$alkyl), $CO_2$H or —$CO_2C_1$-$C_6$alkyl; and PY is 4-, 3- or 2-pyridinyl optionally substituted with one or two $C_1$-$C_6$alkyl groups;

or a pharmaceutically acceptable salt thereof;

one or more polymers and one or more pharmaceutically acceptable excipients; and (ii) a sustained-release coating;

the formulation permits release of wherein the compound of formula (I) in an amount to achieve steady state plasma levels effective to ameliorate symptoms of heart failure;

wherein the release of the compound of formula (I) from the formulation is in the range of between 0.1 μg/kg body weight/minute to 20 μg/kg body weight/minute.

In some embodiments, in the compound of formula (I), at least one of the following applies: $R_1$ is selected from hydrogen, —$C_1$-$C_3$alkyl or —$C_1$-$C_3$alkylOH, especially hydrogen, —$CH_3$ or —$CH_2$OH, more especially hydrogen; $R_2$ is selected from —$C_1$-$C_3$alkyl, especially methyl or ethyl, more especially methyl; $R_3$ is selected from —CN (cyano), —$NH_2$, halo, —NH($C_1$-$C_3$alkyl), —N($C_1$-$C_3$alkyl)$_2$, —$CO_2$H or —$CO_2C_{1-3}$alkyl, especially —CN, —$NH_2$, —$CO_2$H and —$CO_2CH_3$, more especially —CN; and PY is unsubstituted 4-, 3- or 2-pyridinyl, especially unsubstituted 4-pyridinyl.

In a particular embodiment, the compound of formula (I) is 1,2-dihydro-3-cyano-6-methyl-5-(4-pyridinyl)-2(1H)-pyridinone. This compound is also known as 2-methyl-6-oxo-dihydro-3,4'-bipyridine-5-carbonitrile and milrinone.

Methods of making compounds of formula (I) including milrinone are known in the art and can be found, for example, in GB Patent No. 2065642 and U.S. Pat. No. 4,313,951.

As used herein, the term "alkyl" refers to a straight chain or branched saturated hydrocarbon group having 1 to 6 carbon atoms. Where appropriate, the alkyl group may have a specified number of carbon atoms, for example, $C_{1-6}$alkyl which includes alkyl groups having 1, 2, 3, 4, 5 or 6 carbon atoms in a linear or branched arrangement. Examples of suitable alkyl groups include, but are not limited to, methyl, ethyl, n-propyl, i-propyl, n-butyl, i-butyl, t-butyl, n-pentyl, 2-methylbutyl, 3-methylbutyl, 4-methylbutyl, n-hexyl, 2-methylpentyl, 3-methylpentyl, 4-methylpentyl, 5-methylpentyl, 2-ethylbutyl and 3-ethylbutyl.

As used herein, the term "halogen" or "halo" refers to fluorine (fluoro), chlorine (chloro), bromine (bromo) and iodine (iodo).

As used herein, the term "pyridine" or "pyridinyl" refers to a 6-membered aromatic cyclic group having one nitrogen atom in the ring having the formula:

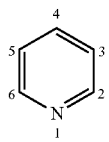

The pyridine ring may be attached to the structure of formula (I) where indicated with the PY at any of the carbon atoms at the 2-, 3- or 4-position.

The compounds of formula (I) may be in the form of pharmaceutically acceptable salts. It will be appreciated however that non-pharmaceutically acceptable salts also fall within the scope of the invention since these may be useful as intermediates in the preparation of pharmaceutically acceptable salts or may be useful during storage or transport. Suitable pharmaceutically acceptable salts include, but are not limited to, salts of pharmaceutically acceptable inorganic acids such as hydrochloric, sulphuric, phosphoric, nitric, carbonic, boric, sulfamic and hydrobromic acids, or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulphonic, toluenesulphonic, benzenesulphonic, salicylic, sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium.

Basic nitrogen-containing groups may be quaternised with such agents as lower alkyl halide, such as methyl, ethyl, propyl and butyl chlorides, bromides and iodides, dialkyl sulfates like dimethyl and diethylsulfate, and others.

Conveniently the compound of formula (I) is formulated with at least one polymer and pharmaceutically acceptable excipients and optionally includes at least one film coating that assists with sustained release of the compound.

The objective of a standard controlled-release formulation is to provide zero order kinetics of drug delivery (i.e. a linear delivery with respect to time). Controlled-release of drug from a dosage then relies upon two processes: dissolution and release.

The compound of formula (I) may be blended with one or more polymers, to provide a matrix that is either formed into a particle (small or large), or is coated on an inert particle to form the core of the formulation. The polymers of the core are selected from hydrophilic, hydrophobic or plastic. Hydrophilic polymers are water soluble and hydrate in contact with water to form a hydrogel as they dissolve and swell; hydrophobic polymers do not dissolve but may be subject to erosion as the matrix releases soluble constituents; plastic polymers form insoluble or skeletal matrices but do not erode. Upon exposure to the fluid in the stomach, small intestine and colon, hydrophilic polymers hydrate and form a hydrogel that acts as a diffusion barrier to drug release; hydrophobic polymers release drug through diffusion through pores and through erosion. Drug release from plastic matrices is controlled by the rate of liquid penetration and is accelerated by the presence of channel forming agents: soluble components that are added in addition to drug.

The behaviour of some polymers is dependent upon pH. This is particularly true where the polymer contains acidic or basic moieties as pH will affect the ionization state. Ionization can transform a polymer from hydrophobic to hydrophilic, with an accompanying transformation in release properties.

The release of the dissolved compound of formula (I) into, for example, the gastrointestinal (GI) tract may also be controlled by the coating on the particle. This coating is typically a polymer or blend of polymers that is relatively stable towards the conditions encountered in the gut. In many cases, the coating includes at least one hydrophilic polymer that will swell on contact with fluid in the gut to form a hydrogel barrier that is homogenous and stable to changes that may take place to the underlying matrix. The hydrogel also assists with slow release of dissolved compound of formula (I). The properties of the surface coating can be pH dependant depending upon the presence of acidic or basic moieties in the polymer constituents.

A particular disadvantage of some controlled-release formulations is the potential for a burst release of drug to occur immediately following contact of the dosage form with the dissolution fluid. The use of a hydrophilic polymer in the film coating or in the matrix, wherein the hydrophilic polymer forms a hydrogel rapidly after hydration, can significantly reduce the incidence of the burst release phenomenon.

Controlled-release oral formulations include a monolithic tablet dosage form in which one or more drug-polymer matrices provide the core and or particulate or bead dosage forms in which an inert particle coated with drug provides the core. These types of formulations may include an optional surface film coating to provide additional control over drug release. Particulate dosage forms may be formed into a tablet or filled into a capsule. This differs from immediate release (IR) formulations which are designed to disintegrate, dissolve promptly and release a bolus dose of drug.

The core matrix containing the compound of formula (I) may be formed by granulation or direct compression and may be heterogeneous to provide porosity.

In particular, a core matrix may comprise either or both hydrophilic polymers and hydrophobic polymers in order to achieve the appropriate release profile. Further, one or more of the polymers may swell upon hydration in a manner that may additionally be dependent upon pH, to form a hydrogel that is viscous and gelatinous and thus provides a barrier to drug release. The composition of hydrogel determines its properties, which can thus be manipulated in order to achieve appropriate drug release kinetics.

The optional surface film coating provides a diffusion release mechanism where the permeability is often directly related to hydration leading to polymer swelling and the installation of hydrogel dynamics.

At least one combination of matrix and optional surface film coating provided in the description below can be used in the formulation of the invention to achieve the desired release profile across the different environments encountered during transit through the GI tract.

Polymers that are of use in the formation of core drug-polymer matrices are as follows:

Acrylic and methacrylic polymers including hydroxypropyl methacrylates (HPMA) and hydroxyethyl methacrylates (HEMA), as well as N-isopropyl acrylamides;

Polyethylene oxides (PEO) also known as polyethylene glycols (PEG) and polypropylene oxides (PPO), as well as block copolymers of PEO and PPO (also known as Pluronics (Registered Trade Mark));

Cellulose ethers including hydroxypropyl methylcellulose (HPMC), hydroxypropylcellulose (HPC), hydroxyethyl cellulose (HEC), methylcellulose (MC), ethyl cellulose (EC) and carboxymethylcellulose (CMC);

Polylactides (PLA), polyglucolides (PGA), copolymers of polylactide and polyglucolide in various proportions (PLGA);

Poly(sucrose acrylates);

Polylysine, polyvinylamine, polyethylimine (PEI), polyglutamic acid, polyvinyl alcohol (PVA); copolymers of ethylene and vinyl acetate (pEVA);

Polyethyleneglycol terephthalate, polybutylene terephthalate and copolymers thereof (also known as Locteron [Registered Trade Mark]); Copolymers of PEG and PLGA also known as Re-Gel (Registered Trade Mark); Polyorthoesters also known as Chronomer (Registered Trade Mark); polyanhydrides; copolymers of acrylic acids and esters, or methacrylic acids and esters of various molecular weight and proportion also known as Eudragit (Registered Trade Mark) in particular RL30D, RLPO, RL100, RS30D, RSPO, RS100, NE30D, NM30D, NE40D, L100; copolymers of phthalic acid cellulose and phthalic ester cellulose also known as CAP (Registered Trade Mark);

Polyvinylpyrrolidone also known as Kollidon (Registered Trade Mark) and, copolymers thereof with polyvinyl acetate also known as Kollidon SR (Registered Trade Mark);

Polymers of natural origin including non-ionic, amino, carboxylated and sulfated polysaccharides, optionally chemically modified through partial hydrolysis and/or conjugation of modifiers such as carboxylates or long chain fatty acids (C8-C16), include:

Guar gum; acacia gum, tragacanth gum, xanthan gum, carrageenans (both iota and lambda), Linn gum, alginates, scleroglucans, dextrans, chitins and chitosans, pectins, galactomannans including locust bean gum.

In addition, it is frequently found that polymer blends are particularly useful for providing the appropriate release profiles for controlled-release formulations, for example mixing polymers with hydrophilic and hydrophobic properties, and such polymer blends would include:

Methyl methacrylates polymers with starch or cellulose polymers;

Polyacrylic acid-Pluronic-polyacrylic acid block copolymers;

Multilayer polyelectrolytes using cationic polymers selected from chitosan, polylysine, polyallylamine or polyvinylamine with anionic polymers selected from Carbopols including 971NF, carrageenan, xanthan gum, alginate, hyaluronic acids, Eudragit® including L100 and carboxymethylcellulose;

Hydrophobic cellulose polymers such as ethylcellulose or Compritol 888 ATO are often mixed with hydrophilic polymers such as HPMC, NaCMC, sodium alginate, xanthan gum or Methocel (Registered Trade Mark);

Hydrophilic swelling polymer such as HPMC is mixed with a pH dependant polymer such as Eudragit (Registered Trade Mark) L100-55;

Polymer blends may be crosslinked either by covalent bonds or, particularly for polymers of natural origin, through the addition of polyvalent cations including borate, calcium, magnesium and zinc;

Natural gums are often used in polymer blends, in particular carrageenans with cellulose ethers, xanthan gum with locust bean gum.

Whilst ternary blends are less common, one example is a blend of non-ionic water soluble polymer Polyox with a swellable high molecular weight crosslinked acrylic polymer Carbopol and lactose.

Film coatings are contemplated for use with multi-unit dosage forms other than monolithic tablets. Coatings are selected which include polymer, solvent and a plasticizer, particularly triethyl citrate, dibutyl sebacate, diethyl phthalate or propylene glycol. Plasticizers may not be necessary when poly(dimethylsiloxane) or other silane elastomers are used.

Particular examples of surface coatings which can provide a hydrogel barrier upon hydration include the cellulose polymers, Eudragit (Registered Trade Mark) polymers and graft copolymers of polyvinyl acetate, polyvinyl alcohol and PEG, also known as Kollicoat (Registered Trade Mark), for example Kollicoat (Registered Trade Mark) SR and Kollicoat (Registered Trade Mark) IR, used with propyleneglycol as plasticizer. The properties of this coating are independent of pH.

Polyelectrolyte multilayers (PEM) are one particular example of a film coating which can provide an appropriate rate of drug release through a combination of variables including:

The selection of positive and negatively charged polyelectrolytes;

The number of layers that are deposited;

The molecular weight of the polyelectrolytes used to form the film.

The permeability of PEMs can be responsive to stimuli whereby a change in pH, ionic strength or temperature has the potential to change the permeability to particular solutes.

Multilayer tablet formulations are particularly useful for highly soluble drugs. Such dosage forms include a hydrophilic matrix core with one or two semipermeable coatings, which may be implemented as a film or compressed barrier.

Typical polymers include cellulose derivatives particularly HPMC, NaCMC, HPC, EC or MC, or natural gums particularly tragacanth or guar gum.

In one embodiment, the core of the formulation comprises a compound of formula (I), hydroxypropylmethylcellulose or hydroxypropylcellulose having a viscosity of 80,000 to 120,000 cps hydroxypropylmethylcellulose having a viscosity of about 50 cps and at least one pharmaceutically acceptable excipient; wherein the hydroxypropylmethylcellulose or hydroxypropylcellulose (80,000 to 120,000) and the hydroxypropylmethylcellulose (50 cps) are in a ratio of 2:1 to 1:2, and the ratio of compound of formula (I) to total hydroxypropylmethylcellulose or hydroxypropylcellulose and hydroxypropylmethylcellulose is 1:2 to 1:6.

Hydroxypropylmethylcellulose, also known as hypromellose or HPMC, is available in different viscosities. In the present invention, the hydroxypropylmethylcellulose is present in two viscosities, 80,000 to 120,000 cps and about 50 cps. A suitable HPMC having a viscosity of 80,000 to 120,000 is hypromellose 2208 USP which comprises 19-24% methoxy ether substitution and 7-12% hydroxypropyloxy ether substitution on glucose C2, C3 and C6 hydroxyl moieties and has a viscosity of about 100,000 cps. The viscosity is measured at 2% concentration in water at 20° C. A suitable HPMC (80,000 to 120,000) is HPMC K100M. A suitable HPMC having a viscosity of about 50 cps is HPMC E50 LV.

In some embodiments, the HPMC (80,000 to 120,000) may be substituted by hydroxypropylcellulose (HPC) having a viscosity of 80,000 to 120,000 cps.

In some embodiments, the HPMC or HPC (80,000 to 120,000) is HPMC (80,000 to 120,000), especially HPMC K100M.

In some embodiments, the HPMC (about 50 cps) is HPMC E50 LV.

In some embodiments the ratio of HPMC or HPC (80,000 to 120,000) to HPMC (about 50 cps) is in the range of 1.5:1 to 1:1.5, especially about 1:1.

In some embodiments, the ratio of compound of formula (I) to total HPMC or HPMC or HPC (80,000 to 120,000) and HPMC (about 50 cps), is 1:2 to 1:6, especially about 1:3 to 1:5, more especially about 1:3.

In some embodiments the compound of formula (I) is present in an amount of 10 to 30% w/w of the core, especially 15 to 25% w/w of the core, more especially about 20% w/w of the core.

In some embodiments the HPMC or HPC (80,000 to 120,000) is present in an amount of 20 to 40% w/w of the core, especially 25 to 35% w/w of the core, more especially about 30% w/w of the core.

In some embodiments, the HPMC (about 50 cps) is present in an amount of 10 to 40% w/w of the core, especially 20 to 35% w/w or 25 to 35% w/w of the core, more especially about 30% w/w of the core.

In some embodiments the core also comprises pharmaceutically acceptable excipients such as binders and/or lubricants. Suitable binders include disaccharides such as sucrose and lactose, polysaccharides such as starches and cellulose derivatives, for example, microcrystalline cellulose, cellulose ethers and hydroxypropylcellulose (HPC), sugar alcohols such as xylitol, sorbitol or maltitol, proteins such as gelatine and synthetic polymers such as polyvinylpyrrolidone (PVP) and polyethylene glycol (PEG). In a particular embodiment, the binder is microcrystalline cellulose.

In some embodiments, the binder is present in an amount of 10 to 30% w/w of the core, especially about 15 to 25% w/w of the core, more especially about 18% w/w of the core. In some embodiments, the compound of formula (I) such as milrinone and the binder such as microcrystalline cellulose are together present in the core in about 30 to 50%, especially about 40% w/w of the core. In some embodiments, the ratio of compound of formula (I) to binder is 1:2 to 2:1, especially about 1:1.

Suitable lubricants include fats such as magnesium stearate, vegetable stearin and stearic acid, talc or silica. In particular embodiments, the lubricant is magnesium stearate.

In some embodiments, the lubricant is present in an amount of 0.5 to 5% w/w of the core, especially about 1 to 3% NON of the core, especially about 2% w/w of the core.

In another embodiment, the core of the formulation comprises a compound of formula (I), a hydrophilic matrix comprising at least two natural gums, and at least one pharmaceutically acceptable excipient; wherein the two natural gums are in a ratio of 2:1 to 1:2; and the ratio of the compound of formula (I) and the hydrophilic matrix is 1:1 to 1:2.5.

Suitable natural gums include guar gum, acacia gum, tragacanth gum, xanthan gum, carrageenans (both iota and lambda), Linn gum, alginates, scleroglucans, dextrans, chitans and chitosans, pectins, and galactomannans including locust bean gum. In some embodiments the hydrophilic matrix includes xanthan gum or locust bean gum. In a particular embodiment the hydrophilic matrix includes xanthan gum and locust bean gum.

In some embodiments, the ratio of xanthan gum to locust bean gum is about 1.5:1 to 1:1.5, especially about 1:1.

In some embodiments, the ratio of compound of formula (I) to hydrophilic matrix is 1:1 to 1:2, especially about 1:1.5.

In some embodiments, the compound of formula (I) is present in an amount of 15 to 25% w/w of the core, especially 18 to 22% w/w of the core, more especially about 20% w/w of the core.

In some embodiments, the hydrophilic matrix is present in an amount of 20 to 40% w/w of the core, especially 25 to 35% w/w of the core, more especially about 30% w/w of the core. For a ratio of 1:1 xanthan gum to locust bean gum, the amount of each gum will be about 15% w/w of the core.

In some embodiments, the excipients are selected from binders, fillers, glidants, lubricants and mixtures thereof.

Suitable binders include disaccharides such as sucrose and lactose, polysaccharides such as starches and cellulose derivatives such as microcrystalline cellulose, cellulose ethers and hydroxypropylcellulose (HPC), sugar alcohols such as xylitol, sorbitol or maltitol, proteins such as gelatine and synthetic polymers such as polyvinylpyrrolidone (PVP) and polyethylene glycol (PEG). In particular embodiment, the binder is microcrystalline cellulose, polyvinylpyrrolidone (PVP) or mixtures of microcrystalline cellulose and PVP.

In some embodiments the binder is present in an amount of 17 to 30% w/w of the core, more especially about 23.5% w/w of the core. In some embodiments the binder comprises about 20% w/w of microcrystalline cellulose and about 3.5% w/w PVP.

Suitable fillers or bulking agents include lactose, sucrose, glucose, mannitol, sorbitol, calcium carbonate and dibasic calcium phosphate. In a particular embodiment, the filler is lactose.

In some embodiments, the filler is present in the core in an amount of 20% w/w of the core, especially about 25% w/w of the core.

Suitable glidants include fumed silica, talc and magnesium carbonate. In a particular embodiment, the glidant is fumed silica.

In some embodiments the glidant is present in an amount of about 0.5 to 1.5% w/w of the core, especially about 1% w/w of the core.

Suitable lubricants include fats such as magnesium stearate, vegetable stearin and stearic acid, talc or silica. In particular embodiments, the lubricant is magnesium stearate.

In some embodiments the lubricant is, present in an amount of 0.25 to 1% w/w of the core, especially about 0.5% w/w of the core.

In another embodiment, the core of the formulation comprises (i) a coating composition comprising a compound of formula (I), one or more polymers, and one or more excipients, and (ii) inert spherical particles; wherein the coating composition is on coated on the surface of the spherical particles; wherein the ratio of compound of formula (I) to the spherical particles is about 1:5 to 1:25; and wherein the coated particles further comprise a sealing coating.

The inert spherical particles may be any inert spherical particles commonly used in microparticulate systems. Typically, the inert spherical particles have a diameter of 0.06 to 2 mm. Suitable inert spherical particles are sugar and/or starch spherical particles. Such particles are suitable for formulation into a capsule or tablet. Microparticle dosage systems can provide the following benefits for extended release formulations:
  Less dependent on gastric emptying, resulting in less intra/inter individual variability in gastric transit time (sizes less than 2 mm are able to continuously leave stomach even when pylorus is closed);
  Particles are better distributed, avoiding possibility of localized irritation;
  Drug safety is improved for modified release formulations, as less susceptible to performance failure if damaged;
  Multiparticulate formulations are popular for selective delivery to the colon when that is the only absorption window, they can also be used for continuous GI absorption. Furthermore it is possible to mix particles with different release profiles to optimise exposure in different regions of gut.

In some embodiments, the compound of formula (I) is prepared in a coating composition comprising a coating polymer and excipients such as binders. The coating composition is then coated onto the spherical particles.

Suitable coating compositions comprise, in addition to compound of formula (I), a polymer, plasticizer and binder. If required, the coating composition may be dissolved or suspended in a suitable solvent, such as water, for application. Suitable polymers include polyvinyl alcohol (PVA) or cellulose polymers such as HPMC, hydroxypropylcellulose (HPC), hydroxyethylcellulose (HEC), methylcellulose (MC), ethylcellulose (EC) and carboxymethylcellulose (CMC). Suitable plasticizers include propylene glycol, polyethylene glycol (PEG), dibutyl sebacate, glycerine, triethyl citrate and diethyl phthalate. In one particular embodiment, the polymer is HPMC and the plasticizer is PEG, for example, the coating composition sold under the trade mark OPADRY CLEAR (Registered Trade Mark). In another particular embodiment, the polymer is PVA and the plasticizer is PEG and/or glycerine, for example, the coating composition sold under the trade mark OPADRY II (Registered Trade Mark).

The coating composition may also comprise a binder. Suitable binders include disaccharides such as sucrose and lactose, polysaccharides such as starches and cellulose derivatives such as microcrystalline cellulose, cellulose ethers and hydroxypropylcellulose (HPC), sugar alcohols such as xylitol, sorbitol or maltitol, proteins such as gelatine and synthetic polymers such as polyvinylpyrrolidone (PVP) and polyethylene glycol (PEG). In a particular embodiment, the binder is PVP.

In some embodiments, the ratio of compound of formula (I) to the polymer/plasticiser blend is about 1.5:1 to 2:1, especially about 1.6:1 to 1.8:1.

In some embodiments, the ratio of compound of formula (I) to binder is in the range of 8:1 to 12:1, especially about 11:1.

In some embodiments, the ratio of compound of formula (I) to spherical particles is about 1:10 to 1:25, especially about 1:15 to 1:20.

Seal Coating/Buffer Coating

In some embodiments, the formulations of the invention may comprise a seal coating. The seal coating may be applied over the core, for example over the drug coating of the spherical particles or may be used as a coating on a tablet formed by compression of the core, also for example between layers of the formulation, such as between the core and the sustained-release coating (seal coat) or between the sustained-release coating and the enteric-release coating (buffer coat). The seal coating or buffer coating may comprise a polymer and a plasticizer. Suitable polymers include PVA and cellulose polymers such as HPMC, hydroxypropylcellulose (HPC), hydroxyethylcellulose (HEC), methylcellulose (MC), ethylcellulose (EC) and carboxymethylcellulose (CMC). Suitable plasticizers include propylene glycol, polyethylene glycol (PEG), dibutyl sebacate, glycerine, triethyl citrate and diethyl phthalate. In a particular embodiment, the polymer is HPMC and the plasticizer is PEG, for example, the coating composition sold under the trade mark OPADRY CLEAR (Registered Trade Mark). In another particular embodiment, the polymer is PVA and the plasticizer is PEG and/or glycerine, for example, the coating composition sold under the trade mark OPADRY II (Registered Trade Mark). The seal coating or buffer coating may also include a pigment to give a desired colour, for example, titanium dioxide to give white. The seal coating or buffer coating may be present in an amount of 3 to 15% w/w of the formulation, especially 5 to 12% w/w, more especially 5 to 10% w/w.

Sustained-Release Coating

The formulations above include a sustained-release coating. Suitable sustained-release coatings include cellulose derivative coatings such as HPMC, HPC, HEC, EC, MC and CMC or co-polymers of acrylic acids and their esters or methacrylic acids or their esters, such as those sold under the trade mark Eudragit® including RL30D, RLPO, RL100, RS30D, RSPO, RS100, NE30D, NE40D and L100. In particular embodiments, the sustained-release coating may comprise ethylcellulose (EC), which is insoluble in water, in which case, the sustained-release coating may optionally include a low content of water soluble polymer such as a low viscosity HPMC (eg: 6 cps), for example Opadry Clear™. In other embodiments, the sustained-release coating may comprise an acrylic acid, acrylic ester, methacrylic acid or methacrylic ester optionally including a low content of a methacrylic acid ester with quaternary ammonium groups (trimethylammoriioethyl methacrylate chloride) copolymer. This sustained-release coat may be comprised of one or more copolymers of ethyl acrylate (A), methyl methacrylates (B) and a low content of a methacrylic acid ester with quaternary ammonium groups (trimethylammonioethyl methacrylate chloride) (C). For the polymeric materials of this embodiment, the molar ratio of the monomers A:B are in the range 1:1-1:3 preferably 1:2; the molar ratio of the monomers A:C are in the range 1:0.01: to 1:0.5, preferably in the range 0.05-0.25. When one or more of the layers comprises a blend of two copolymers. The molar ratio of the monomers A:B:C in the first of the copolymers is approximately 1:2:0.2 and the molar ratio of the monomers A:B:C in the second of the copolymers is 1:2:0.1, and the ratio of the first and the second copolymer is in the range 1:5 to 1:15, especially about 1:9.

The sustained-release coatings may also comprise lubricants. The sustained-release coatings may also comprise plasticizers. The sustained-release coatings may also comprise anti-tacking agents.

In a particular embodiment, the sustained-release coating comprises ethyl cellulose as Aquacoat ECD 30 and HPMC 6 cps as Opadry Clear wherein the ratio of EC and HPMC is in the range 19:1 to 4:1 especially about 9:1.

In a particular embodiment, the sustained-release coating comprises ethyl cellulose as Aquacoat ECD 30 and HPMC 6 cps as Opadry Clear, and a plasticizer, wherein the ratio of EC and HPMC is in the range 19:1 to 4:1 especially about 9:1 and the ratio of EC to plasticizer is in the range 9:1 to 2:1 especially about 3:1.

In a particular embodiment, the sustained-release coating comprises ethyl cellulose as Aquacoat ECD 30 and HPMC 6 cps as Opadry Clear, and further comprises talc and a plasticizer, wherein the ratio of EC and HPMC is in the range 19:1 to 4:1 especially about 9:1; the ratio of EC to talc is in the range 19:1 to 4:1 especially about 9:1, and the ratio of EC to plasticizer is in the range 9:1 to 2:1 especially about 3:1.

In a particular embodiment, the sustained release coating comprises Eudragit RS30D, Eudragit RL30D or mixtures thereof wherein the ratio of the first and second copolymer is in the range of 1:5 to 1:15, especially about 1:9.

The sustained release coating may be applied to the formulation in tablet form or to the drug-coated spherical particles.

In some embodiments, the formulation may comprise more than one sustained-release coating. In some embodiments, a first sustained release coating may be present followed by a second sustained-release coating. The first and second sustained release coatings may be the same or different. For example, the first coating may be an ethylcellulose coating and the second coating a Eudragit coating such as a combination of Eudragit RS30D and Eudragit RL30D or the first coating may be a combination of Eudragit RS30D and Eudragit RL30D and the second coating may be Eudragit RS30D.

Typically, the sustained-release coatings will be present in an amount of 1 to 40% w/w of the sustained-release coated formulation, especially 3 to 30%, more especially 5 to 25%. In one embodiment, an ethylcellulose coating may be present in an amount of 3 to 15% w/w of the sustained-release coated formulation, especially 5 to 10%, for example, about 7.5% or may be present in an amount of about 5% w/w of the sustained-release coated formulation. In another embodiment, an ethylcellulose coating may be present in an amount of about 10% w/w of the sustained-release coated formulation. In yet another embodiment, a sustained-release coating of Eudragit RL30D and Eudragit RS30D may be present in an amount of about 25% w/w of the sustained-release coated formulation and may further comprise a sustained-release coating of Eudragit RS30D which may be present in an amount of about 15% w/w of the sustained-release coated formulation.

Enteric-Release Coat

Optionally, any of the formulations above may include an enteric-release coating. Suitable enteric-release coatings include cellulose coatings such as cellulose acetate phthalate polymers or hydroxypropyl methylcellulose phthalate polymers or co-polymers of acrylic acids and their esters or methacrylic acids or their esters, such as those sold under the trade mark Eudragit® including L100, L100-55 and S100. In particular embodiments, the enteric-release coating may comprise poly(methacrylic acid-co-ethyl acrylate) 1:1 (Eudragit L100-55); poly(methacrylic acid-co-ethyl acrylate) 1:1 (Eudragit L100) and methacrylic acid-methyl methacrylate copolymer (1:2) (Eudragit S100). In a preferred embodiment, the enteric release coating is poly(methacrylic acid-co-ethyl acrylate) 1:1 (Eudragit L100-55) or an aqueous dispersion thereof (Eudragit L30 D-55).

The enteric-release coatings may also comprise lubricants. The enteric-release coatings may also comprise plasticizers. The enteric-release coatings may also comprise anti-tacking agents.

In a particular embodiment, the enteric-release coating comprises Eudragit L100-55.

In a particular embodiment, the enteric-release coating comprises Eudragit L100-55 and a plasticizer wherein the ratio of polymer and plasticizer is in the range 19:1 to 4:1 especially about 9:1.

In a particular embodiment, the enteric-release coating comprises Eudragit L100-55, plasticizer and an anti-tacking agent, wherein the ratio of polymer and plasticizer is in the range 19:1 to 4:1 especially about 9:1 and the ratio of polymer to anti-tacking agent is in the range 4:1 to 1:4, preferably 3:1 to 1:3, more preferably 3:2 to 2:3, for example 3:2 or 1:1.

Typically, the enteric-release coatings will be present in an amount of 20-60% w/w of the enteric-release coated formulation, for example 20 to 50% w/w, especially 25 to 40% w/w, for example about 40% w/w or 30% w/w of the enteric-release coated formulation. In one embodiment, a coating of poly(methacylic acid-co-ethyl acrylate) 1:1 (Eudragit L100-55) may be present in an amount of about 30% w/w of the enteric-release coated formulation.

Formulations

In some embodiments, the formulations of the invention may include further excipients such as dispersants, solvents, preservatives, flavours, microbial retardants and the like. Examples of dispersing agents include vegetable oils, aliphatic or aromatic hydrocarbons (e.g. n-decane, n-hexane etc.), aliphatic or aromatic esters (e.g. octanonate) and ketones. Solvents that are poorly miscible with water, such as dichloromethane, chloroform and fluorinated hydrocarbons are also examples of dispersing agents. The dispersing agents may be removed from the formulation in the process of forming the matrix and/or after preparation of the invention but prior to administration. Suitable preservatives and antimicrobial agents include for example, EDTA, benzyl alcohol, bisulphites, monoglyceryl ester of lauric acid (Monolaurin), capric acid and/or its soluble alkaline salts or its monoglyceryl ester (Monocaprin), edetate and capric acid and/or its soluble alkaline salts or its monoglyceryl ester (Monocaprin) and edetate.

Reference can conveniently be made to Remington's Pharmaceutical Sciences, Mack Publishing Company, Eaton, USA, 1990 and Rowe's Handbook of Pharmaceutical Excipients, 2009 for formulation methods and reagents.

The formulations may be any type of solid oral dosage form, for example, tablets, minitablets or capsules. For example, the formulations of the invention may be compressed into tablet form or the coated particles may be filled into a capsule. Techniques for formulation of solid oral dosage forms are known in the art.

In a particular embodiment of the invention there is provided a formulation comprising a compound of formula (I) (1) in a polymeric matrix (2), the polymeric matrix and compound of formula (I) mixture having a seal coating (3). The seal-coated polymeric matrix compound of formula (I) has a sustained-release coating (4) and the formulation further comprises an enteric-release coating (5) as shown in FIG. 1. Optionally, there is a buffer-coating between the sustained-release coating (4) and the enteric-release coating (5).

In some embodiments, the compound of formula (I) is milrinone. In some embodiments, the polymer matrix of the core is HPMC or HPC (80,000 to 120,000) and HPMC (50 cps) in a ratio of 2:1 to 1:2, especially 1.5:1 to 1:1.5, more especially about 1:1. In some embodiments, the seal coating comprises a polymer selected from HMPC or PVA and a plasticizer selected from PEG and/or glycerine. In some embodiments, the buffer-coating comprises a polymer selected from HMPC or PVA and a plasticizer selected from PEG and/or glycerine. In some embodiments, the sustained-release coating comprises ethylcellulose. In some embodiments, the enteric-release coating comprises cellulose acetate phthalate polymers, hydroxypropyl methylcellulose phthalate polymers or copolymers of acrylic acids and their esters or methacrylic acid and their esters.

In another aspect of the invention there is provided a method for treating a subject with heart failure or a stage, class or manifestation of heart failure or at risk of developing or exhibiting symptoms of heart failure, said method comprising administering to the subject, a formulation of the invention.

Reference to "heart failure" includes any condition resulting in an inability for the heart to supply sufficient blood flow to meet the body's needs. Such conditions include cardiovascular events which lead to heart failure or a potential of heart failure. Conditions which can lead to heart failure include myocardial infarction (MI), cardiomyopathies, such as, alcoholic cardiomyopathy, coronary artery disease, congenital heart disease, nutritional diseases affecting the heart, ischemic (or ischemic) cardiomyopathy, hypertensive cardiomyopathy, valvular cardiomyopathy, inflammatory cardiomyopathy, cardiovascular disease, such as atherosclerosis, ischemic heart disease, hypertensive heart disease, such as, left ventricular hypertrophy, coronary heart disease, (congestive) heart failure, hypertensive cardiomyopathy, cardiac arrhythmias, inflammatory heart disease, such as, endocarditic, inflammatory cardiomegaly, myocarditis, valvular heart disease, such as, aortic valve stenosis, mitral valve prolapse and valvular cardiomyopathy as well as heart failure itself.

The "method" of treatment may also be referred to as a therapeutic protocol, cardiotonic therapy, patient management system, emergency triage therapy, and the like and includes a prophylactic aspect in so far as a subject may present with an imminent risk of exhibiting heart failure.

The "manifestations" of HF contemplated herein include the symptoms of HF such as shortness of breath including orthopnea, coughing, ankle swelling and exercise intolerance. All forms of HF are encompassed by the present invention including "left" and "right" sided ventricular-attributed symptoms and bi-ventricular-attributed symptoms as well as any stage or class of HF. Stage 1V HF is a particular feature of the present invention although any stage may be treated.

The administration is generally for a time and under conditions sufficient to achieve levels of the compound of formula (I) which are not overly toxic and which is effective to ameliorate the symptoms of HF. Conveniently, the compound of formula (I) is formulated in a controlled-release matrix comprising the compound, polymer, seal coating, sustained-release coating and excipients sufficient to enable compound release into the blood stream at a rate of between above 0.1 µg/kg body weight/minute to about 20 µg/kg body weight/minute. This range includes 0.1, 0.2, 0.3, 04, 0.5, 0.6, 0.7, 0.8, 0.9, 1, 2, 3, 4, 5, 6, 7, 8, 9, 10, 11, 12, 13, 14, 15, 16, 17, 18, 19 and 20 µg/kg body weight/minute as well as fractions in between. In a particular embodiment, the compound of formula (I) is released at a rate of from about 0.3 to 1 µg/kg body weight/minute including from about 0.37 to 0.75 µg/kg body weight/minute.

The amount of compound of formula (I) that is administered will depend on the subject being treated, their physical condition, their weight and the formulation being used. Suitable dosages are in the range of 5 mg to 75 mg, especially 10 to 50 mg or 10 to 40 mg.

The dosage may be provided in a single dose per day, for example, one dose of 30 to 40 mg, or may be provided in divided dosages for example, two, three or four times a day. Amounts 15 to 30 mg or 15 to 20 mg every 12 hours is a useful therapeutic amount in accordance with the present invention and allows for 12 hourly or twice daily dosing. Amounts of 10 to 15 mg every 8 hours allows for dosing three times per day and amounts of 7.5 to 10 mg every 6 hours allows for dosing four times a day. In particular embodiments, administration is twice daily.

The formulations of the invention may be administered alone or in combination with other medicaments such as an angiotensin-converting enzyme inhibitor (ACE inhibitor) such as Ceptopril, Enalapril, Lisnopril, Ramipril, Qinapril, Fosnopril, Benazipril and/or Trandolapril, an angiotensin receptor blocker such as Valsartan, Candesartan, Losartan, Irbesartan, Telmisartan, Eprosartan and/or Olmesartan, a beta blocker such as Carvedilol, Metoprolol succinate, Metoprolol tartrate, Bisoprolol, Nebivolol and bucindolol, a digoxin or other neurohormonal modulating agents such as Digoxin, Hydralazine, isosorbide dinitrate, Spironolactone and/or Eplerenone, a diuretic such as Furosemide, Burmetamide, Torsamide, Ethacrynic acid, Hydrochlorohiazide and/or Metrolazone, an aldosterone antagonist, a calcium channel antagonist, a statin, a diuretic, digitalis, a vasodilator, an antiarrhythmic, dopamine or dobutamine.

Administration of the formulations of the invention may also be undertaken with other therapeutic interventions such as for the treatment of arterial fibrillation, sleep apnea, anemia, obesity, diabetes and thyroid disease, cardiac resynchronization therapy, defibrillation therapy and surgical intervention. The latter includes cardiac bypass surgery, left ventricular assist devices, ventricular reconstruction surgery and cardiac transplantation. Behavioural modification including diet and exercise may also be required.

The present invention may also be useful in the treatment of a subject with pulmonary hypertension. In some embodiments, this therapy may be useful in treating patients with pulmonary hypertension and end-stage HF, or those being assessed for cardiac transplantation. Oral milrinone therapy may have utility in patients with end-stage HF and secondary pulmonary hypertension, particularly in patients that show inadequate hemodynamic response to previous therapy (pulmonary capillary wedge pressure, >18 mmHg) and who have shown minimal symptomatic benefit from continuous infusions of loop diuretics. Therapy with controlled-release and milrinone may improve hemodynamic measures and clinical symptoms.

In this embodiment, the milrinone may be administered in combination with a phosphodiesterase inhibitor such as sildenafil, tadalafil, vardenafil, udenafil and avanfil; or a endothelin antagonist such as bosentan, tezosentan, zibotentan, sitazentan, ambrisentan, atrasentan and BQ-123.

The term "subject" generally means a human. However, the present invention extends to the treatment of animal model systems including non-human primates as well as pigs, sheep, dogs and horses. Non-human commercial applications include the treatment of race animals such as horses, dogs and camels as well as work animals such as horses and dogs. By "human" means a person of any age from infant, child, adolescent, teenager, young adult, adult, middle age and aging individual. Age ranges from 1 day old to 120 years old are contemplated herein. In extreme emergencies, in utero treatments of unborn babies may be contemplated and is encompassed by the present invention.

The optimal plasma level of milrinone is in the range of 100 ng/mL to 400 ng/mL, especially 100 ng/mL to 300 ng/mL. Plasma clearance of milrinone is affected by the presence of either renal or cardiovascular disease. The optimal dose of controlled-release milrinone may need to be determined for an individual patient by a stepwise upward titration of the dose accompanied by regular monitoring of the patient's plasma levels of milrinone until the required steady state level is achieved.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

The present invention is further described by the following non-limiting Examples.

EXAMPLES

| Reference equipment/instrument name | Manufacturer |
|---|---|
| Blender (5 liters) | Kalweka |
| Co-mil | Kevin |
| Compression Machine | Cadmach |
| Double cone blender (5 liters) | Kalweka |
| Ganscoater (GAC-275) | Gansons |
| Halogen moisture analyser | Precisa |
| Homogeniser | Silversons |
| Powder coater and granulator (GPCG1.1) | Glatt |
| Propeller mixer | Hally instruments |
| Rapid Dryer | Retsch |
| Rapid Mixer Granulator (5 liters) | Kevin |
| Roller compactor WP120 | Alexanderwerk |
| Sieves | Labsupplies India Pvt. Ltd. |
| Tablet hardness tester | Erweka |
| Turbula Shaker Mixer | Willy A. Bachofen AG (WAB) |
| Vacuum oven | Servewell instruments |
| Vernier caliper | Mitutoyo |
| Weighing Balance | Sartorious |
| Wurster coater 2.4 L (GPCG 1.1) | Glatt |

Example 1

Minitablet Formulation Comprising Hydroxypropylmethylcellulose Matrix

Summary Table of HPMC Based Compositions Providing w/w Ratios of Components

| | % w/w Batch No. | | | | | | |
|---|---|---|---|---|---|---|---|
| Ingredients | 032 | 031 | 025 | 017 | 015 | 007 | 004 |
| Method | Wet granulation | | Roller compaction | Slugging | Direct compression | | |
| Tablet core | | | | | | | |
| Milrinone | 20 | 20 | 15 | 20 | 20 | 20 | 20 |
| HPMC K100M | 30 | 30 | 30 | 30 | 30 | 30 | 20 |
| HPMC E50 LV | 30 | 30 | 30 | 30 | 30 | 10 | — |
| Avicel PH102 | 18 | 18 | 23 | 18 | 18 | 20 | 30 |
| Lactopress | — | — | — | — | — | 15 | 25 |
| PVPK30 | — | — | — | — | — | 3.5 | 3.5 |
| Aerosil | — | — | — | — | — | 1 | 1 |
| Mag. stearate | 2 | 2 | 2 | 2 | 2 | 0.5 | 0.5 |
| Total | 100 | 100 | 100 | 100 | 100 | 100 | 100 |
| Seal Coated Core | | | | | | | |
| Tablet core | 90 | 90 | 90 | 90 | — | — | — |
| Opadry white | 10 | 10 | 10 | 10 | — | — | — |
| Total | 100 | 100 | 100 | 100 | — | — | — |
| SR Coated Core | | | | | | | |
| Seal Coated Core | 92.5 | 92.5 | 90 | 90 | — | — | — |
| Aquacoat ECD 30 | 7.5 | 7.5 | 10 | 10 | — | — | — |
| Opadry clear | | | | | — | — | — |
| Triethyl citrate | | | | | — | — | — |
| Talc | | | | | — | — | — |
| Total | 100 | 100 | 100 | 100 | — | — | — |
| Buffer Coated Core | | | | | | | |
| SR coated core | 95 | 95 | 90 | 90 | — | — | — |
| Opadry white | 5 | 5 | 10 | 10 | — | — | — |
| Total | 100 | 100 | 100 | 100 | — | — | — |
| ER Coated Core | | | | | | | |
| Buffer coated core | 70 | 70 | 60 | 60 | — | — | — |
| Eudragit L30D55 | 30 | 30 | 40 | 40 | — | — | — |
| Triethyl citrate | | | | | — | — | — |
| Talc | | | | | — | — | — |
| Total | 100 | 100 | 100 | 100 | — | — | — |

Manufacturing Procedure for B. No. 32 Wet Granulation

Objective: Even though required dissolution profile was achieved in Batch 031, this batch is planned to increase the hardness of core Minitablets by adding one portion of Avicel PH 102 in extragranular blend, as there was little dust generation was observed during seal coating.

Manufacturing Formula

| Ingredients | mg/Tablet | For 700 g |
|---|---|---|
| Milrinone | 2.0 | 140.0 |
| HPMC K 100 | 3.0 | 210.0 |
| HPMC E50 | 3.0 | 210.0 |
| Avicel PH 102 | 1.3 | 91.0 |
| Extragranular | | |
| Avicel PH 102 | 0.5 | 35.0 |
| Magnesium Starate | 0.2 | 14.0 |
| Total | 10.0 | 700.0 |

Step 1: Weighing
All ingredients were weighed separately into a double polybag and/or butter paper.
Step 2: Sifting
1. HPMC 50 cps, Milrinone, HPMC K100M and Avicel PH102 were sifted through ASTM40 mesh.
Step 3: Granulation
1. Above sifted ingredients (intragranular) were added into rapid mixer granulator.
2. Dry mixing was done for 5' min. at impeller speed of 150 rpm.
3. 420 g Purified water was then added slowly in 2 minutes and wet massing was done for 2 minutes at 150 rpm with Chopper on at 1500 rpm.
4. Finally wet granules were unloaded from the bowl.
Step 4: Drying
1. Wet mass was dried in Rapid Dryer at product temperature of 50° C. for 45 min until % w/w moisture reduced to 3-4% w/w.
2. Granules were sifted through ASTM 30 mesh
Step 5: Milling (Granules)
1. Granules were milled through screen no. 1016 (1 mm) using Co-mil
2. Step 4 and 5 granules were mixed together
Step 6: Sifting
1. Extragranular Avicel is sifted through ASTM 40 mesh.
2. Magnesium stearate was sifted through ASTM 60 mesh.
Step 7: Blending (Extra-Granular)
1. Granules and Extragranular Avicel were mixed together into a double cone blender for 5 min at 15 rpm.
2. Granules and magnesium stearate were mixed together into a double cone blender for 15 min at 15 rpm.
3. Lubricated granules were unloaded into a double cone blender and were kept ready for compression.
Step 8: Compression
1. Cadmach CU 20 compression machine was fixed with one "D" tooling multitip punch set.
 a. Upper punch: 2 mm, round, standard concave (12 tips)
 b. Lower punch: 2 mm, round, standard concave (12 tips)
Step 9: In-Process Duality Control Testing of Core Minitablets

| In-process parameters | Values/observations | | |
| --- | --- | --- | --- |
| | Average | Minimum | Maximum |
| Hardness (N) | 20.5 | 15 | 25 |
| Thickness (mm) | 2.69 | 2.65 | 2.78 |
| Weight (mg) | 10.10 | 9.91 | 10.54 |

Step 10: Coating (Seal Coat)
1. Minitablets were seal coated using Opadry white at 10% w/w weight gain of film coat.
2. Coating was done using bottom spray container (2.4 liters) at following equipment parameters,

| Coating process parameter | Values |
| --- | --- |
| Inlet temperature | 45 to 55° C. |
| Product temperature | 38 to 42° C. |
| Exhaust temperature | 35 to 45° C. |
| Blower speed | 60 to 80% |
| Spray pump speed (rpm) | 5 to 15 |
| Atomisation (Bars) | 0.9 to 1.2 |
| Air flow (cfm) | 65 to 94 |

Step 11: In-Process Quality Control Testing of Seal Coated Minitablets

| In-process parameters | Values/observations | | |
| --- | --- | --- | --- |
| | Average | Minimum | Maximum |
| Hardness (N) | 28.5 | 25 | 37 |
| Thickness (mm) | 2.95 | 2.89 | 3.02 |
| Weight (mg) | 10.90 | 11.12 | 11.35 |

Step 12: Sustained Release Coating
1. 7.5% w/w sustained release coating of Minitablets was done using Aquacoat ECD 30 (Ethyl cellulose dispersion) where triethyl citrate was used as a plasticizer. Step 12:

| Ingredients | Ratio to EC solids | Total Dissolved Solids (TDS) (g) | Quantities Taken (g) |
| --- | --- | --- | --- |
| Aquacoat ECD (as 30% w/w suspension) | | 24.78 | 82.76 |
| Opadry Clear | 10% | 2.48 | 2.48 |
| Talc | 10% | 2.48 | 2.48 |
| Triethyl Citrate | 25% | 6.21 | 146.02 |
| Purified water | QS for 15% Solution | — | |
| Total | | 36.00 | 239.95 |

2. Coating was done by Wurster coater (bottom spray container 2.4 liters) at following equipment parameters,

| Coating process parameter | Values |
| --- | --- |
| Inlet temperature | 50 to 60° C. |
| Product temperature | 38 to 42° C. |
| Exhaust temperature | 35 to 45° C. |
| Blower speed | 60 to 84% |
| Spray pump speed (rpm) | 5 to 15 |
| Atomisation (Bars) | 0.9 to 1.2 |
| Air flow (cfm) | 65 to 95 |

3. After coating, curing was done for 2 hours at product temperature around 60° C. in Hot air oven.
Step 13: In-Process Quality Control Testing of Sustained Release Coated Minitablets

| In-process parameters | Values/observations | | |
| --- | --- | --- | --- |
| | Average | Minimum | Maximum |
| Hardness (N) | 37 | 30 | 45 |
| Thickness (mm) | 3.03 | 2.98 | 3.15 |
| Weight (mg) | 11.76 | 11.65 | 11.88 |

Step 14: Buffer Coating
1. Buffer coating was done at 5% w/w weight gain using opadry white.
2. Coating was done using bottom spray container (2.4 liters) at following equipment parameters,

| Coating process parameter | Values |
| --- | --- |
| Inlet temperature | 45 to 55° C. |
| Product temperature | 38 to 42° C. |

-continued

| Coating process parameter | Values |
|---|---|
| Exhaust temperature | 35 to 45° C. |
| Blower speed | 60 to 80% |
| Spray pump speed (rpm) | 5 to 15 |
| Atomisation (Bars) | 0.9 to 1.2 |
| Air flow (cfm) | 65 to 94 |

Step 15: Enteric Coating

1. Enteric coating of buffer coated minitablets was done by using Eudragit L30 D55 polymer at 30% W/w weight gain where talc was used as an antitacking agent and triethylcitrate was used as a plasticizer.

| Ingredients | Ratio to Eudragit solids | TDS (g) | Quantities Taken (g) |
|---|---|---|---|
| Eudragit 130 D55 | | 90.00 | 300.00 |
| Talc | 50 | 45.00 | 45.00 |
| Triethyl Citrate | 10 | 9.00 | 9.00 |
| Purified water | QS for 15% Solution | — | 366.00 |
| Total | | | 144.0 |

2. Coating was done using bottom spray container (2.4 liters) at following equipment parameters,

| Coating process parameter | Values |
|---|---|
| Inlet temperature | 28 to 34° C. |
| Product temperature | 25 to 30° C. |
| Exhaust temperature | 28 to 32° C. |
| Blower speed | 50 to 98% |
| Spray pump speed (rpm) | 5 to 14 |
| Atomisation (Bars) | 0.8 to 1.3 |
| Air flow (cfm) | 60 to 100 |

3. After coating curing of Minitablets was done for 2 hour at product temperature 40° C. in hot air oven.

Step 16: In-Process Quality Control Testing of Enteric Coated Minitablets

| In-process parameters | Values/observations | | |
|---|---|---|---|
| | Average | Minimum | Maximum |
| Hardness (N) | 54.5 | 42 | 67 |
| Thickness (mm) | 3.23 | 3.18 | 3.26 |
| Weight (mg) | 16.10 | 15.80 | 16.45 |

Manufacturing Procedure for B. No. 31 Wet Granulation

| Ingredients | Quantity of materials (g) |
|---|---|
| Milrinone | 140.0 |
| HPMC K100M | 210.0 |
| HPMC E50 LV | 210.0 |
| Avicel PH102 | 126.0 |
| Magnesium stearate | 14.0 |
| Total | 700.0 |

Objective: Considering the dissolution profile of Batch-025, a batch was planned to increase the drug release by reducing the Sustained release coating (Aquacoat ECD 30) from 10% to 7.5%. The enteric coating was reduced from 40% to 30% as it was sufficient to prevent the drug release in stomach.

Step 1: Weighing

All ingredients were weighed separately into a double polybag and/or butter paper.

Step 2: Sifting

1. HPMC 50 cps, Milrinone, HPMC K100M and Avicel PH102 were sifted through ASTM40 mesh.

Step 3: Granulation

1. Above sifted ingredients were added into rapid mixer granulator.
2. Dry mixing was done for 5 min. at impeller speed of 150 rpm.
3. 420 g Purified water was then added slowly in 2 minutes and wet massing was done for 2 minutes at 150 rpm with Chopper on at 1500 rpm.
4. Finally wet granules were unloaded from the bowl.

Step 4: Drying

1. Wet mass was dried in Rapid Dryer at product temperature of 50° C. for 45 min until % w/w moisture reduced to 3-4% w/w.
2. Granules were sifted through ASTM 30 mesh.

Step 5: Milling (Granules)

1. Granules were milled through, screen no. 1016 (1 mm) using Co-mil.
2. Step 4 and 5 granules were mixed together.

Step 6: Sifting

1. Magnesium stearate was sifted through ASTM 60 mesh.

Step 7: Blending (Extra-Granular)

1. Granules and magnesium stearate were mixed together into a double cone blender for 15 min at 15 rpm.
2. Lubricated granules were unloaded into a double cone blender and were kept ready for compression.

Step 8: Compression

1 Cadmach CU 20 compression machine was fixed with one "D" tooling multitip punch set.
 a. Upper punch: 2 mm, round, standard concave (12 tips)
 b. Lower punch: 2 mm, round, standard concave (12 tips)

Step 8: In-Process Quality Control Testing of Core Minitablets

| In-process parameters | Values/observations | | |
|---|---|---|---|
| | Average | Minimum | Maximum |
| Hardness (N) | 18.5 | 12 | 22 |
| Thickness (mm) | 2.79 | 2.78 | 2.82 |
| Weight (mg) | 10.21 | 9.85 | 10.50 |

Step 10: Coating (Seal Coat)

1. Minitablets were seal coated using opadry white at 10% w/w weight gain of film coat.
2. Coating was done using bottom spray container (2.4 liters) at following equipment parameters

| Coating process parameter | Values |
|---|---|
| Inlet temperature | 45 to 55° C. |
| Product temperature | 38 to 42° C. |
| Exhaust temperature | 35 to 45° C. |
| Blower speed | 60 to 80% |

| Coating process parameter | Values |
| --- | --- |
| Spray pump speed (rpm) | 5 to 15 |
| Atomisation (Bars) | 0.9 to 1.2 |
| Air flow (cfm) | 65 to 94 |

Step 11: In-Process Quality Control Testing of Seal Coated Minitablets

| | | Values/observations | |
| --- | --- | --- | --- |
| In-process parameters | Average | Minimum | Maximum |
| Hardness (N) | 26.20 | 22 | 34 |
| Thickness (mm) | 2.85 | 2.83 | 2.95 |
| Weight (mg) | 11.23 | 11.12 | 11.35 |

Step 12: Sustained Release Coating 1. 7.5% w/w sustained release coating of Minitablets was done using Aquacoat ECD 30 (Ethyl cellulose dispersion) where triethyl citrate was used as a plasticizer.
2. Coating was done by wurster coater (bottom spray container 2.4 liters) at following equipment parameters,

| Coating process parameter | Values |
| --- | --- |
| Inlet temperature | 50 to 60° C. |
| Product temperature | 38 to 42° C. |
| Exhaust temperature | 35 to 45° C. |
| Blower speed | 60 to 84% |
| Spray pump speed (rpm) | 5 to 15 |
| Atomisation (Bars) | 0.9 to 1.2 |
| Air flow (cfm) | 65 to 95 |

3. After coating, curing was done for 2 hours at product temperature around 60° C. in Hot air oven.

Step 13: In-Process Quality Control Testing of Sustained Release Coated Minitablets

| | | Values/observations | |
| --- | --- | --- | --- |
| In-process parameters | Average | Minimum | Maximum |
| Hardness (N) | 30.10 | 23 | 37 |
| Thickness (mm) | 2.95 | 2.93 | 2.98 |
| Weight (mg) | 12.11 | 12.06 | 12.18 |

Step 14: Buffer Coating

1. Buffer coating was done at 5% w/w weight gain using opadry white.
2. Coating was done using bottom spray container (2.4 liters) at following equipment parameters,

| Coating process parameter | Values |
| --- | --- |
| Inlet temperature | 45 to 55° C. |
| Product temperature | 38 to 42° C. |
| Exhaust temperature | 35 to 45° C. |
| Blower speed | 60 to 80% |
| Spray pump speed (rpm) | 5 to 15 |
| Atomisation (Bars) | 0.9 to 1.2 |
| Air flow (cfm) | 65 to 94 |

Step 15: Enteric Coating

1. Enteric coating of buffer coated minitablets was done by using Eudragit L30 D55 polymer at 30% w/w weight gain where talc was used as an antitacking agent and triethyl citrate was used as a plasticizer.
2. Coating was done using bottom spray container (2.4 liters) at following equipment parameters,

| Coating process parameter | Values |
| --- | --- |
| Inlet temperature | 28 to 34° C. |
| Product temperature | 25 to 30° C. |
| Exhaust temperature | 28 to 32° C. |
| Blower speed | 50 to 98% |
| Spray pump speed (rpm) | 5 to 14 |
| Atomisation (Bars) | 0.8 to 1.3 |
| Air flow (cfm) | 60 to 100 |

3. After coating curing of Minitablets was done for 2 hour at product temperature 40° C. in hot air oven.

Step 16: In-Process Quality Control Testing of Enteric Coated Minitablets

| | | Values/observations | |
| --- | --- | --- | --- |
| In-process parameters | Average | Minimum | Maximum |
| Hardness (N) | 48.5 | 43 | 66 |
| Thickness (mm) | 3.25 | 3.11 | 3.35 |
| Weight (mg) | 16.80 | 16.77 | 16.85 |

Manufacturing Procedure for B. No. 025 Wet Granulation

| Ingredients | Quantity of materials (g) |
| --- | --- |
| Milrinone | 98.00 |
| HPMC K100M | 195.00 |
| HPMC E50 LV | 195.00 |
| Avicel PH102 | 149.00 |
| Magnesium stearate | 13.00 |
| Purified water | 400.00 |
| Total | 650.00 |

Step 1: Weighing

All ingredients were weighed separately into a double polybag and/or butter paper. Note: Milrinone quantity was weighed based upon following calculation, Assay of Milrinone=99.70% (as is basis)

mg/tablet of Milrinone=theoretical quantity of Milrinone (mg/tablet)×100/Assay of Milrinone i.e. 1.50×100/99.7=1.51 mg The quantity of API was adjusted with Microcrystalline cellulose.

Step 2: Sifting

1. HPMC E50 LV and Milrinone were co-sifted through ASTM40 mesh.
2. HPMC K100M and Avicel PH102 were sifted through ASTM40 mesh.

Step 3: Granulation

1. Step 1 and 2 ingredients were added into rapid mixer granulator.
2. Dry mixing was done for 5 min. at impeller speed of 150 rpm.
3. 400 g Purified water was then added slowly in 2 minutes and wet massing was done for 2 minutes at 150 rpm.
4. Finally wet mass was unloaded from the bowl.

Step 4: Drying

1. Wet mass was dried in Rapid Dryer at product temperature of 30 to 44° C. for 1 hour until % w/w moisture reduced to 2% w/w.

2. Granules were sifted through ASTM 30 mesh

Step 5: Milling (Granules)

1. Granules were milled through screen no. 1016 (1 mm) using Co-mil.

2. Step 4 and 5 granules were mixed together

Step 6: Sifting

Magnesium stearate was sifted through ASTM 60 mesh.

Step 7: Blending (Extra-Granular)

1. Granules and magnesium stearate were mixed together into a double cone blender for 15 min. at 15 rpm.

2. Lubricated granules were unloaded into a double cone blender and were kept ready for compression.

Step 8: Compression

1. Cadmach CU 20 compression machine was fixed with one "D" tooling multitip punch set.
   a. Upper punch: 2 mm, round, standard concave (12 tips)
   b. Lower punch: 2 mm, round, standard concave (12 tips)

2. Tablets were compressed using Cadmach CU 20 compression machine. Compression was done manually by rotating hand wheel to obtain enough hardness and thickness at the adjusted average weight of 10.00 mg.

Step 9: In Process Quality Control Testing of Core Minitablets

| In-process parameters | Values/observations | | |
|---|---|---|---|
| | Average | Minimum | Maximum |
| Hardness (N) | 21.6 | 15 | 29 |
| Thickness (mm) | 2.79 | 2.78 | 2.80 |
| Weight (mg) | 9.62 | 9.00 | 10.50 |

Step 10: Coating (Seal Coat)

1. Minitablets were seal coated using Opadry white at 10% w/w weight gain of film coat. Opadry™ film coating system powder was added to water and mix for 45 minutes with a propeller stirrer. The coating suspension can be made with up according to the manufacturer's instructions. Coating was done using bottom spray container (2.4 liters) at following equipment parameters,

| Coating process parameter | Values |
|---|---|
| Inlet temperature | 47 to 52° C. |
| Product temperature | 37 to 39° C. |
| Exhaust temperature | 38 to 40° C. |
| Blower speed | 65 to 95% |
| Spray pump speed (rpm) | 5 to 15 |
| Atomisation (Bars) | 0.8 to 1.2 |
| Air flow (cfm) | 81 to 116 |

Step 11: In-Process Quality Control Testing of Seal Coated Minitablets

| In-process parameters | Values/observations | | |
|---|---|---|---|
| | Average | Minimum | Maximum |
| Hardness (N) | 43.8 | 35 | 52 |
| Thickness (mm) | 2.80 | 2.78 | 2.81 |
| Weight (mg) | 10.75 | 10.6 | 10.9 |

Step 12: Sustained Release Coating 1. 10% w/w sustained release coating of minitablets was done using Aquacoat ECD 30 (Ethyl cellulose dispersion) and talc, where triethyl citrate was used as a plasticizer.

Composition of coating dispersion has been tabulated below.

| Sr. No. | Ingredients | Manufacturer | Ratio to EC solids | Total Dissolved Solids (TDS) (g) | Quantities (g) for 450 g batch size |
|---|---|---|---|---|---|
| 01 | Ethylcellulose aqueous dispersion (Aquacoat ECD 30) | FMC Biopolymer | — | 40.34 | 134.48 g |
| 02 | Opadry clear | Colorcon | 10% | 4.03 | 4.03 g |
| 03 | Triethyl citrate | Sigma Aldrich | 25% | 10.09 | 10.09 g |
| 04 | Talc | Luzenac Pharma | 10% | 4.03 | 4.03 g |
| 05 | Purified water | FDC In-house | QS for 15% Solution | — | 237.36 g |

2. Coating was done by wurster coater (bottom spray container 2.4 liters) at following equipment parameters,

| Coating process parameter | Values |
|---|---|
| Inlet temperature | 31 to 52° C. |
| Product temperature | 31 to 42° C. |
| Exhaust temperature | 31 to 43° C. |
| Blower speed | 50 to 99% |
| Spray pump speed (rpm) | 5 to 15 |
| Atomisation (Bars) | 0.5 to 1.2 |
| Air flow (cfm) | 53 to 100 |

3. After coating, curing was done for 2 hours at product temperature around 60° C. in the equipment.

Step 13: In-Process Quality Control Testing of Sustained Release Coated Minitablets

| In-process parameters | Values/observations | | |
|---|---|---|---|
| | Average | Minimum | Maximum |
| Hardness (N) | 63.8 | 56 | 70 |
| Thickness (mm) | 2.84 | 2.81 | 2.85 |
| Weight (mg) | 11.79 | 11.5 | 12.0 |

Step 14: Buffer Coating

1. Buffer coating was done at 10% w/w weight gain using Opadry White™ as described in Step 10.

2. Coating was done using bottom spray container (2.4 liters) at following equipment parameters,

| Coating process parameter | Values |
|---|---|
| Inlet temperature | 47 to 51° C. |
| Product temperature | 38 to 42° C. |
| Exhaust temperature | 34 to 42° C. |
| Blower speed | 50 to 95% |
| Spray pump speed (rpm) | 2 to 10 |
| Atomisation (Bars) | 0.5 to 1.0 |
| Air flow (cfm) | 58 to 156 |

Step 15: In-Process Quality Control Testing of Buffer Coated Minitablets

| In-process | Values/observations | | |
| --- | --- | --- | --- |
| parameters | Average | Minimum | Maximum |
| Hardness (N) | 43.8 | 35 | 52 |
| Thickness (mm) | 2.80 | 2.78 | 2.81 |
| Weight (mg) | 10.75 | 10.7 | 10.9 |

Step 16: Enteric Coating

1. Enteric coating of buffer coated minitablets was done by using Eudragit L30 D55 polymer at 40% w/w weight gain where talc was used as an antitacking agent and triethylcitrate was used as a plasticizer. The composition of coating dispersion is given in table below,

| Sr. No. | Ingredients | Manufacturer | Ratio to Eudragit solids | Total Dissolved Solids (TDS) (g) | Quantities (g) for 450 g batch size |
| --- | --- | --- | --- | --- | --- |
| 01 | Eudragit L30D55 | Evonik | — | 157.5 | 525.00 g |
| 02 | Triethyl citrate | Sigma Aldrich | 10% | 15.75 | 15.75 g |
| 03 | Talc | Luzenac Pharma | 50% | 78.75 | 78.75 g |
| 04 | Purified water | FDC in-house | | | 1060.50 g |

Note:
40% excess solution was prepared to compensate manufacturing losses.

2. Eudragit L30D55 and Triethylcitrate were mixed together for 45 min. using overhead stirrer.
3. Talc was added into water slowly and was homogenized for 15 min. at 6000 rpm.
4. Step 1.1 and 1.2 dispersions were mixed together for 5 min. using overhead stirrer.
5. Coating was done using bottom spray container (2.4 liters) at following equipment parameters,

| Coating process parameter | Values |
| --- | --- |
| Inlet temperature | 28 to 34° C. |
| Product temperature | 25 to 30° C. |
| Exhaust temperature | 28 to 32° C. |
| Blower speed | 50 to 98% |
| Spray pump speed (rpm) | 5 to 14 |
| Atomisation (Bars) | 0.5 to 1.5 |
| Air flow (cfm) | 58 to 156 |

After coating curing of Minitablets was done for 1 hour at product temperature between 40 to 43° C. in the equipment.

Step 17: In-Process Quality Control Testing of Enteric Coated Minitablets

| In-process | Values/observations | | |
| --- | --- | --- | --- |
| parameters | Average | Minimum | Maximum |
| Hardness (N) | 89.3 | 75 | 109 |
| Thickness (mm) | 3.11 | 3.08 | 3.16 |
| Weight (mg) | 18.05 | 17.9 | 18.2 |

Note:
In case of Minitablets, weight gain is checked based upon unit weights. Hence, before coating average weight of 100 minitablets is taken and after coating again average weight of minitablets is taken. The formula for weight gain calculation is as follows, % w/w practical weight gain achieved = Final weight − Initial weight/Initial weight × 100.

Manufacturing Procedure for Batch No. 004 Direct Compression

| Ingredients | Quantity of materials (g) |
| --- | --- |
| Milrinone | 25.13 |
| HPMC K100M | 25.00 |
| HPMC E50 LV | — |
| Avicel PH102 | 37.50 |
| Lactopress | 31.13 |
| PVPK30 | 4.38 |
| Aerosil | 1.25 |
| Magnesium stearate | 0.63 |
| Total | 125 |

Step 1: Dispensing

All ingredients were weighed separately into a double polybag and/or butter paper. Note: Milrinone quantity was weighed based upon following calculation,
Assay of Milrinone=99.70% (as is basis)
mg/tablet of Milrinone=Theoretical quantity of Milrinone (mg/tablet)×100/Assay of Milrinone
i.e. 2.00×100/99.7=2.01 mg
The quantity of API was adjusted with Lactose.

Step 2: Sifting
1. Milrinone, HPMC K100M, Avicel PH102, Lactose, PVPK30 and Aerosil were sifted through ASTM 40 mesh.
2. Magnesium stearate was sifted through ASTM 60 mesh.

Step 3: Blending
1. Step 1 ingredients from above step were added into 0.5 L Turbula Shaker Mixer container for 30 min. at 49 rpm.
2. Magnesium stearate was then added into it and further 5 min. blending was done at 49 rpm.

Step 4: Compression
1. Cadmach CU 20 compression machine was fixed with one "D" tooling multitip punch set.
   a. Upper punch: 2 mm, round, standard concave (12 tips)
   b. Lower punch: 2 mm, round, standard concave (12 tips)
2. Tablets were compressed using Cadmach CU 20 compression machine.

Compression was done manually by rotating hand wheel to obtain enough hardness and thickness.

Step 5: In-Process Quality Control Testing of Core Minitablets

| In-process | Values/observations | | |
| --- | --- | --- | --- |
| parameters | Average | Minimum | Maximum |
| Hardness (N) | 32 | 25 | 49 |
| Thickness (mm) | 2.05 | 2.03 | 2.14 |
| Weight (mg) | 10.00 | 9.00 | 10.00 |
| Friability | | Nil | |

Manufacturing Procedure for Batch No. 007 Direct Compression

| Ingredients | Quantity of materials (g) |
| --- | --- |
| Milrinone | 25.13 |
| HPMC K100M | 37.50 |
| HPMC E50 LV | 12.50 |
| Avicel PH102 | 25.00 |
| Lactopress | 18.63 |

-continued

| Ingredients | Quantity of materials (g) |
|---|---|
| PVPK30 | 4.38 |
| Aerosil | 1.25 |
| Magnesium stearate | 0.63 |
| Total | 125 |

Step 1: Dispensing

All ingredients were weighed separately into a double polybag and/or butter paper. Note: Milrinone quantity was weighed based upon following calculation, Assay of Milrinone=99.70% (as is basis)

mg/tablet of Milrinone=theoretical quantity of Milrinone (mg/tablet)×100/Assay of Milrinone i.e. 2.00×100/99.7=2.01 mg The quantity of API was adjusted with Lactose.

Step 2: Sifting

1. Milrinone, HPMC E50 LV and HPMC K100M were co-sifted through ASTM 40 mesh

2. Polyvinylpyrrolidone and Lactose were co-sifted through ASTM 40 mesh.

3. Magnesium stearate was sifted through ASTM 60 mesh.

Step 3: Blending

1. Step 1 and 2 ingredients from above step were added into 0.5 liter Turbula Shaker Mixer container for 30 min. at 49 rpm.

2. Magnesium stearate was then added into it and further 5 min. blending was done at 49 rpm.

Step 4: Compression

1. Cadmach CU 20 compression machine was fixed with one "D" tooling multitip punch set.

a. Upper punch: 2 mm, round, standard concave (12 tips)

b. Lower punch: 2 mm, round, standard concave (12 tips)

2. Tablets were compressed using Cadmach CU 20 compression machine.

Compression was done manually by rotating hand wheel to obtain enough hardness and thickness.

Step 5: In-Process Quality Control Testing of Core Minitablets

| In-process parameters | Values/observations | | |
|---|---|---|---|
| | Average | Minimum | Maximum |
| Hardness (N) | 54.8 | 49 | 62 |
| Thickness (mm) | 2.55 | 2.51 | 2.61 |
| Weight (mg) | 9.8 | 9.1 | 10.4 |
| Friability | Nil | | |

Manufacturing Procedure for Batch No. 015 Slugging

| Ingredients | Quantity of materials (g) |
|---|---|
| Milrinone | 25.13 |
| HPMC K100M | 37.50 |
| HPMC E50 LV | 37.50 |
| Avicel PH102 | 22.38 |
| Magnesium stearate | 2.50* (half qty. Intra & half extragranular) |
| Total | 125 |

Step 1: Dispensing

All ingredients were weighed separately into a double polybag and/or butter paper. Note: Milrinone quantity was weighed based upon following calculation, Assay of Milrinone=99.70% (as is basis)

mg/tablet of Milrinone=theoretical quantity of Milrinone (mg/tablet)×100/Assay of Milrinone i.e. 2.00×100/99.7=2.01 mg The quantity of API was adjusted with Microcrystalline cellulose.

Step 2: Sifting

1. HPMC E50 LV and Milrinone were co-sifted through ASTM 40 mesh

2. Magnesium stearate was sifted through ASTM 60 mesh

Step 3: Blending

1. Co-sifted milrinone and HPMC E50 LV were placed in 0.5 L container of Turbula Shaker Mixer and blending was performed for 5 minutes 2. Sifted magnesium stearate was added into it and further 15 min. blending was done.

3. Blend was collected into a double polybag.

Step 4: Slugging

1. Blend was compressed into slugs using Cadmach CU 20 machine.

2. Cadmach CU 20 compression machine was fixed with one "D" tooling punch set.

a. Upper punch: 16 mm, round, flat and plain surface b. Lower punch: 16 mm, round, flat and plain surface Step 5: In-Process Quality Control Testing of Slugs

| In-process parameters | Values/observations | | |
|---|---|---|---|
| | Average | Minimum | Maximum |
| Hardness (N) | 63.9 | 50 | 80 |
| Thickness (mm) | 3.1 | 2.78 | 3.15 |
| Weight (mg) | 625.71 | 600 | 642.5 |

Step 6: Milling

1. Slugs were passed through ASTM 20 mesh

2. Above slugs were then passed through ASTM 40 mesh

3. Granules were collected into a double polybag

Step 7: Dispensing (Extra-Granular)

Extra-granular materials were weighed separately into a polybags.

Step 8: Sifting

1. Milrinone granules and HPMC K100M were co-sifted through ASTM 40 mesh.

2. Microcrystalline cellulose was sifted through ASTM 40 mesh.

3. Magnesium stearate was sifted through ASTM 60 mesh.

Step 9: Blending

1. Step 6 granules and step 8 blend were transferred into a 0.5 L Turbula Shaker Mixer for 15 min at 49 rpm.

2. Magnesium stearate was then transferred into the container and further 15 min mixing was done at 49 rpm.

3. Blend was collected into a double polybag.

Step 10: Compression

1. Cadmach CU 20 compression machine was fixed with one "D" tooling multitip punch set.

a. Upper punch: 2 mm, round, standard concave (12 tips)

b. Lower punch: 2 mm, round, standard concave (12 tips)

2. Tablets were compressed using Cadmach CU 20 compression machine.

Compression was done manually by rotating hand wheel to obtain enough hardness and thickness.

Step 11: In-Process Quality Control Testing of Core Minitablets

| In-process | Values/observations | | |
|---|---|---|---|
| parameters | Average | Minimum | Maximum |
| Hardness (N) | 27.2 | 20 | 30 |
| Thickness (mm) | 2.8 | 2.78 | 2.82 |
| Weight (mg) | 10.13 | 9.2 | 10.7 |
| Friability | | Nil | |

Manufacturing Procedure for Batch No. 017

| Ingredients | Quantity of materials (g) |
|---|---|
| Milrinone | 150.75 |
| HPMC K100M | 225.00 |
| HPMC E50 LV | 225.00 |
| Avicel PH102 | 134.25 |
| Magnesium stearate | 15.00* |
| | (half qty. Intra & half extragranular) |
| Total | |

Step 1: Dispensing

All ingredients were weighed separately into a double polybag and/or butter paper Note: Milrinone quantity was weighed based upon following calculation, Assay of Milrinone=99.70% (as is basis)

mg/tablet of Milrinone=theoretical quantity of Milrinone (mg/tablet)×100/Assay of Milrinone i.e. 2.00×100/99.7=2.01 mg The quantity of API was adjusted with Microcrystalline cellulose.

Step 2: Sifting
1. HPMC E50 LV and Milrinone were co-sifted through ASTM 40 mesh
2. Magnesium stearate was sifted through ASTM 60 mesh Step 3: Blending
1. Step 2.1 mixture was blended for 15 minutes at 15 RPM
2. Above blend was collected into a double polybag and kept ready for roller compaction.

Step 4: Roller Compaction
1. Roller compaction of above blend was done at following process parameters,

| Roller compaction process parameter | Observations/values |
|---|---|
| Screw feeder (rpm) | 20.0 |
| Hydraulic pressure (bar) | 200.0 |
| Roller unit (rpm) | 10.0 |
| Roller gap (mm) | 1.0 |
| Fine granulator speed (rpm) | 25.0 |
| Pregranulator screen size (mm) | 2.0 |
| Fine granulator screen size (mm) | 0.63 |

2. After roller compaction, granules were collected into a double polybag.

Step 5: Sifting
1. Above granules were co-sifted through ASTM 40 mesh.
2. Microcrystalline cellulose was sifted through ASTM 40 mesh.
3. Step 1 and 2 materials were mixed together.
4. Magnesium stearate was sifted through ASTM 60 mesh.

Step 6: Blending
1. Step 3 and 4 materials from above step were mixed into a double cone blender for 15 minutes at 15 rpm.
2. Finally blend was collected into a double polybag.

Step 7: Compression
1. Cadmach CU 20 compression machine was fixed with one "D" tooling multitip punch set.
 a. Upper punch: 2 mm, round, standard concave (12 tips)
 b. Lower punch: 2 mm, round, standard concave (12 tips)
2. Compression of the blend was not achieved due to fluffy nature and poor compressibility of the blend. There was uneven die filling and hence varying hardness of the tablets. Compression of the batch was discontinued.

Note: Granules ready for compression was subjected to further processing to improve compressibility.

Step 8: Sifting 70 g of microcrystalline cellulose and 700 g of granules ready for compression were co-sifted through ASTM 40 mesh.

Step 9: Blending
1. Above materials were subjected for blending in a double cone blender for 15 min. at 15 rpm.
2. Granules were collected into a double lined polybag.

Step 10: Roller Compaction
1. Roller compaction of above blend was done at following parameters,

| Roller compaction process parameter | Observations/values |
|---|---|
| Screw feeder (rpm) | 20.0 |
| Hydraulic pressure (bar) | 100.0 |
| Roller unit (rpm) | 10.0 |
| Roller gap (mm) | 1.0 |
| Fine granulator speed (rpm) | 25.0 |
| Pre-granulator screen size (mm) | 2.0 |
| Fine granulator screen size (mm) | 0.63 |

2. Granules were collected into a double polybag at the end.

Step 11: Sifting

Above lubricated granules and microcrystalline cellulose were co-sifted through ASTM 40 mesh.

Step 12: Granulation
1. Above granules were loaded in 5 liters capacity Rapid Mixer Granulator.
2. Initially dry mixing was done for 15 min. at impeller speed of 150 rpm.
3. Granules were wet granulated with 500 g purified water for 25 min. at impeller speed of 150 rpm.

Step 13: Drying
1. Wet granules were dried at the inlet temperature of 38 to 45° C. till moisture level remains below 2% w/w.

Step 14: Sifting

Dried granules were sifted through ASTM 30 mesh. Oversized granules were collected into a double polybag.

Step 15: Milling

Oversized granules were milled using 1 mm screen attached to the co-mil.

Step 16: Sifting

Above granules were sifted through ASTM 30 mesh

Step 17: Mixing

Step 14 and 16 granules were mixed into a double poly*.

Step 18: Compression
1. Cadmach CU 20 compression machine was fixed with one "D" tooling multitip punch set.
 a. Upper punch: 2 mm, round, standard concave (12 tips)
 b. Lower punch: 2 mm, round, standard concave (12 tips)
2. Tablets were compressed using Cadmach CU 20 compression machine. Compression was done manually by rotating hand wheel to obtain enough hardness and thickness at the adjusted average weight of 10.00 mg.

Step 19: In-Process Quality Control Testing of Core Minitablets

| In-process parameters | Values/observations | | |
|---|---|---|---|
| | Average | Minimum | Maximum |
| Hardness (N) | 22.8 | 15 | 30 |
| Thickness (mm) | 2.57 | 2.44 | 2.68 |
| Weight (mg) | 10.2 | 9.2 | 10.5 |

Step 20: Coating (Seal Coating)

1. Minitablets were seal coated using Opadry™ white at 10% w/w weight gain of film coat. Opadry™ film coating system powder was added to water and mix for 45 minutes with a propeller stirrer. The coating suspension can be made with up according to the manufacturer's instructions.

2. Coating was done using bottom spray container (2.4 liters) at following equipment parameters,

| Coating process parameter | Values |
|---|---|
| Inlet temperature | 49 to 56° C. |
| Product temperature | 38 to 43° C. |
| Exhaust temperature | 35 to 43° C. |
| Blower speed | 65 to 99% |
| Spray pump speed (rpm) | 2 to 15 |
| Atomisation (Bars) | 0.5 to 1.4 |
| Air flow (cfm) | 79 to 110 |

Step 21: In-Process Quality Control Testing of Core Minitablets

| In-process parameters | Values/observations | | |
|---|---|---|---|
| | Average | Minimum | Maximum |
| Hardness (N) | 62.2 | 52 | 68 |
| Thickness (mm) | 2.8 | 2.78 | 2.81 |
| Weight (mg) | 10.2 | 10.4 | 10.8 |

Step 22: Sustained Release Coating 1. 10% w/w sustained release coating of minitablets was done using Aquacoat ECD 30 (Ethyl cellulose dispersion) as a sustained release polymer along with Opadry™ clear and talc, where triethyl citrate was used as a plasticizer.

a. Composition of coating dispersion has been tabulated below,

| Sr. No. | Ingredients | Manufacturer | Ratio to EC solids | Total Dissolved Solids (TDS) (g) | Quantities (g) for 500 g batch size |
|---|---|---|---|---|---|
| 01 | Aquacoat EC30D | FMC Biopolymer | — | 37.93 | 126.44 g |
| 02 | Opadry clear | Colorcon | 10% | 3.79 | 3.79 g |
| 03 | Triethyl citrate | Sigma Aldrich | 25% | 9.48 | 9.48 g |
| 04 | Talc | Luzenac Pharma | 10% | 3.79 | 3.79 g |
| 05 | Purified water | FDC In-house | | | 223.16 g |

2. Coating was done by wurster coater (bottom spray container 2.4 liters) at following equipment parameters,

| Coating process parameter | Values |
|---|---|
| Inlet temperature | 49 to 56° C. |
| Product temperature | 38 to 43° C. |
| Exhaust temperature | 35 to 43° C. |
| Blower speed | 65 to 99% |
| Spray pump speed (rpm) | 2 to 15 |
| Atomisation (Bars) | 0.5 to 1.4 |
| Air flow (cfm) | 79 to 110 |

Step 23: In-Process Quality Control Testing of Core Minitablets

| In-process parameters | Values/observations | | |
|---|---|---|---|
| | Average | Minimum | Maximum |
| Hardness (N) | 71.9 | 58 | 79 |
| Thickness (mm) | 2.89 | 2.88 | 2.91 |
| Weight (mg) | 11.6 | 11.4 | 11.8 |

Step 24: Buffer Coating

1. Buffer coating was done at 10% w/w weight gain using Opadry white.

2. Coating was done using bottom spray container (2.4 liters) at following equipment parameters,

| Coating process parameter | Values |
|---|---|
| Inlet temperature | 35 to 58° C. |
| Product temperature | ° C. |
| Exhaust temperature | ° C. |
| Blower speed | % |
| Spray pump speed | rpm |
| Atomisation | Bars |
| Air flow (cfm) | |

Step 25: In-Process Quality Control Testing of Buffer Coated Minitablets

| In-process parameters | Values/observations | | |
|---|---|---|---|
| | Average | Minimum | Maximum |
| Hardness (N) | 62.2 | 52 | 68 |
| Thickness (mm) | 2.8 | 2.78 | 2.81 |
| Weight (mg) | 10.58 | 10.4 | 10.8 |

Step 26: Enteric Coating

1. Enteric coating of buffer coated minitablets was done by using Eudragit L30 D55 polymer at 40% w/w weight gain where talc was used as an antitacking agent and triethylcitrate was used as a plasticizer. The composition of coating dispersion is given in table below,

| Sr. No. | Ingredients | Manufacturer | Ratio to Eudragit solids | Total Dissolved Solids (TDS) (g) | Quantities taken for 500 g batch size |
|---|---|---|---|---|---|
| 1 | Eudragit L30D55 | Evonik | — | 162.50 | 541.67 g |
| 2 | Triethyl citrate | Sigma Aldrich | 10% | 16.25 | 16.25 g |
| 3 | Talc | Luzenac Pharma | 50% | 81.25 | 81.25 g |

-continued

| Sr. No. | Ingredients | Manufacturer | Ratio to Eudragit solids | Total Dissolved Solids (TDS) (g) | Quantities taken for 500 g batch size |
|---|---|---|---|---|---|
| 4 | Purified water | FDC in-house | | | 400.83 g |

Note:
30% excess solution was prepared to compensate manufacturing losses.

1.1 Eudragit L30D55 and Triethylcitrate were mixed together for 45 min. using overhead stirrer.
1.2 Talc was added into water slowly and was homogenized for 15 min. at 6000 rpm.
1.3 Step 1.1 and 1.2 dispersions were mixed together for 5 min. using overhead stirrer.
2. Coating was done using bottom spray container (2.4 liters) at following equipment parameters, to provide an enteric coat of 40% w/w.

| Coating process parameter | Values |
|---|---|
| Inlet temperature | 30 to 40° C. |
| Product temperature | 26 to 31° C. |
| Exhaust temperature | 26 to 30° C. |
| Blower speed | 70 to 98% |
| Spray pump speed (rpm) | 5 to 15 |
| Atomisation (Bars) | 0.5 to 1.5 |
| Air flow (cfm) | 106 to 128 |

3. After coating curing of Minitablets was done for 1 hour at product temperature between 40 to 43° C. in the equipment.

Step 27: In-Process Quality Control Testing of Enteric Coated Minitablets

| In-process parameters | Values/observations | | |
|---|---|---|---|
| | Average | Minimum | Maximum |
| Hardness (N) | 98.7 | 79 | 110 |
| Thickness (mm) | 3.25 | 3.23 | 3.26 |
| Weight (mg) | 17.67 | 17.1 | 18.1 |

Example 2

Minitablet Formulation Comprising Hydrophilic Matrix of Natural Gums

Summary Table of Gum-Based Compositions Providing Weights Used in Formulation

| Ingredients | % w/w Batch No. | | | | | | | | | |
|---|---|---|---|---|---|---|---|---|---|---|
| | 028 | 023 | 023-1 | 022 | 021 | 018 | 014 | 011 | 006 | 003 |
| Tablet core | | | | | | | | | | |
| Milrinone | 20 | 20 | 20 | 20 | 20 | 20 | 20 | 20 | 20 | 20 |
| Xanthan gum | 15 | 20 | 20 | 20 | 15 | 15 | 30 | 25 | 30 | 15 |
| Locust gum | 15 | 20 | 20 | 20 | 15 | 15 | 0 | 0 | 0 | 15 |
| Avicel PH102 | 20 | 15 | 15 | 35 | 45 | 45 | 48 | 20 | 20 | 20 |
| Lactose, Anhydrous | 25 | 20 | 20 | 0 | 0 | 0 | 0 | 29 | 25 | 25 |
| PVPK30 | 4 | 4 | 4 | 4 | 4 | 4 | 0 | 4 | 4 | 4 |
| Aerosil | 1 | 1 | 1 | 1 | 1 | 1 | 1 | 1 | 1 | 1 |
| Magnesium stearate | 1 | 1 | 1 | 1 | 1 | 1 | 1 | 1 | 1 | 1 |
| TOTAL | 100 | 100 | 100 | 100 | 100 | 100 | 100 | 100 | 100 | 100 |
| Seal Coated Core | | | | | | | | | | |
| Tablet core | 97 | — | — | — | — | — | — | — | — | — |
| Opadry clear white | 3 | — | — | — | — | — | — | — | — | — |
| TOTAL | 100 | — | — | — | — | — | — | — | — | — |
| SR Coated Core | | | | | | | | | | |
| Seal coated core | 95 | — | — | — | — | — | — | — | — | — |
| Ethyl cellulose/ triethyl citrate | 5 | — | — | — | — | — | — | — | — | — |
| TOTAL | 100 | — | — | — | — | — | — | — | — | — |
| Buffer Coated Core | | | | | | | | | | |
| CR coated core | 95 | — | — | — | — | — | — | — | — | — |
| Opadry white | 5 | — | — | — | — | — | — | — | — | — |
| TOTAL | 100 | — | — | — | — | — | — | — | — | — |
| ER Coated Core | | | | | | | | | | |
| Buffer coated core | 60 | — | — | — | — | — | — | — | — | — |
| Eudragit L36D55/ triethyl citrate/ Talc | 40 | — | — | — | — | — | — | — | — | — |
| TOTAL | 100 | — | — | — | — | — | — | — | — | — |

Manufacturing Procedure for Batch No. 028

| Ingredients | Quantity of materials (g) |
|---|---|
| Milrinone | 50.25 |
| Xanthan gum | 37.50 |
| Locust gum | 37.50 |
| Avicel PH102 | 49.75 |
| Lactose, Anhydrous | 62.50 |
| PVPK30 | 8.75 |
| Aerosil | 2.50 |
| Magnesium stearate | 1.25 |
| Total | 250.0 |

Step 1: Dispensing
All the ingredients were weighed separately into double polybags. Milrinone quantity was weighed based upon following calculation:
Assay of Milrinone=99.70% (as is basis).
Mg/tablet of Milrinone=Theoretical quantity of Milrinone (mg/tablet)×100/Assay of Milrinone
=2.00×100/99.7=2.01 mg
The quantity of API was adjusted with microcrystalline cellulose.
Step 2: Sifting
1. All the ingredients except magnesium stearate were sifted through ASTM 40 mesh.
2. Magnesium stearate was sifted through ASTM 60 mesh.
Step 3: Blending
1. Ingredients 1 to 3 from Table 1 were transferred into a 0.5 L Turbula Shaker Mixer container and blending was done for 10 min at 49 rpm.

2. Ingredients 4 to 7 were then added and further blending was done for 10 min at 49 rpm.

3. Ingredient 8 was then added and lubrication was done for 5 min at 49 rpm.

4. Blend was finally collected into a double polybag.

Step 4: Compression

3. Cadmach CU 20 compression machine was fixed with one "D" tooling multitip punch set.

a. Upper punch: 2 mm, round, standard concave (12 tips)
   b. Lower punch: 2 mm, round, standard concave (12 tips)

4. Tablets were compressed using Cadmach CU 20 compression machine. Compression was done manually by rotating hand wheel to obtain enough hardness and thickness.

Step 5: In-Process Quality Control Testing of Core Minitablets

| In-process parameters | Values/observations | | |
|---|---|---|---|
| | Average | Minimum | Maximum |
| Hardness (N) | 28 | 23 | 35 |
| Thickness (mm) | 2.47 | 2.42 | 2.53 |
| Weight (mg) | 10 | 9.0 | 10.0 |
| Friability | | Nil | |

Step 5: Seal Coating

1. Seal coating of minitablets was done at 3% w/w weight gain using Opadry white as a film coating agent. Opadry film coating system powder was added to water and mixed for 45 minutes with a propeller stirrer. The coating suspension can be made according to the manufacturer's instructions.

2. Coating was done by using Gansons coater (GAC 275) at the following parameters,

| Coating process parameter | Values |
|---|---|
| Inlet temperature | 60 to 62.3° C. |
| Product temperature | 38 to 40° C. |
| Exhaust temperature | 39 to 40° C. |
| Spray pump speed (rpm) | 2 to 3 |
| Atomisation air (kg/cm$^2$) | 0.2 |
| Fan pressure (kg/cm$^2$) | 0.2 |

Step 6: In-Process Quality Control Testing of Seal Coated Minitablets

| In-process parameters | Values/observations | | |
|---|---|---|---|
| | Average | Minimum | Maximum |
| Hardness (N) | 32 | 29 | 38 |
| Thickness (mm) | 2.52 | 2.50 | 2.55 |
| Weight (mg) | 10.3 | 10.1 | 10.5 |
| Friability | | Nil | |

Step 7: Sustained Release (SR) Coating of Minitablets

1. Minitablets were 5% w/w SR coated by Ethylcellulose dispersion (Aquacoat ECD30D) using triethyl citrate as a plasticizer.

| Ingredients | Quantities (g) |
|---|---|
| Aquacoat ECD30D | 140.28 g |
| Triethyl citrate | 8.42 g |

2. Coating was done by using Gansons coater (GAC-275) at the following parameters,

| Coating process parameter | Values |
|---|---|
| Inlet temperature | 56 to 59° C. |
| Product temperature | 38 to 40° C. |
| Exhaust temperature | 39 to 40° C. |
| Spray pump speed (rpm) | 2 to 2.5 |
| Atomisation air (kg/cm$^2$) | 0.2 |
| Fan pressure (kg/cm$^2$) | 0.2 |

3. Curing of minitablets was done at 60° C. for 2 hours in vacuum oven (without vacuum).

Step 8: In-Process Quality Control Testing of SR Coated Minitablets

| In-process parameters | Values/observations | | |
|---|---|---|---|
| | Average | Minimum | Maximum |
| Hardness (N) | 37.4 | 34 | 41 |
| Thickness (mm) | 2.65 | 2.61 | 2.68 |
| Weight (mg) | 10.62 | 10.2 | 10.9 |

Step 9: Buffer Coating

1. Seal coating of minitablets was done at 5% w/w weight gain using opadry white as a film coating agent, as described in step 5 of Batch-028.

2. Coating was done by wurster coater 2.4 L container (GPCG 1.1) at the following parameters,

| Coating process parameter | Values |
|---|---|
| Inlet temperature | 58 to 60.3° C. |
| Product temperature | 39 to 40° C. |
| Exhaust temperature | 39 to 40° C. |
| Spray pump speed (rpm) | 2 to 4 |
| Atomisation air (kg/cm$^2$) | 0.2 |
| Fan pressure (kg/cm$^2$) | 0.2 |

Step 10: In-Process Quality Control Testing of Buffer Coated Minitablets

| In-process parameters | Values/observations | | |
|---|---|---|---|
| | Average | Minimum | Maximum |
| Hardness (N) | 41.7 | 37 | 46 |
| Thickness (mm) | 2.74 | 2.70 | 2.78 |
| Weight (mg) | 11.15 | 11.03 | 11.23 |

Step 11: Enteric Coating

1. Enteric coating of buffer coated minitablets was done by Eudragit L30D55 as a enteric polymer along with triethylcitrate as a plasticizer and talc as an anti-tacking agent.

| Ingredients | Quantities (g) |
|---|---|
| Eudragit L30D55 | 333.33 g |
| Triethyl citrate | 10.00 g |
| Talc | 50.00 g |

2. Coating was done by Wurster coater 2.4 L container (GPCG 1.1) at the following parameters, to provide an enteric coat of 40% w/w.

| Coating process parameter | Values |
| --- | --- |
| Inlet temperature | 27 to 32° C. |
| Product temperature | 26 to 28° C. |
| Exhaust temperature | 26 to 28° C. |
| Blower spped (%) | 58 to 92 |
| Air flower (cfm) | 70 to 134 |
| Spray pump speed (rpm) | 2 to 3 |
| Atomisation air (Bars) | 1.0 to 1.2 |

Step 12: In-Process Quality Control Testing of Enteric Coated Minitablets

| In-process parameters | Values/observations | | |
| --- | --- | --- | --- |
| | Average | Minimum | Maximum |
| Hardness (N) | 89.89 | 74 | 107 |
| Thickness (mm) | 3.08 | 3.03 | 3.14 |
| Weight (mg) | 15.61 | 15.58 | 15.65 |

Manufacturing Procedure for Batch No. 023

| Ingredients | Quantity of materials (g) |
| --- | --- |
| Milrinone | 25.13 |
| Xanthan gum | 25.00 |
| Locust gum | 25.00 |
| Avicel PH102 | 18.63 |
| Lactose, Anhydrous | 25.00 |
| PVPK30 | 4.38 |
| Aerosil | 1.25 |
| Magnesium stearate | 0.63 |
| Total | 125 |

Step 1: Dispensing

All ingredients were weighed separately into a double polybag and/or butter paper. Note: Milrinone quantity was weighed based upon following calculation, Assay of Milrinone=99.70% (as is basis)

mg/tablet of Milrinone=theoretical quantity of Milrinone (mg/tablet)×100/Assay of Milrinone i.e. 2.00×100/99.7=2.01 mg The quantity of API was adjusted with Lactose.

Step 2: Sifting

1. Ingredients 1 to 7 from Table 1 were sifted through ASTM 40 mesh.
2. Ingredient 8 was sifted through ASTM 60 mesh.

Step 3: Blending

1. Ingredients 1 to 3 from above Table 1 were transferred into a 0.5 L Turbula Shaker Mixer container and blending was done for 10 min. At 49 rpm.
2. Ingredients 4 to 7 were then added and further blending was done for 10 min. at 49 rpm.
3. Ingredient 8 was then added and lubrication was done for 5 min. at 49 rpm.
4. Blend was finally collected into a double polybag.

Step 4: Compression

1. Cadmach CU 20 compression machine was fixed with one "D" tooling multitip punch set.
   a. Upper punch: 2 mm, round, standard concave (12 tips)
   b. Lower punch: 2 mm, round, standard concave (12 tips)
2. Tablets were compressed using Cadmach CU 20 compression machine. Compression was done manually by rotating hand wheel to obtain enough hardness and thickness.

Step 5: In-Process Quality Control Testing of Core Minitablets

| In-process parameters | Values/observations | | |
| --- | --- | --- | --- |
| | Average | Minimum | Maximum |
| Hardness (N) | 24 | 22 | 29 |
| Thickness (mm) | 2.36 | 2.33 | 2.38 |
| Weight (mg) | 10.0 | 9.0 | 10.0 |
| Friability | | Nil | |

Manufacturing Procedure for Batch No. 023 (Lot 1) Wet Granulation

Wet granulation of 102.41 g of Batch No. 023 blend was done with 55 g purified water (53.71% w/w) manually with hands. Granules were dried in Rapid dryer at product temperature of 40 to 45° C. Drying was done for total 1 h and moisture content was found to be 7.13% w/w. Granules were then passed through Co-mil using 1 mm screen. Then, 0.25% w/w magnesium stearate was added into it (magnesium stearate was previously sifted through ASTM 60 mesh) and it was mixed manually in a polybag for 2 to 3 min. Finally, the blend was compressed into minitablets.

Compression:

1. Cadmach CU 20 compression machine was fixed with one "D" tooling multitip punch set.
   a. Upper punch: 2 mm, round, standard concave (12 tips)
   b. Lower punch: 2 mm, round, standard concave (12 tips)
2. Tablets were compressed using Cadmach CU 20 compression machine. Compression was done manually by rotating hand wheel to obtain enough hardness and thickness.

In-Process Quality Control Testing of Core Minitablets

| In-process parameters | Values/observations | | |
| --- | --- | --- | --- |
| | Average | Minimum | Maximum |
| Hardness (N) | 29 | 26 | 35 |
| Thickness (mm) | 2.37 | 2.34 | 2.40 |
| Weight (mg) | 10.0 | 9 | 10 |
| Friability | | Nil | |

Manufacturing Procedure for Batch No. 022

| Ingredients | Quantity of materials (g) |
| --- | --- |
| Milrinone | 25.13 |
| Xanthan gum | 25.00 |
| Locust gum | 25.00 |
| Avicel PH102 | 43.63 |
| Lactose, Anhydrous | — |
| PVPK30 | 4.38 |
| Aerosil | 1.25 |
| Magnesium stearate | 0.63 |
| Total | 125.0 |

Step 1: Dispensing

All ingredients were weighed separately into a double polybag and/or butter paper. Note: Milrinone quantity was weighed based upon following calculation, Assay of Milrinone=99.70% (as is basis)
mg/tablet of Milrinone=theoretical quantity of Milrinone (mg/tablet)×100/Assay of Milrinone
i.e. 2.00×100/99.7=2.01 mg The quantity of API was adjusted with Microcrystalline cellulose Step 2: Sifting
1. Ingredients 1 to 6 were sifted through ASTM 40 mesh.
2. Ingredient 7 was sifted through ASTM 60 mesh.

Step 3: Blending
1. Ingredients 1 to 3 from above step were transferred into a 0.5 L Turbula Shaker Mixer container and blending was done for 10 min. At 49 rpm.
2. Ingredients 4 to 6 were then added and further blending was done for 10 min. at 49 rpm.
3. Ingredient 7 was then added and lubrication was done for 5 min. at 49 rpm.
4. Blend was finally collected into a double polybag.

Step 4: Compression
1. Cadmach CU 20 compression machine was fixed with one "D" tooling multitip punch set.
   a. Upper punch: 2 mm, round, standard concave (12 tips)
   b. Lower punch: 2 mm, round, standard concave (12 tips)
2. Tablets were compressed using Cadmach CU 20 compression machine.

Compression was done manually by rotating hand wheel to obtain enough hardness and thickness.

Step 5: In-Process Quality Control Testing of Core Minitablets

| In-process parameters | Values/observations | | |
|---|---|---|---|
| | Average | Minimum | Maximum |
| Hardness (N) | 34.2 | 31 | 40 |
| Thickness (mm) | 2.37 | 2.36 | 2.41 |
| Weight (mg) | 10.0 | 9.0 | 10.0 |
| Friability | | Nil | |

Manufacturing Procedure for Batch No. 021, 018, 011 and 006

| Ingredients | 021 | 018 | 011 | 006 |
|---|---|---|---|---|
| | Quantity of materials (g) | | | |
| Milrinone | 25.13 | 25.13 | 25.13 | 25.13 |
| Xanthan gum | 18.75 | 18.75 | 31.25 | 31.25 |
| Locust gum | 18.75 | 18.75 | — | — |
| Avicel PH102 | 56.13 | 56.13 | 25.00 | 25.00 |
| Lactose, Anhydrous | — | — | 36.75 | 36.75 |
| PVPK30 | 4.38 | 4.38 | 4.38 | 4.38 |
| Aerosil | 1.25 | 1.25 | 1.25 | 1.25 |
| Magnesium stearate | 0.63 | 0.63 | 1.25 | 1.25 |
| Total | 125.0 | 125.0 | 125.0 | 125.0 |

Same procedure as that of Batch No. 022 was followed.

In-process quality control testing of core Minitablets of Batch No. 021

| In-process parameters | Values/observations | | |
|---|---|---|---|
| | Average | Minimum | Maximum |
| Hardness (N) | 37 | 33 | 39 |
| Thickness (mm) | 2.32 | 2.27 | 2.38 |
| Weight (mg) | 10.0 | 9.0 | 10.0 |
| Friability | | Nil | |

In-Process Quality Control Testing of Core Minitablets of Batch No. 018

| In-process parameters | Values/observations | | |
|---|---|---|---|
| | Average | Minimum | Maximum |
| Hardness (N) | 35 | 33 | 38 |
| Thickness (mm) | 2.61 | 2.60 | 2.63 |
| Weight (mg) | 10.0 | 9.0 | 10.0 |
| Friability | | Nil | |

In-Process Quality Control Testing of Core Minitablets of Batch No. 011

| In-process parameters | Values/observations | | |
|---|---|---|---|
| | Average | Minimum | Maximum |
| Hardness (N) | 35 | 30 | 40 |
| Thickness (mm) | 2.40 | 2.38 | 2.41 |
| Weight (mg) | 10.0 | 9.0 | 10.0 |
| Friability | | Nil | |

In-Process Quality Control Testing of Core Minitablets of Batch No. 006

| In-process parameters | Values/observations | | |
|---|---|---|---|
| | Average | Minimum | Maximum |
| Hardness (N) | 27.3 | 22 | 32 |
| Thickness (mm) | 2.39 | 2.38 | 2.42 |
| Weight (mg) | 9.74 | 9.0 | 10.3 |
| Friability | | Nil | |

Manufacturing Procedure for Batch No. 014

| Ingredients | Quantity of materials (g) |
|---|---|
| Milrinone | 25.13 |
| Xanthan gum | 37.50 |
| Locust gum | — |
| Avicel PH102 | 60.50 |
| Lactose, Anhydrous | — |
| PVPK30 | — |
| Aerosil | 1.25 |
| Magnesium stearate | 0.63 |
| Total | 125.0 |

Step 1: Dispensing
All ingredients were weighed separately into a double polybag and/or butter paper. Note: Milrinone quantity was weighed based upon following calculation,
Assay of Milrinone=99.70% (as is basis)
mg/tablet of Milrinone=theoretical quantity of Milrinone (mg/tablet)×100/Assay of Milrinone
i.e. 2.00×100/99.7=2.01 mg The quantity of API was adjusted with microcrystalline cellulose.

Step 2: Sifting
1. Milrinone and xanthan gum were co-sifted through ASTM 40 mesh.
2. Microcrystalline cellulose and Aerosil were co-sifted through ASTM 40 mesh.
3. Magnesium stearate was sifted through ASTM 60 mesh.

Step 3: Blending
1. Step 1 and 2 blend from above step was transferred into a 0.5 L Turbula Shaker Mixer container and blending was done for 15 min. at 49 rpm.
2. Step 3 ingredient was then added and lubrication was done for 5 min. at 49 rpm.
3. Blend was finally collected into a double polybag.

Step 4: Compression
1. Cadmach CU 20 compression machine was fixed with one "D" tooling multitip punch set.
  a. Upper punch: 2 mm, round, standard concave (12 tips)
  b. Lower punch: 2 mm, round, standard concave (12 tips)
2. Tablets were compressed using Cadmach CU 20 compression machine. Compression was done manually by rotating hand wheel to obtain enough hardness and thickness.

Step 5: In-Process Quality Control Testing of Core Minitablets

| In-process parameters | Values/observations | | |
|---|---|---|---|
| | Average | Minimum | Maximum |
| Hardness (N) | 59.4 | 56 | 65 |
| Thickness (mm) | 2.37 | 2.36 | 2.39 |
| Weight (mg) | 9.8 | 9.0 | 10.4 |
| Friability | | Nil | |

Manufacturing Procedure for Batch No. 003

| Ingredients | Quantity of materials (g) |
|---|---|
| Milrinone | 25.13 |
| Xanthan gum | 18.75 |
| Locust gum | 18.75 |
| Avicel PH102 | 25.00 |
| Lactose, Anhydrous | 31.13 |
| PVPK30 | 4.38 |
| Aerosil | 1.25 |
| Magnesium stearate | 0.63 |
| Total | 125.0 |

Step 1: Dispensing
All ingredients were weighed separately into a double polybag and/or butter paper. Note: Milrinone quantity was weighed based upon following calculation,
  Assay of Milrinone=99.70% (as is basis)
  mg/tablet of Milrinone=theoretical quantity of Milrinone (mg/tablet)×100/Assay of Milrinone
  i.e. 2.00×100/99.7=2.01 mg
The quantity of API was adjusted with Microcrystalline cellulose.

Step 2: Sifting
1. Ingredients 1 to 7 were sifted through ASTM 40 mesh.
2. Ingredient 8 was sifted through ASTM 60 mesh.

Step 3: Blending
1. Ingredients 1 to 3 from above step were transferred into a 0.5 L Turbula Shaker Mixer container and blending was done for 10 min. At 49 rpm.
2. Ingredients 4 to 7 were then added and further blending was done for 10 min. at 49 rpm.
3. Ingredient 8 was then added and lubrication was done for 5 min. at 49 rpm.
4. Blend was finally collected into a double polybag.

Step 4: Compression
1. Cadmach CU 20 compression machine was fixed with one "D" tooling multitip punch set.
  a. Upper punch: 2 mm, round, standard concave (12 tips)
  b. Lower punch: 2 mm, round, standard concave (12 tips)
2. Tablets were compressed using Cadmach CU 20 compression machine. Compression was done manually by rotating hand wheel to obtain enough hardness and thickness.

Step 5: In-Process Quality Control Testing of Core Minitablets

| In-process parameters | Values/observations | | |
|---|---|---|---|
| | Average | Minimum | Maximum |
| Hardness (N) | 26 | 19 | 38 |
| Thickness (mm) | 2.08 | 2.03 | 2.15 |
| Weight (mg) | 10.0 | 9.0 | 10.0 |
| Friability | | Nil | |

Example 3

Formulation of Milrinone Beads

Summary Table of Bead Compositions Providing w/w Ratios of Components of Batch 029

| Ingredients | % w/w Batch No. 29 | | | | | |
|---|---|---|---|---|---|---|
| | 10% SR | 15% SR | 20% SR | 25% SR | 30% SR | 40% SR |
| Bead Core | | | | | | |
| sugar spheres [30/35] | 90 | 90 | 90 | 90 | 90 | 90 |
| Milrinone | 10 | 10 | 10 | 10 | 10 | 10 |
| Opadry White | | | | | | |
| PVPK30 (Kollidon 30) | | | | | | |
| Total | 100 | 100 | 100 | 100 | 100 | 100 |
| Seal Coated Bead | | | | | | |
| Drug-layered spheres | 90 | 90 | 90 | 90 | 90 | 90 |
| Opadry white | 10 | 10 | 10 | 10 | 10 | 10 |
| Total | 100 | 100 | 100 | 100 | 100 | 100 |
| SR Coated Bead Layer 1 | | | | | | |
| Seal-coated bead | 90 | 85 | 80 | 75 | 75 | 75 |
| Eudragit RS30D | 10% | 15% | 20% | 25% | 25% | 25% |
| Eudragit RL30D | | | | | | |
| Tri-ethyl citrate | | | | | | |
| Talc | | | | | | |
| Total | 100 | 100 | 100 | 100 | 100 | 100 |
| SR Coated Bead Layer 2 | | | | | | |
| SR coated Bead Layer 1 | — | — | — | — | 95 | 85 |
| Eudragit RS30D | — | — | — | — | 5 | 15 |
| Tri-ethyl citrate | — | — | — | — | | |
| Talc | — | — | — | — | | |
| Total | — | — | — | — | 100 | 100 |
| Buffer Coated Bead | | | | | | |
| SR coated Bead Layer 2 | — | — | — | — | — | 90 |
| Opadry white | — | — | — | — | — | 10 |
| Total | — | — | — | — | — | 100 |

-continued

| Ingredients | % w/w Batch No. 29 | | | | | |
|---|---|---|---|---|---|---|
| | 10% SR | 15% SR | 20% SR | 25% SR | 30% SR | 40% SR |
| ER Coated Bead | | | | | | |
| Buffer Coated Bead | — | — | — | — | — | 60 |
| Eudragit L30D55 | — | — | — | — | — | 40 |
| Talc | — | — | — | — | — | |
| Triethylcitrate | — | — | — | — | — | |
| Total | — | — | — | — | — | 100 |

The coating levels for Batch 029 were selected based upon dissolution profiles obtained for Batch. No. 024: 10% w/w and 20% w/w Eudragit RS30D coated samples of B. No. 024 were analyzed by dissolution in pH6.8 phosphate buffer for 12 hours with the intention of 12 hours profile with zero order (desired R2 value of more than 0.9). The dissolution data for two coating levels is shown in Example 6, Table 3 and indicates that in none of the cases drug release reached 100% over 12 hours dissolution period although the release was achieving zero order profile for 12 hours. Maximum drug release after 12 hours was only 46% and 42% respectively for 10% w/w and 20% w/w, sustained release coated beads with Eudragit RS30D and hence, further coating process was stopped. Due to highly retarding nature of the polymer, it was decided to add pore former (water soluble polymer) i.e. Eudragit RL30D at 1:9 ratio (Eudragit RL30D:Eudragit RS30D) to manufacture B. No. 029.

Manufacturing of Batch No. 029:

| Sr. No. | Name of equipment/instrument | Manufacturer/supplier |
|---|---|---|
| 01 | Weighing balance | Sartorius |
| 02 | Sieves | Lab supplies India Pvt. Ltd. |
| 03 | Propeller Mixer | Hally Instruments |
| 04 | Wurster coater 2.4 L (GPCG 1.1) | Glatt |
| 05 | Homogenizer | Silversons |
| 06 | Vacuum oven | Servewell instruments |

| Ingredients | Manufacturer | % of Solids | Quantities (g) |
|---|---|---|---|
| Milrinone | Chemzam Pharmatech | 61 | 45.00 |
| Kollidon 30 (binder) | BASF | 6 | 4.50 |
| Opadry white | Colorcon | 33 | 24.50 |
| Purified water | FDC In-house | | 495.23 |

Step 1: Drug Layering

1. Procedure for drug dispersion preparation:
   a. Milrinone, Kollidon 30 and Opadry white were sifted through ASTM 30 mesh. All ingredients were collected into a single polybag.
   b. Purified water was weighed into a beaker and was placed under propeller mixer to create vigorous vortex.
   c. Slowly ingredients from step a) were added into water maintaining vortex. After complete addition, propeller mixer speed was reduced to avoid vortex. Mixing was done for 30 min.

2. Drug layering by Wurster coater
   a. Wurster coater was equipped with following accessories,
      i) 2.4 L bottom spray container
      ii) Wurster column at 20 mm height
      iii) 1.2 mm liquid nozzle insert
   b. 350.0 g of sugar spheres (30/35#) [Werner, Germany] were transferred into the container.
   c. Sugar spheres were warmed to reach product temperature of 40° C.
   d. Drug dispersion was sprayed on sugar spheres at following parameters recorded over the period of 255 min coating time:

| Coating process parameter | Values |
|---|---|
| Inlet temperature | 45 to 50° C. |
| Product temperature | 39 to 42° C. |
| Exhaust temperature | 36 to 41° C. |
| Blower speed | 60 to 77% |
| Spray pump speed (rpm) | 2 to 6 |
| Atomization (Bars) | 0.8 to 1.2 |
| Air flow (cfm) | 73 to 92 | e. After coating, peristaltic pump was stopped and product temperature was allowed to reach 44° C. and then coating process was stopped.
   f. Total yield was 390.43 g.

There are two ways to find out % w/w weight gain during spray coating of beads.

Method A:

Weight gain can be calculated only after complete coating process and then the following formula can be applied to find out weight gain:

% w/w practical weight gain achieved=Final weight−Initial weight/Initial weight×100

Method B:

Coating dispersion/solution shall be prepared exactly as per described except. 40% w/w for enteric coating with 10% extra solution to cover the in-process losses. Since the solution quantity equivalent to 40% w/w is sprayed completely on the beads, it is considered that final weight gain achieved is 40% w/w.

During beads manufacturing we do several coatings during development trials manufacturing as follows,
   a. Drug layer
   b. Seal coat
   c. Sustained release coat
   d. Buffer coat (seal coat II)
   e. Enteric coat Since there are several stages involved and some polymers involved in the process with different processing conditions, the exact amount of % w/w coating weight gain may not be achieved. Due to problems such as sticking of beads on the walls of the wurster coater bowl, on the finger bag and some in process losses the weight gain may vary. The spray rate of each kind of coating dispersion/solution should be optimized and during this optimization some quantity of beads may be lost due to for example, sticking problems. Whenever sticking occurs, the process and the beads sifted through desired sized sieve to remove tuning (2 or more particles stuck together).

Step 2: Seal Coating of Drug Layered Beads (10% w/w)
   1. GPCG 1.1 was equipped with following accessories,
      a. 2.4 L bottom spray container
      b. Wurster column at 20 mm height
      c. 1.2 mm liquid nozzle insert 2. Preparation of coating solution

| Ingredients | Manufacturer | Quantities (g) |
|---|---|---|
| Opadry white | Colorcon | 42.9 |
| Purified water | FDC in-house | 493.35 | a. A vigorous vortex was created into a weighed quantity of water and slowly opadry white was added into it. After complete addition, speed was reduced to avoid vortex. Mixing was done for 45 min.
b. Coating solution was sprayed on 390.0 g of drug layered spheres at following parameters recorded over the period of 260 min. of coating time:

| Coating process parameter | Set Values | Actual Values |
|---|---|---|
| Inlet temperature | 47 ± 5° C. | 44 to 51° C. |
| Product temperature | 40 ± 3° C. | 39 to 42° C. |
| Exhaust temperature | 40 ± 3° C. | 39 to 41° C. |
| Blower speed | 57 to 70% | 57 to 70% |
| Spray pump speed (rpm) | 2 to 7 | 2 to 7 |
| Atomization (Bars) | 0.8 to 1.4 | 0.8 to 1.4 |
| Air flow (cfm) | NA | 73 to 92 |

Note:
Before starting coating, beads were warmed to reach 40° C. product temperature.

c. After coating, temperature was allowed to reach 45° C. and then coating process was stopped.
And total yield was found to be 412.0 g.

Step 3A: First Layer Sustained Release (SR) Coating of Seal Coated Beads (Using Eudragit RS30D and Eudragit RL30D at 9:1 Ratio) to Prepare Beads with 10% w/w Coating.
1. Preparation of coating dispersion:

| Ingredients | Manufacturer | Ration to total Eudragit solids (%) | TDS (g) | Quantities (g) |
|---|---|---|---|---|
| Eudragit RS30D | Evonik | 90 | 22.91 | 76.37 |
| Eudragit RL30D | Evonik | 10 | 2.55 | 8.50 |
| Talc | Luzenac Pharma | 50 | 12.72 | 12.72 |
| Triethylcitrate | Sigma-Aldrich | 20 | 5.09 | 5.09 |
| Purified water | FDC In-house | | | 272.32 |
| Total | | | | 375.00 | a. Eudragit RL30D and Eudragit RS30D were mixed together into a beaker.
b. Talc and triethylcitrate were homogenized for 10 min. at 4500 rpm in purified water at 4500 rpm of Homogenizer.
c. Polymer dispersion from step a. was then added into b. excipient dispersion and mixing was done for 30 min. at 380 rpm using propeller mixer.
2. 412.0 g of beads were transferred into the 2.4 L bottom spray container of GPCG1.1 and warmed to reach 28° C.
3. Coating was done on beads at the following parameters recorded over the period of 303 min. of coating process to achieve a first layer SR coating of 10% w/w.

| Coating process parameter | Values |
|---|---|
| Inlet temperature | 27 to 31° C. |
| Product temperature | 25 to 27° C. |
| Exhaust temperature | 25 to 27° C. |
| Blower speed | 58 to 71% |
| Spray pump speed (rpm) | 2 to 3 |
| Atomization (Bars) | 0.8 to 1.0 |
| Air flow (cfm) | 71 to 98 |

4. Total yield was 451.0 g. 21.00 g of beads were cured at 50° C. for 30 min. in vacuum oven without vacuum for analysis (dissolution test).

Step 3B: First Layer Sustained Release (SR) Coating of Seal Coated Beads (Using Eudragit RS30D and Eudragit RL30D at 9:1 Ratio) to Prepare Beads with 15% w/w Coating.

Beads prepared according to Step 2 were coated with Sustained Release coating dispersion of Eudragit RS30D and Eudragit RL30D at 9:1 ratio described in Step 3A according to the procedures described therein but for sufficient duration to achieve a Sustained Release coating of 15% w/w on beads.

Step 3C: First Layer Sustained Release (SR) Coating of Seal Coated Beads (Using Eudragit RS30D and Eudragit RL30D at 9:1 Ratio) to Prepare Beads with 20% w/w Coating.

Beads prepared according to Step 2 were coated with Sustained Release coating dispersion of Eudragit RS30D and Eudragit RL30D at 9:1 ratio described in Step 3A according to the procedures described therein but for sufficient duration to achieve a Sustained Release coating of 20% w/w on beads.

Step 3D: First Layer Sustained Release (SR) Coating of Seal Coated Beads (Using Eudragit RS30D and Eudragit RL30D at 9:1 Ratio) to Prepare Beads with 25% w/w Coating.

Beads prepared according to Step 2 were coated with Sustained Release coating dispersion of Eudragit RS30D and Eudragit RL30D at 9:1 ratio described in Step 3A according to the procedures described therein but for sufficient duration to achieve a Sustained Release coating of 25% w/w on beads.

Step 3E: Second Layer Sustained Release (SR) Coating of First Layer SR Beads Using Eudragit RS30D to Prepare Beads with Total SR 30% w/w Coating
1. Preparation of coating dispersion:

| Ingredients | Manufacturer | Quantities (g) |
|---|---|---|
| Eudragit RS30D | Evonik | 84.87 |
| Talc | Luzenac Pharma | 12.72 |
| Triethylcitrate | Sigma-Aldrich | 5.09 |
| Purified water | FDC Inhouse | 169.64 | a. Eudragit RS30D was added to a beaker.
b. Talc and Triethylcitrate were homogenized for 10 min. at 4500 rpm in purified water at 4500 rpm of Homogenizer.
c. Polymer from step a. was then added into b. excipient dispersion and mixing was done for 30 min. at 380 rpm using propeller mixer.
2. Single Layer SR beads from Step 3D were transferred into the 2.4 L bottom spray container of GPCG1.1 and warmed to reach 28° C.
3. Coating was done on beads at the following parameters recorded over a sufficient period of coating process to achieve a second layer SR coating of 5% w/w and a total SR coating of 30%.

| Coating process parameter | Values |
|---|---|
| Inlet temperature | 27 to 31° C. |
| Product temperature | 25 to 27° C. |
| Exhaust temperature | 25 to 27° C. |
| Blower speed | 58 to 71% |
| Spray pump speed (rpm) | 2 to 3 |
| Atomization (Bars) | 0.8 to 1.0 |
| Air flow (cfm) | 71 to 98 |

4. Total yield of beads were cured at 50° C. for 30 min. in vacuum oven without vacuum for analysis (dissolution test).

Step 3F: Second Layer Sustained Release (SR) Coating of First Layer SR Beads Using Eudragit RS30D to Prepare Beads with Total SR 40% w/w Coating Beads prepared according to Step 3D were coated with Sustained Release coating dispersion of Eudragit RS30D described in Step 3E according to the procedures described therein but for sufficient duration to achieve a second layer Sustained Release coating of 15% w/w and a total SR coating of 40% w/w.

Step 4: Buffer Coating of SR Coated Beads (at 10% w/w Weight Gain with Opadry White)
 1. Preparation of coating solution

| Ingredients | Manufacturer | Quantities (g) |
|---|---|---|
| Opadry white | Colorcon | 43.44 |
| Purified water | FDC in-house | 680.56 |

Preparation procedure was same as that of step 2 (2) above.

2. Coating was done on beads using GPCG1.1 bottom spray assembly at the following parameters recorded over the period of 180 min. of coating process.

| Coating process parameter | Values |
|---|---|
| Inlet temperature | 43 to 52° C. |
| Product temperature | 39 to 43° C. |
| Exhaust temperature | 35 to 43° C. |
| Blower speed | 63 to 72% |
| Spray pump speed (rpm) | 2 to 4 |
| Atomization (Bars) | 1.0 to 1.2 |
| Air flow (cfm) | 72 to 91 |

Step 5: Enteric Coating with Eudragit L30D55 at 40% w/w Enteric Weight Gain
 1. Coating solution preparation

| Ingredients | Manufacturer | Quantities (g) |
|---|---|---|
| Eudragit L30D55 | Evonik | 395.00 |
| Talc | Luzenac Pharma | 11.85 |
| Triethylcitrate | Sigma-Aldrich | 59.25 |
| Purified water | FDC Inhouse | 797.90 |

Note: Above solution was based on 395.00 g of pan load for coating and 20% extra quantities considering losses.

2. Talc and triethylcitrate were homogenized in water for 10 min. Then this excipient dispersion was poured slowly into Eudragit L30D55 dispersion while stirring slowly at 250 rpm. Finally speed was reduced to 200 rpm and mixing was done for 30 min.

3. Initially, beads were warmed to reach product temperature of 28° C. and then coating was started which lasted for 765 min and the parameters recorded are given below,

| Coating process parameter | Values |
|---|---|
| Inlet temperature | 28 to 32° C. |
| Product temperature | 26 to 28° C. |
| Exhaust temperature | 26 to 29° C. |
| Blower speed | 63 to 75% |
| Spray pump speed (rpm) | 2 to 7 |
| Atomization (Bars) | 1.2 to 1.5 |
| Air flow (cfm) | 69 to 96 |

4. Finally, curing was done for 2 hours between 40 to 43° C. in the equipment. Total yield was 543.00 g at the end of the process.

Summary Table of Bead Compositions Providing w/w Ratios of Components of Batches 024, 020 and 016

| Ingredients | % w/w Batch No. 29 | | | | | |
|---|---|---|---|---|---|---|
| | 024 10% | 024 20% | 020 20% | 020 30% | 020 40% | 016 |
| Bead Core | | | | | | |
| Sugar spheres [30/35] | 84 | 84 | 89 | 89 | 89 | 87 |
| Milrinone | 16 | 16 | 11 | 11 | 11 | — |
| Opadry White | | | | | | |
| PVPK30 (Kollidon 30) | | | | | | |
| Milrinone | | | | | | 13 |
| HPMC 6 cps | | | | | | |
| Total | 100% | 100% | 100% | 100% | 100% | 100% |
| Seal Coated Bead | | | | | | |
| Drug-layered spheres | 90 | 90 | 90 | 90 | 90 | 90 |
| Opadry White | 10 | 10 | 10 | 10 | 10 | 10 |
| Total | 100% | 100% | 100% | 100% | 100% | 100% |
| SR Coated Bead | | | | | | |
| Seal-coated bead | 90 | 80 | 80 | 70 | 60 | 70 |
| Eudragit RS30D | 10 | 20 | 20 | 30 | 40 | |
| Tri-ethyl citrate | | | | | | 30 |
| Talc | — | — | — | — | — | |
| Ethyl cellulose aqueous Dispersion | — | — | | | | |
| Opadry Clear | | | | | | |
| Total | 100% | 100% | 100% | 100% | 100% | 100% |

Manufacturing of Batch No. 024

The coating levels in Batch 020 were selected based upon highly retarding nature of the hydrophobic Eudragit RS30D polymer and also the surface area of the beads since higher surface area requires higher weight gains. Thus, 20% w/w, 30% w/w and 40% w/w Eudragit RS30D coated samples were analyzed by dissolution in pH6.8 phosphate buffer for 12 hours with the intention of 12 hours profile with zero order (desired R2 value of more than 0.9). The dissolution data for 3 coating levels is shown in Example 6, Table 3 which indicates that in none of the cases drug release reached 100% over 12 hours dissolution period although the release was achieving zero order profile for 12 hours. Maximum drug release after 12 hours was only 77%, 77% and 52% respectively for 20% w/w, 30% w/w sand 40% w/w sustained release coated beads with Eudragit RS30D (Batches 020) and hence, further coating process was stopped.

The dissolution data suggested that 10% w/w SR coat with Eudragit RS30D may give promising results to achieve 100% drug release over 12 hours. The Batch No. 024 was manufactured with Eudragit RS30D 10% and 20% w/w coating levels to see whether at 10% w/w drug coating level, 100% release can be achieved with zero order profile.

Step 1: Drug Layering

| Ingredients | Manufacturer | Quantities (g) |
|---|---|---|
| Milrinone | Chemzam Pharmatech | 82.75 |
| Kollidon 30 (binder) | BASF | 8.25 |
| Opadry white | Colorcon | 38.5 |
| Purified water | FDC Inhouse | 632.26 |

1. Procedure for drug dispersion preparation: same as that of Batch No. 029
2. Drug layering by Wurster coater
   a. Wurster coater was equipped with following accessories,
      i) 2.4 L bottom spray container
      ii) Wurster column at 20 mm height
      iii) 1.2 mm liquid nozzle insert
      iv) Type B bottom plate
   b. 500.0 g of sugar spheres (30/35#) [Werner, Germany] were transferred into the container.
   c. Sugar spheres were warmed to reach product temperature of 40° C.
   d. Drug dispersion was sprayed on sugar spheres at following parameters recorded over the period of 195 min coating time:

| Coating process parameter | Values |
|---|---|
| Inlet temperature | 47 to 54° C. |
| Product temperature | 38 to 41° C. |
| Exhaust temperature | 33 to 41° C. |
| Blower speed | 55 to 85% |
| Spray pump speed (rpm) | 3 to 17 |
| Atomization (Bars) | 0.7 to 0.8 |
| Air flow (cfm) | 66 to 100 | e. After coating, peristaltic pump was stopped and product temperature was allowed to reach 43° C. and then coating process was stopped. Total yield was 597.60 g (16% w/w).

Step 2: Seal Coating of Drug Layered Beads (10% w/w)
1. GPCG1.1 was equipped with following accessories,
   a. 2.4 L bottom spray container
   b. Wurster column at 20 mm height
   c. 1.2 mm liquid nozzle insert
   d. Type B bottom plate
2. Preparation of coating solution

| Ingredients | Manufacturer | Quantities (g) |
|---|---|---|
| Opadry white | Colorcon | 65.74 |
| Purified water | FDC in-house | 72.53 | a. A vigorous vortex was created into a weighed quantity of water and slowly opadry white was added into it. After complete addition, speed was reduced to avoid vortex. Mixing was done for 45 min.
   b. Coating solution was sprayed on 597.0 g of drug layered spheres at following parameters recorded over the period of 260 min. of coating time:

| Coating process parameter | Values |
|---|---|
| Inlet temperature | 48 to 54° C. |
| Product temperature | 39 to 42° C. |
| Exhaust temperature | 39 to 41° C. |
| Blower speed | 55 to 75% |
| Spray pump speed (rpm) | 3 to 15 |
| Atomization (Bars) | 0.5 to 1.5 |
| Air flow (cfm) | 60 to 110 |

Note:
Before starting coating, beads were warmed to reach 40° C. product temperature.

c. After coating, temperature was allowed to reach 43° C. and then coating process was stopped.

And total yield was found to be 648.6 g. There was some tuning observed hence beads were sifted through ASTM20 mesh.

Step 3a: Sustained Release (SR) Coating of Seal Coated Beads (10% w/w Using Eudragit RS30D Polymer)
1. Preparation of coating dispersion

| Ingredients | Manufacturer | Quantities (g) |
|---|---|---|
| Eudragit RS30D | Evonik | 280.4 |
| Talc | Luzenac Pharma | 16.78 |
| Triethylcitrate | Sigma-Aldrich | 41.96 |
| Purified water | FDC Inhouse | 1087.56 |

Note:
10% w/w extra solution was prepared.

a. Talc and Triethylcitrate were homogenized for 10 min. at 4500 rpm in purified water at 4500 rpm of Homogenizer.
   b. Excipient dispersion was then added into polymer dispersion and mixed for 30 min. at 500 rpm using propeller mixer. Coating dispersion was passed through ASTM 30 mesh.
2. coating was done on beads at the following parameters recorded over the period of 385 min. of coating process sufficient to provide a sustained release layer of 10% w/w.

| Coating process parameter | Values |
|---|---|
| Inlet temperature | 28 to 35° C. |
| Product temperature | 23 to 25° C. |
| Exhaust temperature | 23 to 25° C. |
| Blower speed | 62 to 78% |
| Spray pump speed (rpm) | 4 to 15 |
| Atomization (Bars) | 0.9 to 1.5 |
| Air flow (cfm) | 85 to 103 |

3. 50 g sample cured at 50° C. for 30 min. in vacuum oven without vacuum for analysis (dissolution test).

Step 3B: Sustained Release (SR) Coating of Seal Coated Beads (20% w/w Using Eudragit RS30D Polymer).

Beads prepared according to Step 2 were coated with Sustained Release coating dispersion of Eudragit RS30D described in Step 3A according to the procedures described therein but for sufficient duration to achieve a Sustained Release coating of 20% w/w on beads.

Manufacturing of Batch No. 020

The dissolution results for Batch 016 at 30% w/w of ethyl cellulose coating levels reveals that R2 value over 12 hours was below 0.9 hence, with 100% release occurring within 10 hrs. This suggested that further retardation of release was required. Batch 20 explored the utility of Eudragit RS30D as an alternative sustained release coating.

Step 1: Drug Layering

| Ingredients | Manufacturer | Quantities (g) |
| --- | --- | --- |
| Milrinone | Chemzam Pharmatech | 50.15 |
| Kollidon 30 (binder) | BASF | 5.02 |
| Opadry clear | Colorcon | 35.00 |
| Purified water | FDC Inhouse | 465.00 |

1. Procedure for drug dispersion preparation: same as that of B. No. 029
2. Drug layering by wurster coater
   a. Wurster coater was equipped with following accessories,
      i) 2.4 L bottom spray container
      ii) Wurster column at 20 mm height
      iii) 1.2 mm liquid nozzle insert
      iv) Type B bottom plate
   b. 500.0 g of sugar spheres (30/35#) [Werner, Germany] were transferred into the container.
   c. Sugar spheres were warmed to reach product temperature of 40° C.
   d. Drug dispersion was sprayed on sugar spheres at following parameters recorded over the period of 140 min coating time:

| Coating process parameter | Values |
| --- | --- |
| Inlet temperature | 42 to 47° C. |
| Product temperature | 36 to 39° C. |
| Exhaust temperature | 36 to 38° C. |
| Blower speed | 75 to 95% |
| Spray pump speed (rpm) | 3 to 10 |
| Atomization (Bars) | 1 to 1.3 |
| Air flow (cfm) | 119 to 126 | e. Total yield was 559.00 g (11% w/w).

Step 2: Seal Coating of Drug Layered Beads (10% w/w)
1. GPCG1.1 was equipped with following accessories,
   a. 2.4 L bottom spray container
   b. Wurster column at 20 mm height
   c. 1.2 mm liquid nozzle insert
   d. Type B bottom plate
2. Preparation of coating solution

| Ingredients | Manufacturer | Quantities (g) |
| --- | --- | --- |
| Opadry white | Colorcon | 55.90 |
| Purified water | FDC in-house | 504.37 | a. A vigorous vortex was created into a weighed quantity of water and slowly opadry white was added into it. After complete addition, speed was reduced to avoid vortex. Mixing was done for 45 min.
   b. Coating solution was sprayed on 559.0 g of drug layered spheres at following parameters recorded over the period of 260 min. of coating time:

| Coating process parameter | Values |
| --- | --- |
| Inlet temperature | 45 to 54° C. |
| Product temperature | 37 to 45° C. |
| Exhaust temperature | 36 to 46° C. |
| Blower speed | 75 to 85% |
| Spray pump speed (rpm) | 3 to 5 |
| Atomization (Bars) | 0.8 to 1.3 |
| Air flow (cfm) | 85 to 146 |

Note:
Before starting coating, beads were warmed to reach 40° C. product temperature.

c. After coating, temperature was allowed to reach 45° C. and then coating process was stopped.

And total yield was found to be 490.30 g. There was some tuning observed hence beads were sifted through ASTM20 mesh. There was frequent static charge generation as well hence reduction in solid content in coating solution would help.

Step 3a: Sustained Release (SR) Coating of Seal Coated Beads (20% w/w Using Eudragit RS30D Polymer)
3A.1 Preparation of Coating Dispersion:

| Ingredients | Manufacturer | Quantities (g) |
| --- | --- | --- |
| Eudragit RS30D | Evonik | 382.80 |
| Talc | Luzenac Pharma | 25.38 |
| Triethylcitrate | Sigma-Aldrich | 63.45 |
| Purified water | FDC Inhouse | 1685.69 |
| Total | | 2157.32 |

Note:
10% w/w extra solution was prepared.

1. Talc and Triethylcitrate were homogenized for 10 min. at 6000 rpm in purified water using Homogenizer.
2. Excipient dispersion was then added into polymer dispersion and mixed for 30 min at 500 rpm using propeller mixer. Coating dispersion was passed through ASTM 30 mesh.
3. Coating was done on 490.3 beads at the following parameters recorded over the period of 363 min of coating process sufficient to provide a sustained release layer of 20% w/w

| Coating process parameter | Values |
| --- | --- |
| Inlet temperature | 27 to 35° C. |
| Product temperature | 23 to 25° C. |
| Exhaust temperature | 23 to 25° C. |
| Blower speed | 73 to 95% |
| Spray pump speed (rpm) | 3 to 20 |
| Atomization (Bars) | 1.0 to 1.6 |
| Air flow (cfm) | 112 to 125 |

The sample at each coating level cured at 50° C. for 30 min. in vacuum oven without vacuum for analysis (dissolution test).

Step 3B: Sustained Release (SR) Coating of Seal Coated Beads (30% w/w Using Eudragit RS30D Polymer).

Beads prepared according to Step 2 were coated with Sustained Release coating dispersion of Eudragit RS30D described in Step 3A according to the procedures described therein but for sufficient duration to achieve a Sustained Release coating of 30% w/w on beads.

Step 3C: Sustained Release (SR) Coating of Seal Coated Beads (40% w/w Using Eudragit RS30D Polymer).

Beads prepared according to Step 2 were coated with Sustained Release coating dispersion of Eudragit RS30D described in Step 3A according to the procedures described therein but for sufficient duration to achieve a Sustained Release coating of 40% w/w on beads.

Manufacturing of Batch No. 016:
Step 1: Drug Layering

| Ingredients | Manufacturer | Quantities (g) |
|---|---|---|
| Milrinone | Chemzam Pharmatech | 50.00 |
| Hydroxypropylmethyl-cellulose | Shinetsu | 50.00 |
| Purified water | FDC Inhouse | 1150.00 |

1. Procedure for drug dispersion preparation
  a. Slowly purified water was added into water while stirring under vigorous vortex.
  b. Slowly HPMC 6 cps was added into above dispersion and mixing was continued for 1 hour without vortex.
2. Drug layering by Wurster coater
  a. Wurster coater was equipped with following accessories,
  b. 2.4 L bottom spray container
  c. Wurster column at 20 mm height
  d. 0.8 mm liquid nozzle insert
  e. Type B bottom plate
  f. 500.0 g of sugar spheres (30/35 mesh) [Werner, Germany] were transferred into the container.
  g. Sugar spheres were warmed to reach product temperature of 40° C.
  h. Drug dispersion was sprayed on sugar spheres at following parameters recorded over the period of 225 min. coating time:

| Coating process parameter | Values |
|---|---|
| Inlet temperature | 41 to 55° C. |
| Product temperature | 32 to 45° C. |
| Exhaust temperature | 30 to 41° C. |
| Blower speed | 45 to 85% |
| Spray pump speed (rpm) | 5 to 20 |
| Atomization (Bars) | 1.0 to 1.5 |
| Air flow (cfm) | 60 to 118 | i. Total yield was 573.4 g (13% w/w). However, there was some tuning observed. Curing was done for 15 min. at the product temperature of 40° C. in the equipment.

Step 2: Seal Coating of Drug Layered Beads (10% w/w)
1. GPCG1.1 was equipped with following accessories,
  a. 2.4 L bottom spray container
  b. Wurster column at 20 mm height
  c. 1.2 mm liquid nozzle insert
  d. Type B bottom plate
2. Preparation of coating solution

| Ingredients | Manufacturer | Quantities (g) |
|---|---|---|
| Opadry white | Colorcon | 55.00 |
| Purified water | FDC in-house | 495.00 |

Note:
10% w/w excess solids were taken considering process losses.

a. A vigorous vortex was created into a weighed quantity of water and slowly opadry white was added into it. After complete addition, speed was reduced to avoid vortex. Mixing was done for 45 min.
  b. Coating solution was sprayed on 500.0 g of drug layered spheres at following parameters recorded over the period of 270 min. of coating time:

| Coating process parameter | Values |
|---|---|
| Inlet temperature | 49 to 52° C. |
| Product temperature | 39 to 42° C. |
| Exhaust temperature | 38 to 41° C. |
| Blower speed | 42 to 55% |
| Spray pump speed (rpm) | 1 to 7 |
| Atomization (Bars) | 0.5 to 0.8 |
| Air flow (cfm) | 53 to 80 |

Note:
Before starting coating, beads were warmed to reach 40° C. product temperature.

c. After coating, 15 min. curing was done at the product temperature of 42° C. in the equipment. Total yield was 532.3 g.

Step 3: Sustained Release (SR) Coating of Seal Coated Beads (30% w/w Using Ethyl Cellulose as a Release Retardant Polymer and Opadry Clear as a Pore Former or Water Soluble Polymer to Control Drug Release)
  1. Preparation of coating dispersion:

| Ingredients | Manufacturer | Quantities (g) |
|---|---|---|
| Ethylcellulose aqueous dispersion | FMC Biopolymer | 379.31 |
| Opadry Clear | Colorcon | 11.38 |
| Talc | Luzenac | 11.38 |
| Triethylcitrate (TEC) | Sigma Aldrich | 28.45 |
| Purified water | FDC In-house | 669.48 |

Note:
10% w/w extra solution was prepared.

a. Using propeller mixer, TEC and Aquacoat EC30D were mixed for 1 hour at low rpm to avoid vortex.
  b. Talc was homogenized in 300 g purified water for 5 min.
  c. Opadry clear was slowly mixed in 483.28 g of purified water at slow rpm using propeller mixer for 45 min till clear solution was formed.
  d. Slowly c. solution was added into step a. dispersion and followed by addition of step b. dispersion into it.

2. coating was done on 500 g seal coated beads at the following parameters recorded over the period of 345 min. of coating process.

| Coating process parameter | Values |
|---|---|
| Inlet temperature | 49 to 51° C. |
| Product temperature | 37 to 40° C. |
| Exhaust temperature | 35 to 39° C. |
| Blower speed | 50 to 90% |
| Spray pump speed (rpm) | 1 to 10 |
| Atomization (Bars) | 0.5 to 1.5 |
| Air flow (cfm) | 69 to 114 |

Note: 5 to 6 g sample was collected at 10% w/w, 15% w/w, 20% w/w, 25% w/w and 30% w/w coating levels. Coating solution was already divided as per each coating levels w/w.

3. Curing was done for 1 hour at the product temperature of 60° C. in the equipment for 30% w/w SR coated beads. Other samples were cured in the vacuum oven for 1 hour at 60° C.

Example 4

Immediate Release Milrinone Formulation

Batch Number: FDC12-8005042-033

| Sr. no | Composition | % w/w | Amount/tablet (mg) |
|---|---|---|---|
| 01 | Milrinone | 20 | 02 |
| 02 | Avicel PH 102 | 30 | 03 |
| 03 | Lactose anhydrous | 45 | 4.5 |
| 04 | Kollidon 30 | 3.5 | 0.35 |
| 05 | Aersoil | 01 | 0.1 |
| 06 | Magnesium stearate | 0.5 | 0.05 |
| | Total | 100 | 10.0 |

Procedure:
1. Weighing:
All the listed ingredients were accurately weighed into double line polybags, labelled and tagged.
2. Sifting:
All the excipients and Milrinone except magnesium stearate were sifted through ASTM 40 mesh.
Magnesium stearate is sifted through ASTM 60 mesh.
3. Blending:
Milrinone and other excipients except magnesium stearate were added into Turbula shaker mixer and mixed for 15 min. Magnesium stearate was added into the blend and mixed for 5 min.
4. Compression:
The lubricated blend was compressed using circular B tooling punches with 2 mm tips.
In process checks:
Weight of Tablets: 10 mg
Hardness: 30 N-40 N
Thickness: 2.4 mm-2.5 mm
Friability: 0.486%
Disintegration test: 4 to 5 min

Example 5 pH Solubility Studies on Milrinone

Aim: To perform the saturated solubility of Milrinone in different buffers.
Buffers:
1. pH 1.2-Hydrochloric Acid Buffer
2. pH 4.5-Acetate Buffer
3. pH 6.8-Phosphate Buffer
4. pH 7.4-Phosphate Buffer.

Procedure:
1. 2 mL buffer solution is placed into a 8 mL USP Type I clear glass vial (with screw cap and PTFE septa)
2. 10 mg of Milrinone is added in each vial and the vial is shaken to dissolve the compound.
3. The addition of Milrinone is continued till the formation of saturated solution.
4. The pH of the saturated solution is measured after the addition of Milrinone.
5. If there is any difference in pH more than 0.1 units is observed when compared to the initial pH, the pH was adjusted with acid or base respectively to bring it to the initial pH.
6. The vials are closed with screw cap and kept for mixing using rotary tube shaker for 24 h.

Note: The vials are observed at frequent intervals and if the solution is clear, further amount of Milrinone is added to make a saturated solution.

Results:
The solubility of Milrinone at different pH buffers

| Sr. no | Buffer | Saturated solubility (mg/mL) |
|---|---|---|
| 1 | pH 1.2 Hydrochloric Acide Buffer | 25.385 mg/mL |
| 2 | pH 4.5 Acetate Buffer | 1.826 mg/mL |
| 3 | pH 6.8 Phosphate Buffer | 0.742 mg/mL |
| 4 | pH 7.4 Phosphate Buffer | 0.603 mg/mL |

Conclusion: The solubility results indicate that Milrinone is highly soluble in acidic pH, and the solubility is decreased gradually with increase in pH. Thus the discriminatory dissolution media for Milrinone tablets should be pH 6.8 or 7.4.

Example 6

Dissolution Profiles of Formulations

Reagents
1. Potassium dihydrogen orthophosphate (AR grade)
2. Hydrochloric acid (AR grade)
3. Sodium hydroxide (AR grade)
4. Methanol (HPLC grade)
5. Water (HPLC grade)

Dissolution Parameters (for Acid Stage)
Medium 0.1N Hydrochloric acid, 900 mL
Temperature: 37.0±0.5° C.
Apparatus: USP Apparatus II (paddle)
Rotational speed 50 rpm
Sampling time 2 h Preparation of 0.1N Hydrochloric Acid pH 1 Diluent and Dissolution Buffer
8.5 mL of concentrated hydrochloric acid in 1000 mL of water, mix well.

Preparation of pH 6.8 Diluent
Dissolve 6.8 g Potassium dihydrogen orthophosphate and 0.9 g of sodium hydroxide in 1000 mL of water and adjust the pH to 6.8 with sodium hydroxide solution or Orthophosphoric acid.

Preparation of Standard Solution for pH 1 Analysis of Milrinone
Accurately weigh and transfer about 55 mg of Milrinone working standard into a 100 mL volumetric flask. Add about 10 mL of methanol and sonicate to dissolve then make up to the mark with 0.1N hydrochloric acid. Dilute 5 mL of above solution to 100 mL with 0.1N hydrochloric acid. Further dilute 5 mL of above solution to 100 mL with 0.1N HCl.

Preparation of Sample Solution
Transfer the content of one capsule in each of the six dissolution vessels and start the dissolution test in 0.1N HCl Dissolution Buffer. At the specified time withdraw about 10 mL of the aliquot from each dissolution vessel. Further dilute 4 mL of above solution to 10 mL with 0.1N HCl Diluent.

Dissolution Parameters (for 0.1N HCl Buffer Stage)
Medium:
0.1N HCl Buffer, 900 mL
Temperature 37.0±0.5° C.
Apparatus USP Apparatus II (paddle)
Rotational speed 50 rpm
Sampling time 1 h, 2 h.

Note. Where test article is to be exposed to 0.1N HCl Dissolution Buffer for 2 hours and then exposed to pH6.8 Buffer for 12 hours, the test article is removed from the dissolution vessel, washed briefly with water and placed immediately into the required dissolution vessel containing the pH6.8 Buffer.

Procedure

Measure the absorbance of standard (in duplicate) and sample solution using dissolution medium as blank at 265 nm.

Calculation $$\% \text{ of drug released} = \frac{AT}{AS} \times \frac{DS}{DT} \times \frac{P}{100} \times \frac{100}{C}$$

Where,
AT=Absorbance of sample solution.
AS=Average absorbance of standard solution.
DS=Dilution factor of the standard solution.
DT=Dilution factor of the sample solution.
P=Percent potency of Milrinone working standard, on as is basis.
C=Label claim of Milrinone per capsule (in mg).
Dissolution parameters (For Buffer Stage)
Medium: pH 6.8 Buffer, 900 mL Temperature: 37.0±0.5° C.
Apparatus: USP Apparatus II (paddle)
Rotational speed: 50 rpm
Sampling time: 1 h, 2 h, 3 h, 4 h, 5 h, 6 h, 7 h, 8 h, 9 h, 10 h, 11 h and 12 h.

Preparation of pH 6.8 Dissolution Buffer and Diluent.

Dissolve 6.8 g Potassium dihydrogen orthophosphate and 0.9 g of sodium hydroxide in 1000 mL of water and adjust the pH to 6.8 with sodium hydroxide solution or Orthophosphoric acid.

Preparation of Standard Solution

Accurately weigh and transfer about 55 mg of Milrinone working standard into a 100 mL volumetric flask. Add about 10 mL of methanol and sonicate to dissolve, then make up to the mark with pH 6.8 Diluent. Dilute 5 mL of above solution to 200 mL with Diluent.

Preparation of Sample Solution

Transfer the content of one capsule in each of the six dissolution vessels and start the dissolution test in pH 6.8 Dissolution Buffer. At the specified time withdraw about 10 mL of the aliquot from each dissolution vessel. Further dilute 4 mL of above solution to 10 mL with diluent.

Procedure

Measure the absorbance of standard (in duplicate) and sample solution using dissolution medium as blank at 265 nm.

Calculation $$\% \text{ of drug released} = \frac{AT}{AS} \times \frac{DS}{DT} \times \frac{P}{100} \times \frac{100}{C}$$

Where,
AT=Absorbance of sample solution.
AS=Average absorbance of standard solution.
DS=Dilution factor of the standard solution.
DT=Dilution factor of the sample solution.
P=Percent potency of Milrinone working standard, on as is basis.
C=Label claim of Milrinone per capsule (in mg).

Figure 2:
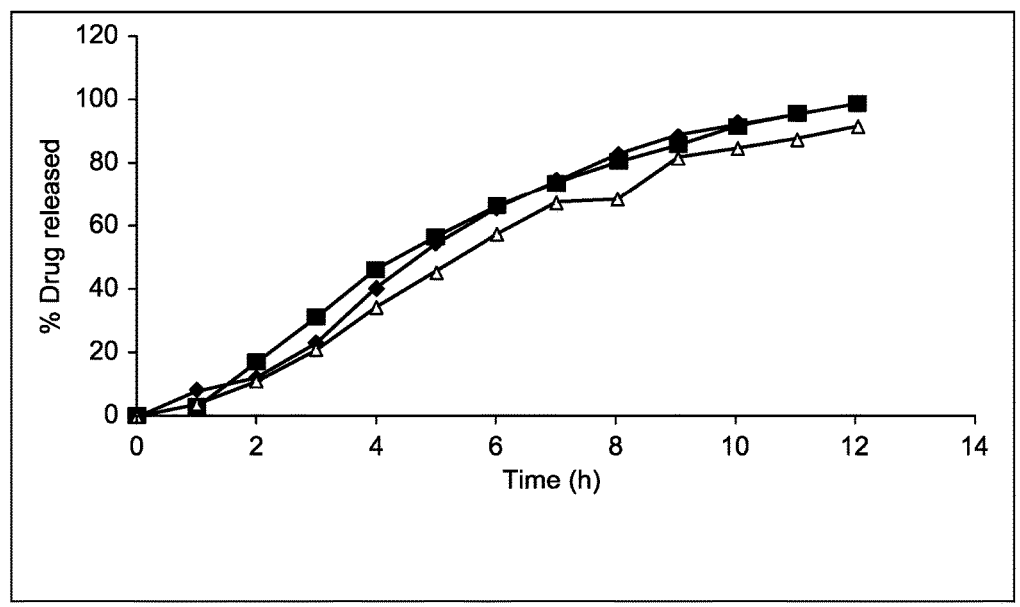
FIG. 2 is a graphical representation showing the percentage of milrinone drug released over 12 hours from a formulation of Example 1 Batch 025 (triangles). Example 2 Batch 028 (squares) and Example 3 Batch 029-40% (diamonds).
Figure 3:
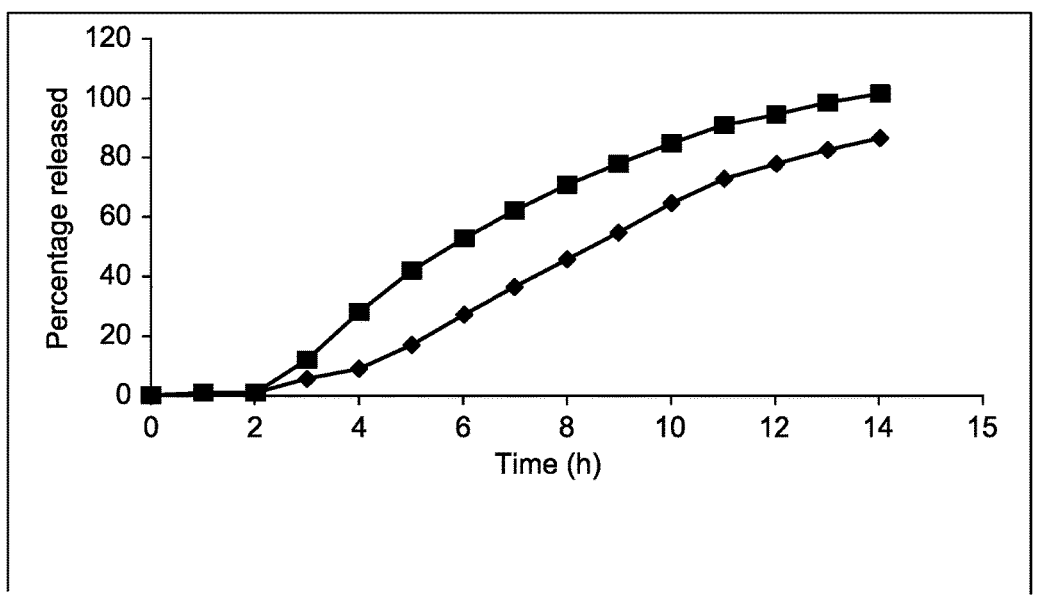
FIG. 3 is a graphical representation of the percentage of milrinone drug released over 2 hours at pH 2 followed by pH 6.8 up to 12 hours, from a formulation of Example 1 Batch 025 (diamonds) and Example 2 Batch 028 (squares).
Figure 4:
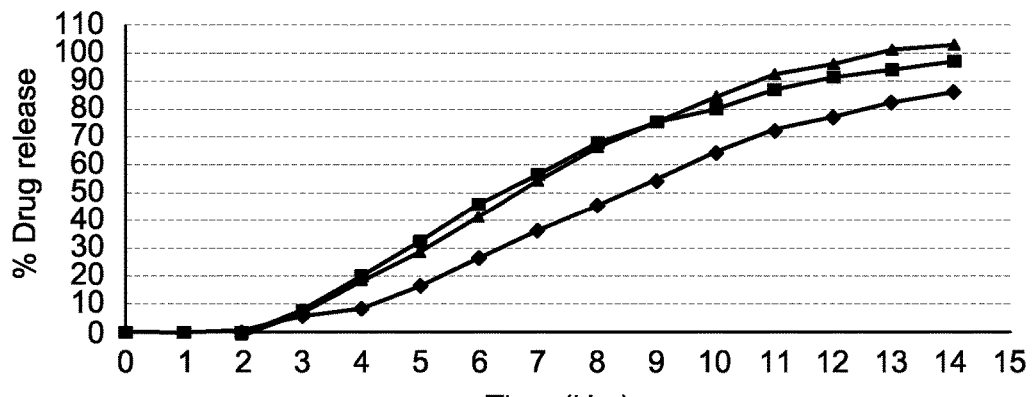
FIG. 4 is a graphical representation of the percentage of drug released over 2 hours at pH 2 followed by pH 6.8 up to 12 hours, from a formulation of Example 1 Batch 025 (diamonds). Example 1 Batch 031 (squares) and Example 1 Batch 032 (triangles).

The results are shown in the Tables below and FIGS. 2 and 3.

Example 6

TABLE 1

Dissolution data for minitablet formulation comprising hydroxypropylmethylcellulose matrix

| Time (h) | Batch-025 SR | Batch-025 No SR | Batch-017 SR | Batch-017 No SR | Batch-015 | Batch-007 | Batch-004 |
|---|---|---|---|---|---|---|---|
| | | | | % Drug released | | | |
| 0 | 0 | 0 | 0 | 0 | 0 | 0 | 0 |
| 1 | 4 | 29 | 10 | 24 | 18 | 23 | 27 |
| 2 | 11 | 38 | 21 | 38 | 33 | 35 | 40 |
| 3 | 21 | 57 | 35 | 52 | 47 | 52 | 53 |
| 4 | 34 | 65 | 49 | 65 | 57 | 65 | 63 |
| 5 | 45 | 77 | 61 | 76 | 68 | 76 | 73 |
| 6 | 57 | 87 | 72 | 86 | 77 | 88 | 83 |
| 7 | 67 | 90 | 77 | 92 | 83 | 95 | 94 |
| 8 | 68 | 95 | 87 | 97 | 88 | 99 | 100 |
| 9 | 81 | 96 | 92 | 101 | 93 | 100 | 104 |
| 10 | 84 | 97 | 95 | 100 | 96 | 101 | 106 |
| 11 | 87 | 98 | 99 | 101 | 97 | 103 | 109 |
| 12 | 91 | 97 | 99 | 103 | 98 | 104 | 111 |
| $R^2$ value-12 h | 0.973 | 0.62 | 0.929 | 0.73 | 0.817 | 0.747 | 0.808 |
| $R^2$ value-10 h | 0.982 | 0.766 | 0.97 | 0.843 | — | — | — |
| $R^2$ value-8 h | 0.973 | 0.873 | 0.99 | 0.922 | — | — | — |

TABLE 2

Dissolution data for minitablet formulation comprising hydrophilic matrix of natural gums

| Time (h) | 0.28 % 5EC | 028 | 023-1 | 023 | 022 | 021 | 018 | 014 | 011 | 006 | 003 |
|---|---|---|---|---|---|---|---|---|---|---|---|
| | | | | | % Drug released | | | | | | |
| 0 | 0 | 0 | 0 | 0 | 0 | 0 | 0 | 0 | 0 | 0 | 0 |
| 1 | 3 | 19 | 18 | 23 | 28 | 68 | 99 | 19 | 29 | 23 | 24 |
| 2 | 17 | 33 | 30 | 39 | 38 | 77 | 102 | 34 | 37 | 26 | 32 |
| 3 | 31 | 45 | 40 | 46 | 50 | 81 | 103 | 48 | 49 | 35 | 43 |
| 4 | 46 | 54 | 49 | 59 | 61 | 85 | 103 | 63 | 60 | 40 | 54 |
| 5 | 56 | 63 | 59 | 68 | 69 | 85 | 104 | 77 | 69 | 46 | 65 |
| 6 | 66 | 71 | 65 | 74 | 74 | 90 | 103 | 89 | 78 | 54 | 73 |
| 7 | 73 | 77 | 71 | 80 | 83 | 92 | 105 | 99 | 84 | 62 | 83 |
| 8 | 80 | 82 | 77 | 85 | 87 | 92 | 104 | 102 | 89 | 66 | 87 |
| 9 | 85 | 87 | 81 | 89 | 90 | 96 | 105 | 104 | 101 | 72 | 94 |
| 10 | 91 | 92 | 84 | 95 | 94 | 97 | 106 | 101 | 103 | 74 | 98 |
| 11 | 95 | 94 | 87 | 95 | 97 | 98 | 108 | 101 | 107 | 76 | 101 |
| 12 | 98 | 98 | 89 | 97 | 99 | 98 | 107 | 103 | 105 | 78 | 105 |
| $R^2$ value-12 h | 0.954 | 0.846 | 0.845 | 0.770 | 0.747 | 0.69 | NA | 0.756 | 0.823 | 0.848 | 0.880 |
| $R^2$ value-10 h | 0.974 | 0.891 | 0.897 | 0.843 | 0.811 | 0.42 | NA | | | | |
| $R^2$ value-8 h | 0.982 | 0.923 | 0.934 | 0.881 | 0.869 | 0.18 | NA | | | | |

TABLE 3

Dissolution data for Bead formulation Batches 16, 20, and 24

| Time (h) | 024 10% | 024 20% | 020 20% | 020 30% | 020 40% | 0.16 |
|---|---|---|---|---|---|---|
| | | | % Drug released | | | |
| 0 | 0 | 0 | 0 | 0 | 0 | 0 |
| 1 | 11 | 4 | 9 | 9 | 7 | 20 |
| 2 | 13 | 8 | 16 | 10 | 8 | 45 |
| 3 | 17 | 15 | 22 | 14 | 8 | 55 |
| 4 | 22 | 17 | 30 | 22 | 13 | 62 |
| 5 | 25 | 19 | 35 | 27 | 19 | 69 |
| 6 | 28 | 22 | 44 | 37 | 24 | 78 |
| 7 | 30 | 26 | 48 | 45 | 29 | 85 |
| 8 | 34 | 29 | 54 | 50 | 34 | 90 |
| 9 | 36 | 32 | 59 | 64 | 39 | 95 |
| 10 | 39 | 34 | 65 | 61 | 44 | 99 |
| 11 | 44 | 40 | 71 | 68 | 47 | 103 |
| 12 | 46 | 42 | 77 | 77 | 52 | 105 |
| $R^2$ value-12 h | 0.922 | 0.984 | 0.990 | 0.983 | 0.983 | 0.772 |
| $R^2$ value-10 h | 0.899 | 0.976 | 0.989 | 0.973 | 0.974 | 0.821 |
| $R^2$ value-8 h | 0.898 | 0.975 | 0.991 | 0.976 | 0.961 | 0.859 |

TABLE 4

Dissolution data for Pellet formulation Batch 29

| Time (h) | 029 10% | 029 15% | 029 20% | 029 25% | 029 300% | 029 40% |
|---|---|---|---|---|---|---|
| | | | % Drug released | | | |
| 0 | 0 | 0 | 0 | 0 | 0 | 0 |
| 1 | 37 | 29 | 25 | 25 | 7 | 8 |
| 2 | 53 | 44 | 43 | 43 | 20 | 12 |
| 3 | 64 | 57 | 55 | 54 | 47 | 23 |
| 4 | 74 | 66 | 66 | 66 | 65 | 40 |
| 5 | 81 | 76 | 76 | 73 | 78 | 54 |
| 6 | 88 | 82 | 82 | 81 | 87 | 65 |
| 7 | 93 | 88 | 89 | 85 | 96 | 74 |
| 8 | 97 | 92 | 96 | 91 | 94 | 82 |
| 9 | 99 | 96 | 99 | 95 | 96 | 88 |
| 10 | 100 | 100 | 103 | 99 | 98 | 92 |
| 11 | 101 | 101 | 103 | 100 | 100 | 95 |
| 12 | 101 | 102 | 106 | 102 | 100 | 98 |
| $R^2$ value-12 h | 0.425 | 0.659 | 0.733 | 0.706 | 0.787 | 0.96 |
| $R^2$ value-10 h | 0.589 | 0.758 | 0.822 | 0.792 | 0.876 | 0.979 |
| $R^2$ value-8 h | 0.711 | 0.822 | 0.878 | 0.847 | 0.948 | 0.978 |

TABLE 5

Dissolution data for enteric coated sustained release formulations

| | | Percentage drug released | | |
|---|---|---|---|---|
| pH | Time (h) | Batch-025 SR: 10% ER: 40% | Batch-028 SR: 5% ER: 30% | Batch-029 SR: 40% ER: 40% |
| 2 | 0 | 0 | 0 | 0 |
| | 1 | 0 | 1 | 1 |
| | 2 | 1 | 1 | 2 |
| 6.8 | 3 | 6 | 12 | 12 |
| | 4 | 9 | 28 | 12 |
| | 5 | 17 | 42 | 14 |
| | 6 | 27 | 53 | 15 |
| | 7 | 37 | 62 | 18 |
| | 8 | 46 | 71 | 25 |
| | 9 | 55 | 78 | 37 |
| | 10 | 65 | 85 | 48 |
| | 11 | 73 | 91 | 57 |
| | 12 | 78 | 95 | 64 |
| | 13 | 83 | 99 | 74 |
| | 14 | 87 | 102 | 76 |
| | $R^2$ value-12 h | 0.983 | 0.912 | 0.935 |

Conclusion: The dissolution profiles for Batch-025, -028 and -029 each show less than 10% release of milrinone at pH 2, which is consistent with minimal release of the active pharmaceutical ingredient in the stomach. The dissolution profiles for Batch-025, -028 and -029 each show zero order release of milrinone at pH 6.8 to provide about 100% release of the active pharmaceutical ingredient over about 12 hours, a sustained release profile which is consistent with achieving a plasma exposure in patients that is similar to that achieved by the current dosing regime with IV formulations of milrinone.

TABLE 6

Comparative dissolution profile of Enteric caoted minitablets in 0.1N HCl followed by pH 6.8 phopshate buffer

| Time | FDC11-8005042-025 (40% Enteric Coat) | FDC12-8005042-031 (30% Enteric Coat) | FDC12-8005042-032 (30% Enteric Coat) |
|---|---|---|---|
| 0 | 0 | 0 | 0 |
| 1 | 0 | 0 | 0 |
| 2 | 1 | 0 | 0 |
| 3 | 6 | 8 | 8 |
| 4 | 9 | 20 | 19 |
| 5 | 17 | 33 | 29 |
| 6 | 27 | 46 | 42 |
| 7 | 37 | 57 | 55 |
| 8 | 46 | 68 | 67 |
| 9 | 55 | 76 | 76 |
| 10 | 65 | 81 | 85 |
| 11 | 73 | 88 | 93 |
| 12 | 78 | 92 | 97 |
| 13 | 83 | 95 | 102 |
| 14 | 87 | 98 | 104 |
| $R^2$ value | 0.974 | 0.966 | 0.974 |
| Assay | 84.1% w/w | 99.0% w/w | 105.4% w/w |

Conclusion: Batch 031 with 7.5% Aquacoat ECD coating as compared to 10% coating in Batch 025 provides a slight faster release while maintaining the zero-order release. Batch 032 was manufactured as a reproducibility batch of Batch 031 to confirm the results. Both the optimized batches showed similar zero order release profile as expected. Batch 032 showed maximum release up to 105% as the assay of this batch is 105%. The enteric coating was reduced from 40% to 30% as it was sufficient to prevent the drug release in stomach.

Example 7

Pharmacokinetic Study of HPMC ER Milrinone Formulation (Example 1 Batch 032) Versus IR Milrinone Formulation (Example 4) in Dogs
Experimental Materials Pentagastrin and Ammonium formate were purchased from Sigma (St. Louis, Mo.). Amrinone was purchased from LKT Lab (St. Paul, Minn.). Milrinone formulations Example 1 Batch 032 (ER milrinone) and Example 4 (IR milrinone) were prepared as described. Gelatin capsules were received from Torpac (Fairfield, N.J.). Dichloromethane and high performance liquid chromatography (HPLC) grade acetonitrile was purchased from Honeywell (Muskegon, Mich.). Water was obtained using a Millipore system (Billerica, Mass.). American Chemical Society grade formic acid was received from Acros Organics (New Jersey).

Animals

Purpose-bred female beagle dogs (Marshall Farms, North Rose, N.Y.) weighing between 8 and 11 kg were housed unrestrained in accordance with Association for Assessment and Accreditation of Laboratory Animal Care International (AAALAC) guidelines.

Dogs were maintained on 300 g of 21% protein dog diet #2021 (Harlan Teklad, Madison, Wis.) once daily when not on study. Prior to each study, dogs were fasted overnight. All studies were conducted in accordance with the Guide for the Care and Use of Laboratory Animals (National Research Council, 1996).

Gastric pH-Modifying Treatment and Dosing

Pentagastrin was dissolved in saline (0.024 mL/kg) and administered via. IM injection in the animal's right or left hind leg (6 ug/kg) 30 minutes prior to test article administration. Following dose administration, the area was gently massaged.

The oral milrinone doses were prepared by counting minitablets into size-3 gelatin capsules. One or two milrinone filled capsule was orally administered to each dog, followed by water (10 mL) to assist swallowing. The experiments were conducted in two groups of three dogs each.

Assessing pH-Dependent Absorption

Beagle dogs (n=3) were dosed in a nonrandomized, crossover design, with at least a 1 week washout between treatments. All animals were fed their normal daily ration of food the day prior to dose administration. All animals were fasted at 17:40 the day prior to IR dose administration and at 18:22 the day prior to ER dose administration. All animals were fed following the 3 hr collections. The IR and ER milrinone formulations were orally administered (5 mg/kg in gelatin capsules) to pentagastrin-pretreated animals. Serial blood samples (2 mL) were collected from the jugular vein into potassium ethylenediaminetetraacetic acid tubes before dose and 0.5, 1, 1.5, 3, 6, 9, 11, 12, 14, 18, 24, 30, 36, 42 and 48 h after dose. Blood samples were kept on ice until processed for plasma. Blood samples were centrifuged at 3200 RPM for 10 minutes at approximately 5° C. Plasma samples were directly transferred to 96-well plate tubes (1.1 mL). Plugs were placed on the tubes. Plasma samples were stored at −20±5° C. until analyzed by liquid chromatography-tandem mass spectrometry (LC/MS/MS).

Sample Analysis

Milrinone was extracted from dog plasma using dichloromethane protein precipitation. Calibration curves were constructed using commercial beagle dog plasma spiked with individual test compounds over the analysis range of 0.5-500 ng/mL. Fifty microliters of each plasma sample and internal standard (aminone, 2 ng) were added to micro centrifuge tubes. One volume (1.0 mL) of dichloromethane was added to each tube, and the rack was vortexed for approximately 6 min to aid in the precipitation. The tubes were centrifuged at 13,000 rpm at room temperature for 6 min. Supernatants (800 uL) were transferred to a clean culture tubes and dried down at room temperature using Turbovap. The recon solution (150 uL of mobile phase A) was added to the dried tubes and subjected to LC/MS/MS analysis. Sample analysis was performed with 20 uL sample injection on an AB Sciex API-4000 triple quadrupole mass spectrometer. Analytes were separated using a Betasil C8 (100×2.1 mm) 5μ (Thermo Electron Co).

Chromatographic conditions were 10% mobile phase A (1/9, acetonitrile/10 mM ammonium formate, pH 3.0) and 90% mobile phase B (0.1% formic acid in acetonitrile) at 0.3 ml/min, ramped to 80% MP A in 1.5 min, then to 90% MP-A in 2 min. The system was returned to initial over 10 secs, and the column was reequilibrated at initial conditions for 1.4 min. LC/MS/MS analysis was carried out at positive ion mode using multiple reaction monitoring (MRM) transitions for milrinone (m/z 212→140) and the internal standard (aminone, m/z 188→433). Data analysis used linear fitting with 1/x2 weighting. All analytical results were within acceptable specifications, including performance of quality control samples, reproducibility, linearity, accuracy, and precision. The lower limit of quantitation was established at 0.5 ng/mL using the predefined criteria for reproducibility, accuracy, and precision.

Pharmacokinetic Analysis

The plasma concentrations versus time profiles obtained after oral administration of IR Milrinone and ER Milrinone were analyzed using noncompartmental analysis (WinNonlin® Professional, Version 5.2 software; Pharsight Corp., Mountain View, Calif.). Cmax was defined as the highest observed plasma concentration, and Tmax was the time at which Cmax occurred. The area under the concentration-time curve from zero to the last quantifiable time point (AUC0-t) was calculated using the Linear Up/Log Down method. AUC0-t was extrapolated to infinity and reported as AUC0-∞.

Results: Effect of Different Treatments on Gastric pH

Figure 5:
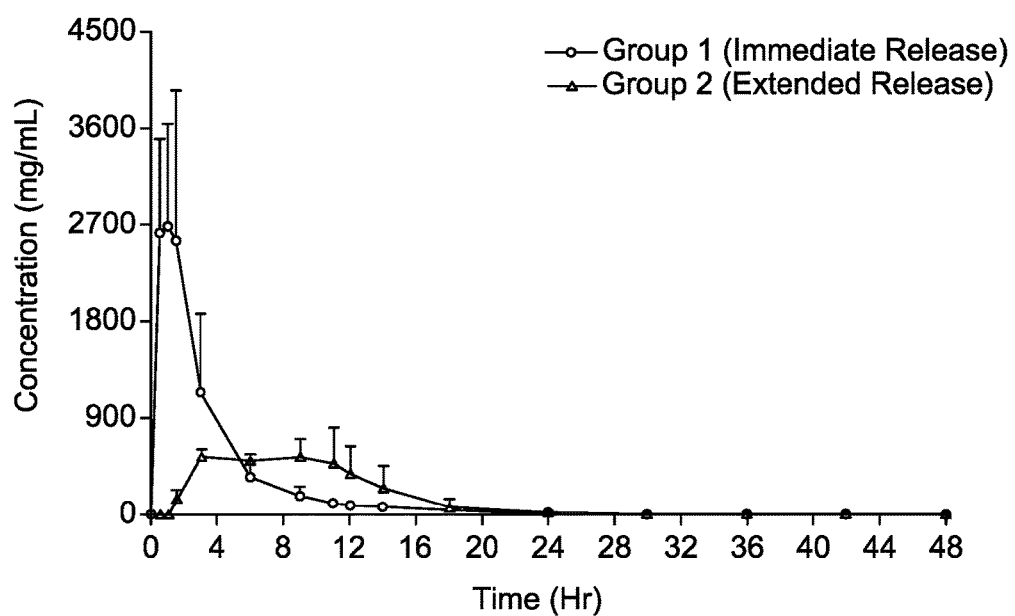
FIG. 5 is a graphical representation of average concentrations of milrinone in the plasma of female beagle dogs following 5 mg/kg PO administration of immediate release tablets of Example 4 (circles) or extended (triangles) release tablets of Example 1 Batch 032 in a gelatine capsule.

Table 1 and FIG. 5 provides the pharmacokinetic values for the IR Milrinone and ER Milrinone formulation dosing in groups of 3 dogs. This data shows that the ER Milrinone achieved a reduced Cmax in comparison to the IR Milrinone (650 ng/mL vs 3180 ng/mL); that the ER Milrinone a similar overall exposure as measured by the AUC in comparison to the IR Milrinone (6751 ng·hr/mL vs 9478 ng·hr/mL), and that the ER Milrinone maintained stable milrinone plasma concentrations over a 12 hour period.

TABLE 1

Summary Pharacokinetic Parameters of Milrinone in the Plasma of Female Beagle Dogs Following 5 mg/kg PO Adminstration of Immediate or Extended Release Tables in a Gelatin Capsule

| Parameter (units) | Group 1 (Immediate Release) | | Group 2 (Extended Release) | |
|---|---|---|---|---|
| | Mean | SD | Mean | SD |
| $C_{max}$ (ng/mL) | 3180 | 1173 | 650 | 113 |
| $t_{max}$ (hr) | 1.00 | 0.50 | 7.67 | 4.16 |
| $AUC_{(0-t)}$ (ng · hr/mL) | 9478 | 3695 | 6751 | 2150 |
| $AUC_{(0-\infty)}$ (ng · hr/mL) | 9488 | 3696 | 6759 | 2152 |
| $t_{1/2}$ (hr) | 4.97 | 0.77 | 3.71 | 0.83 |
| Vz_obs (mL/kg) | 4029 | 965 | 4143 | 1049 |
| Cl_obs (mL/hr/kg) | 586 | 234 | 802 | 298 |

PK Parameter Descriptions
$C_{max}$: Maximum Observed Concentration
$t_{max}$: Time Point at $C_{max}$
$AUC_{(0-t)}$: AUC to the last non-zero concentration (t is the corresponding time)
$AUC_{(0-\infty)}$: $AUC_{(0-\infty)} = AUC_{(0-t)} + AUC_{(t-\infty)}$
$t_{1/2}$: Half-life; time taken for drug plasma concentration to fall by one-half,
Vz_obs: Observed Volume of Distribution
Cl_obs: Observed Clearance Example 7

TABLE 2

Individual Female Beagle Dog Plasma Concentrations of Milrinone Following A Single 5 mg/kg PO Administration as Immediate Release Tablets in a Gelatin Capsule

| | Dog # 1 | | Dog # 2 | | Dog # 3 | |
|---|---|---|---|---|---|---|
| Animal Weight (kg) | 5.571 | | 9.257 | | 9.653 | |
| Dose (mg) | 28 | | 46 | | 48 | |
| Actual Dosage (mg/kg) | 5.03 | | 4.97 | | 4.97 | |
| Time (hr) | Sample Conc. (ng/mL) | | Sample Conc. (ng/mL) | | Sample Conc. (ng/mL) | Mean Conc. (ng/mL) | SD (ng/mL) |

| Time (hr) | Sample Conc. (ng/mL) | Sample Conc. (ng/mL) | Sample Conc. (ng/mL) | Mean Conc. (ng/mL) | SD (ng/mL) |
|---|---|---|---|---|---|
| 0 | BLQ | BLQ | BLQ | BLQ | N/A |
| 0.5 | 1840 | 2440 | 3570 | 2617 | 878 |
| 1 | 1750 | 2590 | 3680 | 2673 | 968 |
| 1.5 | 1210 | 4020 | 2420 | 2550 | 1410 |
| 3 | 717 | 1990 | 737 | 1148 | 729 |
| 6 | 142 | 574 | 331 | 349 | 217 |
| 9 | 234 | 217 | 71.0 | 174 | 89.6 |
| 11 | 110 | 71.3 | 118 | 99.8 | 25.0 |
| 12 | 73.0 | 87.8 | 81.2 | 80.7 | 7.41 |
| 14 | 51.3 | 89 | 58.2 | 66.2 | 20.1 |
| 18 | 30.6 | 31.5 | 30.5 | 30.9 | 0.551 |
| 24 | 5.45 | 16.3 | 8.46 | 10.1 | 5.60 |
| 30 | 1.63 | 2.34 | 2.85 | 2.27 | 0.613 |
| 36 | 2.10 | 4.22 | 2.96 | 3.09 | 1.07 |
| 42 | 1.55 | 1.74 | 1.64 | 1.64 | 0.095 |
| 48 | 0.795 | 0.964 | 2.00 | 1.25 | 0.652 |

BLQ = Below Limit of Quantitation
N/A = Not Applicable

Example 7

TABLE 3

Individual Female Beagle Dog Plasma Concentrations of Milrinone Following a Single 5 mg/kg PO Administration as Extended Release Tablets in a Gelatin Capsule

| | Dog # 4 | Dog # 5 | Dog # 6 |
|---|---|---|---|
| Animal Weight (kg) | 7.682 | 9.083 | 9.657 |
| Dose (mg) | 38 | 46 | 48 |
| Actual Dosage (mg/kg) | 4.95 | 5.06 | 4.97 |

| Time (hr) | Sample Conc. (ng/mL) | Sample Conc. (ng/mL) | Sample Conc. (ng/mL) | Mean Conc. (ng/mL) | SD (ng/mL) |
|---|---|---|---|---|---|
| 0 | BLQ | BLQ | BLQ | BLQ | N/A |
| 0.5 | BLQ | 1.19 | BLQ | BLQ | N/A |
| 1 | BLQ | 15.6 | 0.57 | 5.39 | 8.85 |
| 1.5 | 204 | 198 | 54.4 | 152 | 84.7 |
| 3 | 569 | 487 | 601 | 552 | 58.8 |
| 6 | 563 | 459 | 519 | 514 | 52.2 |
| 9 | 570 | 696 | 373 | 546 | 163 |
| 11 | 545 | 779 | 138 | 487 | 324 |
| 12 | 457 | 597 | 109 | 388 | 251 |
| 14 | 264 | 546 | 42.1 | 254 | 207 |
| 18 | 50.2 | 149 | 10.1 | 69.8 | 71.5 |
| 24 | 16.4 | 25.8 | 1.36 | 14.5 | 12.3 |
| 30 | 6.20 | 4.53 | 1.05 | 3.93 | 2.63 |
| 36 | 11.4 | 3.27 | 1.19 | 5.29 | 5.40 |

TABLE 3-continued

Individual Female Beagle Dog Plasma Concentrations of
Milrinone Following a Single 5 mg/kg PO Administration
as Extended Release Tablets in a Gelatin Capsule

| 42 | 3.33 | 1.00 | BLQ | 1.44 | 1.71 |
| 48 | 2.26 | 1.03 | BLQ | 1.10 | 1.13 |

BLQ = Below Limit of Quantitation
N/A = Not Applicable

BIBLIOGRAPHY

Diseases of the heart and blood vessels. Nomenclature and Criteria for diagnosis, 6th ed. Boston: Little, Brown and Co., 1964; 114
Alousi et al., Circulation, Supplement (1986), 73(3), 11110-11124
Arakawa et al., Neurosurgery (2001), 48(4), 723-8
Bailey et al., Anesthesiology (1999), 90(4), 1012-1018
Baim et al., The New England Journal of Medicine (1983), 309(13), 748-56
Baim et al., Journal of the American College of Cardiology (1986), 7(3), 661-70
Butterworth et al., Anesthesia & Analgesia (Baltimore), (1995), 81(4), 783-92.
Canver et al., The Annals of Thoracic Surgery (2000), 69(6), 1823-6
Cesario et al., American Heart Journal (1998), 135(1), 121-9
Chang et al., Critical Care Medicine (1995), 23(11), 1907-14
Clark R A, et al., Heart Lung Circ 2004; 13:266-73
Colucci, American Heart Journal (1991), 121(6 Pt 2), 1945-7
Copp et al., European Journal of Anaesthesiology. Supplement (1992), 5, 35-41
Cusick et al., American Journal of Cardiology (1998), 82(9), 1060-1065
Das et al., British Journal of Anaesthesia (1994), 72(4), 426-9
De Hert et al., Journal of Cardiothoracic and Vascular Anesthesia (1995), 9(3), 264-71
Doolan et al., Journal of Cardiothoracic and Vascular Anesthesia (1997), 11(1), 37-41
Givertz et al., Journal of the American College of Cardiology (1996), 28(7), 1775-80
Goldstein et al., The American Journal of Cardiology (1986), 57(8), 624-8
Gorodeski et al, Circ. HF 2:320, 2009
Hasking et al., Journal of Cardiovascular Pharmacology (1987), 9(5), 515-18
Hatzizacharias et al., American Heart Journal (1999), 138(2, Pt. 1), 241-246
Hayashida et al., The Annals of Thoracic Surgery (1999), 68(5), 1661-7
He and Yang, Journal of Cardiovascular Pharmacology, (1996), 28(2), 208-214.
Hobbs et al, Eur. Heart J. 23(23):1867-1876, 2002
Hoffman et al., Circulation (2003), 107(7), 996-1002
Juenger et al, Heart 87(3):235-241, 2002
Kikura et al., Anesthesia & Analgesia (Baltimore) (1997), 85(1), 16-22
Lloyd-Jones et al, Circulation 121:948-954, 2010
Lobato et al., Journal of Cardiothoracic and Vascular Anesthesia (2000), 14(1), 9-11 Marius-Nunez et al., American Heart Journal (1996), 132(4), 805-8
McMurray and Pfeffer, Lancet 365:1877-1889, 2005
Mehra et al., American Journal of Cardiology (1997), 80(1), 61-64
Messer et al, J. Clin. Invest. 41:725-742, 1962
Milfred-LaForest et al., American Journal of Cardiology (1999), 84(8), 894-899
Monrad et al., Circulation (1984), 70(6), 1030-7
Monrad et al., Circulation (1985), 71(5), 972-9
Packer, et al., Effect of oral milrinone on mortality in severe chronic heart failure. The PROMISE Study Research Group. N. Engl. J. Med. 1991, 325, 1468-1475
Pamboukian et al., Journal of Heart and Lung Transplantation (1999), 18(4), 367-71.
Seino, et al., Critical Care Medicine (1996), 24(9), 1490-7
Timmis et al., British Heart Journal (1985), 54(1), 36-41
Wright et al., European Journal of Anaesthesiology. Supplement (1992), 5, 21-6
Zewail et al., Texas Heart Institute Journal/from the Texas Heart Institute of St. Luke's Episcopal Hospital, Texas Children's Hospital (2003), 30(2), 109-13b

What is claimed is:

1. A method of treating a subject with heart failure, said method comprising administering to the subject an oral controlled-release formulation comprising:
   (i) a core comprising:
      (a) milrinone, or a pharmaceutically acceptable salt thereof;
      (b) hydroxypropylmethylcellulose having a viscosity of 80,000 to 120,000 cps:
      hydroxypropylmethylcellulose having a viscosity of about 50 cps;
      and at least one pharmaceutically acceptable excipient;
   (ii) a sustained release coating; and
   (iii) an enteric coating;
   wherein the hydroxypropylmethylcellulose (80,000 to 120,000 cps) and the hydroxypropylmethylcellulose (about 50 cps) are in a ratio of about 1.5:1 to 1:1.5, and the ratio of milrinone, or a pharmaceutically acceptable salt thereof, to total hydroxypropylmethylcellulose is about 1:3 to 1:5, and
   wherein the formulation exhibits zero order release of about 100% of milrinone, or a pharmaceutically acceptable salt thereof, over about 12 hours at pH 6.8.

2. The method of claim 1, wherein the formulation delivers milrinone, or a pharmaceutically acceptable salt thereof, to the blood stream at a rate of from about 0.375 µg/kg body weight/minute to about 0.75 µg/kg body weight/minute.

3. The method of claim 1, wherein the subject is a human.

4. The method of claim 1, further comprising the step of monitoring plasma concentrations of milrinone, or a pharmaceutically acceptable salt thereof, and if necessary, adjusting the dosage to achieve a plasma concentration in the range of 100 to 400 ng/mL.

5. The method of claim 1, wherein the formulation delivers milrinone, or a pharmaceutically acceptable salt thereof, to the blood stream at a rate of from about 0.1 µg/kg body weight/minute to about 1.0 µg/kg body weight/minute.

6. The method of claim 1, wherein the ratio of hydroxypropylmethylcellulose (80,000 to 120,000 cps) to hydroxypropylmethylcellulose (50 cps) is about 1:1.

7. The method of claim 1, wherein the ratio of milrinone, or a pharmaceutically acceptable salt thereof, to total hydroxypropylmethylcellulose is about 1:3.

8. A method of treating a subject with a stage, class or manifestation of heart failure, said method comprising administering to the subject an oral controlled-release formulation comprising:
   (i) a core comprising:
      (a) milrinone, or a pharmaceutically acceptable salt thereof;

(b) hydroxypropylmethylcellulose having a viscosity of 80,000 to 120,000 cps:
hydroxypropylmethylcellulose having a viscosity of about 50 cps;
and at least one pharmaceutically acceptable excipient;
(ii) a sustained release coating; and
(iii) an enteric coating;
wherein the hydroxypropylmethylcellulose (80,000 to 120,000 cps) and the hydroxypropylmethylcellulose (about 50 cps) are in a ratio of about 1.5:1 to 1:1.5, and the ratio of milrinone, or a pharmaceutically acceptable salt thereof, to total hydroxypropylmethylcellulose is about 1:3 to 1:5, and
wherein the formulation exhibits zero order release of about 100% of milrinone, or a pharmaceutically acceptable salt thereof, over about 12 hours at pH 6.8.

9. The method of claim 8, wherein the formulation delivers milrinone, or a pharmaceutically acceptable salt thereof, to the blood stream at a rate of from about 0.375 µg/kg body weight/minute to about 0.75 µg/kg body weight/minute.

10. The method of claim 8, wherein the subject is a human.

11. The method of claim 8, further comprising the step of monitoring plasma concentrations of milrinone, or a pharmaceutically acceptable salt thereof, and if necessary, adjusting the dosage to achieve a plasma concentration in the range of 100 to 400 ng/mL.

12. The method of claim 8, wherein the formulation delivers milrinone, or a pharmaceutically acceptable salt thereof, to the blood stream at a rate of from about 0.1 µg/kg body weight/minute to about 1.0 µg/kg body weight/minute.

13. The method of claim 8, wherein the ratio of hydroxypropylmethylcellulose (80,000 to 120,000 cps) to hydroxypropylmethylcellulose (50 cps) is about 1:1.

14. The method of claim 8, wherein the ratio of milrinone, or a pharmaceutically acceptable salt thereof, to total hydroxypropylmethylcellulose is about 1:3.

15. A method of treatment that permits the release of milrinone, or a pharmaceutically acceptable salt thereof, effective to ameliorate symptoms of heart failure in a subject for a period of at least 6 hours, said method comprising administering to the subject an oral controlled-release formulation comprising:
(i) a core comprising:
(a) milrinone, or a pharmaceutically acceptable salt thereof;
(b) hydroxypropylmethylcellulose having a viscosity of 80,000 to 120,000 cps:
hydroxypropylmethylcellulose having a viscosity of about 50 cps;
and at least one pharmaceutically acceptable excipient;
(ii) a sustained release coating; and
(iii) an enteric coating;
wherein the hydroxypropylmethylcellulose (80,000 to 120,000 cps) and the hydroxypropylmethylcellulose (about 50 cps) are in a ratio of about 1.5:1 to 1:1.5, and the ratio of milrinone, or a pharmaceutically acceptable salt thereof, to total hydroxypropylmethylcellulose is about 1:3 to 1:5, and
wherein the formulation exhibits zero order release of about 100% of milrinone, or a pharmaceutically acceptable salt thereof, over about 12 hours at pH 6.8.

16. The method of claim 15, wherein the formulation delivers milrinone, or a pharmaceutically acceptable salt thereof, to the blood stream at a rate of from about 0.375 µg/kg body weight/minute to about 0.75 µg/kg body weight/minute.

17. The method of claim 15, wherein the subject is a human.

18. The method of claim 15, further comprising the step of monitoring plasma concentrations of milrinone, or a pharmaceutically acceptable salt thereof, and if necessary, adjusting the dosage to achieve a plasma concentration in the range of 100 to 400 ng/mL.

19. The method of claim 15, wherein the formulation delivers milrinone, or a pharmaceutically acceptable salt thereof, to the blood stream at a rate of from about 0.1 µg/kg body weight/minute to about 1.0 µg/kg body weight/minute.

20. The method of claim 15, wherein the ratio of hydroxypropylmethylcellulose (80,000 to 120,000 cps) to hydroxypropylmethylcellulose (50 cps) is about 1:1.

21. The method of claim 15, wherein the ratio of milrinone, or a pharmaceutically acceptable salt thereof, to total hydroxypropylmethylcellulose is about 1:3.

* * * * *